United States Patent
Zhao et al.

(10) Patent No.: US 7,402,419 B2
(45) Date of Patent: Jul. 22, 2008

(54) PHOSPHITE DEHYDROGENASE MUTANTS FOR NICOTINAMIDE COFACTOR REGENERATION

(75) Inventors: Huimin Zhao, Champaign, IL (US); William W. Metcalf, Savoy, IL (US); Wilfred A. van der Donk, Champaign, IL (US); Tyler Johannnes, Urbana, IL (US); Ryan Woodyer, Champaign, IL (US)

(73) Assignees: Biotechnology Research and Development Corporation, Peoria, IL (US); Board of Trustees of the University of Illinois, Urbana, IL (US)

( * ) Notice: Subject to any disclaimer, the term of this patent is extended or adjusted under 35 U.S.C. 154(b) by 342 days.

(21) Appl. No.: 10/865,146

(22) Filed: Jun. 10, 2004

(65) Prior Publication Data
US 2005/0026250 A1 Feb. 3, 2005

Related U.S. Application Data

(60) Provisional application No. 60/477,671, filed on Jun. 11, 2003.

(51) Int. Cl.
| | |
|---|---|
| C12N 9/04 | (2006.01) |
| C12N 15/00 | (2006.01) |
| C12N 1/20 | (2006.01) |
| C12Q 1/00 | (2006.01) |
| C12Q 1/68 | (2006.01) |
| C07H 21/04 | (2006.01) |
| C12P 21/04 | (2006.01) |

(52) U.S. Cl. .......... 435/190; 435/440; 435/69.1; 435/71.1; 435/320.1; 435/252.3; 435/4; 435/6; 536/23.2

(58) Field of Classification Search ............ None
See application file for complete search history.

(56) References Cited

U.S. PATENT DOCUMENTS 6,242,233 B1  6/2001  Hoshino et al.

OTHER PUBLICATIONS

Branden et al. Introduction to Protein Structure, Garland Publishing Inc., New York, p. 247, 1991.*
Woodyer et al. Biochemistry. Oct. 14, 2003;42(40):11604-14.*
Grant et al., (1990) "Differential plasmid rescue from transgenic mouse DNAs into *Escherichia coli* methylation-restriction mutants" *Proc. Natl. Acad. Sci. U S A.* 87 (12): 4645-9.
Hofmann et al., (1999) The PROSITE Database, its status in 1999. *Nucleic Acids Res.* 27(1): 215-9.
Schink and Friedrich (2000) Phosphite oxidation by sulphate reduction. *Nature.* 406(6791): 37.
Kennedy and Thompsoon (1970) Phospholipids: localization in surface membranes of *Tetrahymena. Science* 168(934): 989-91.
Kulakova et al., (1997) Cloning of the phosphonoacetate hydrolase gene from *Pseudomonas fluorescens* 23F encoding a new type of carbon-phosphorus bond cleaving enzyme and its expression in *Escherichia coli* and *Pseudomonas putida*. Gene (195(1): 49-53.

(Continued)

*Primary Examiner*—Yong D. Pak
(74) *Attorney, Agent, or Firm*—Barnes & Thornburg LLP; Alice O. Martin

(57) ABSTRACT

Phosphite dehydrogenase mutant enzymes were generated that provide relaxed cofactor specificity and increased thermostability over the wild type enzyme. The mutant enzymes are useful for nicotinamide cofactor regeneration.

7 Claims, 24 Drawing Sheets

OTHER PUBLICATIONS

Tishkov et al., (1996) Site-directed mutagenesis of the formate dehydrogenase active centre: role of the His332-Gln313 pair in enzyme catalysis *FEBS Lett.* 390(1): 104-8.

Garcia Costas, Amaya M., et. al. (2001) "Purification and Characterization of a Novel Phosphorus-oxidizing Enzyme from *Pseudomonas stutzeri* WM88" *The Journal of Biological Chemistry* 276: 17429-17436.

Metcalf, William W. and Wolfe, Ralph S. (1998) "Molecular Genetic Analysis of Phosphite and Hypophosphite Oxidation by *Pseudomonas stutzeri* WM88" *Journal of Bacteriology* 180, 21: 5547-5558.

Vrtis, Jennifer M. et. al. (2001) "Phosphite Dehydrogenase: An Unusual Phosphoryl Transfer Reaction" *J. Am. Chem. Soc.* 123: 2672-2673.

* cited by examiner

```
PTDH        -------MLPKLVITHRVHDEILQLLAPHCELMTNQTDSTLTREEILRRCRDAQAMMAFM  53
1GDH        --------KKKILITWPLPEAAMARARESYDVIAHGDDPKITIDEMIETAKSVDALLITL  52
1PSD        AKVSLEKDKIKFLLVEGVHQKALESLRAAGYTNIEFHKGALDDEQLKESIRDAHFIGLRS  60
2D1D        ------MTKVFAYAIRKDEEPFLNEWKEAHKDIDVDYTDKLLTPETAKLAKGADGVVVYQ  54
                    :  :              :  :  .   :...   :

PTDH        PDRVDADFLQACPE--LRVVGCALKGFDNFDVDACTARGVWLTFVPDLLTVPTAELAIGL  111
1GDH        NEKCRKEVIDRIPEN-IKCISTYSIGFDHIDLDACKARGIKVGNAPHGVTVATAEIAMLL  111
1PSD        RTHLTEDVIN-AAEK-LVAIGCFCIGTNQVDLDAAAKRGIPVFNAPFSNTRSVAELVIGE  118
2D1D        QLDYTADTLQALADAGVTKMSLRNVGVDNIDMDKAKELGFQITNVPVYSPNAIAEHAAIQ  114
              : ::    .:    : :.     * ::.*:*  .   *. :   .*    . .**  .

PTDH        AVGLGRHLRAADAFVRSGEFQGWQP-QFYGTGLDNATVGILGMGAIGLAMADRLQGWGAT  170
1GDH        LLGSARRAGEGEKMIRTRSWPGWEPLELVGEKLDNKTLGIYGFGSIGQALAKRAQGFDMD  171
1PSD        LLLLLRGVPEANAKAHRGVWNKLAAGSFEARGKK---LGIIGYGHIGTQLGILAESLGMY  175
2D1D        AARVLRQDKRMDEKMAKRDLR-WAP--TIGREVRDQVVGVVGTGHIGQVFMRIMEGFGAK  171
                     *           :       .            :*: *  * **  :   :.. .

PTDH        LQYHEAKALDTQTEQR-LGLRQVACSELFASSDFILLALPLNADTQHLVNAELLALVRPG  229
1GDH        IDYFDTHRASSSDEASYQATFHDSLDSLLSVSQFFSLNAPSTPETRYFFNKATIKSLPQG  231
1PSD        VYFYDIENKLPLGNAT----QVQHLSDLLNMSDVVSLHVPENPSTKNMMGAKEISLMKPG  231
2D1D        VIAYDIFKNPELEKKG---YYVDSLDDLYKQADVISLHVPDVPANVHMINDKSIAEMKDG  228
              :  .:         :       ..*   ::..  *   *  .  .  :..   :   : *

PTDH        ALLVNPCRGSVVDEAAVLAALERGQLGGYAADVFEMEDWARAD------RPRLIDPALLA  283
1GDH        AIVVNTARGDLVDNELVVAALEAGRLAYAGFDVFAGEP--------------NINEGYYD  277
1PSD        SLLINASRGTVVDIPALCDALASKHLAGAAIDVFPTEP---------ATNSDPFTSPLCE  282
2D1D        VVIVNCSRGRLVDTDAVIRGLDSGKIFGFVMDTYEDEVGVFNKDWEGKEFPDKRLADLID  288
             :::*  .** :**    :  .*   ::   *.:   *

PTDH        HPNTLFTPHIGSAVRAVRLEIERCAAQNIIQVLAGARPINAANRLPKAEPAAC-------  336
1GDH        LPNTFLFPHIGSAATQAREDMAHQANDLIDALFGGADMSYALA---------------  320
1PSD        FDNVLLTPHIGGSTQEAQENIGLEVAGKLIKYSDNGSTLSAVNFPEVSLPLHGGRRLMHI  342
2D1D        RPNVLVTPHTAFYTTHAVRNMVVKAFNNNLKLINGEKPDSPVALNKNKF----------  337
             *.:.. **    .  .  ::  .  .    .

PTDH        -----------------------------------------------------------
1GDH        -----------------------------------------------------------
1PSD        HENRPGVLTALNKIFAEQGVNIAAQYLQTSAQMGYVVIDIEADEDVAEKALQAMKAIPGT  402
2D1D        -----------------------------------------------------------

PTDH        ------- (SEQ ID NO: 1)
1GDH        ------- (SEQ ID NO: 13)
1PSD        IRARLLY (SEQ ID NO: 14)                                      409
2D1D        ------- (SEQ ID NO: 15)
```

FIG. 1

D-Lactate Dehydrogenase     Phosphite Dehydrogenase

E175A, A176R + NADP

(A) PTDH Wild-Type Sequence

```
MLPKLVITHRVHDEILQLLAPHCELMTNQTDSTLTREEILRRCRDAQAMM        50
AFMPDRVDADFLQACPELRVVGCALKGFDNFDVDACTARGVWLTFVPDLL       100
TVPTAELAIGLAVGLGRHLRAADAFVRSGEFQGWQPQFYGTGLDNATVGI       150
LGMGAIGLAMADRLQGWGATLQYHEAKALDTQTEQRLGLRQVACSELFAS       200
SDFILLALPLNADTQHLVNAELLALVRPGALLVNPCRGSVVDEAAVLAAL       250
ERGQLGGYAADVFEMEDWARADRPRLIDPALLAHPNTLFTPHIGSAVRAV       300
RLEIERCAAQNIIQVLAGARPINAANRLPKAEPAAC (SEQ ID NO: 1)      336
```

(B) PTDH E175A Mutant

```
MLPKLVITHRVHDEILQLLAPHCELMTNQTDSTLTREEILRRCRDAQAMM        50
AFMPDRVDADFLQACPELRVVGCALKGFDNFDVDACTARGVWLTFVPDLL       100
TVPTAELAIGLAVGLGRHLRAADAFVRSGEFQGWQPQFYGTGLDNATVGI       150
LGMGAIGLAMADRLQGWGATLQYHAAKALDTQTEQRLGLRQVACSELFAS       200
SDFILLALPLNADTQHLVNAELLALVRPGALLVNPCRGSVVDEAAVLAAL       250
ERGQLGGYAADVFEMEDWARADRPRLIDPALLAHPNTLFTPHIGSAVRAV       300
RLEIERCAAQNIIQVLAGARPINAANRLPKAEPAAC (SEQ ID NO: 2)      336
```

(C) PTDH A176R Mutant

```
MLPKLVITHRVHDEILQLLAPHCELMTNQTDSTLTREEILRRCRDAQAMM        50
AFMPDRVDADFLQACPELRVVGCALKGFDNFDVDACTARGVWLTFVPDLL       100
TVPTAELAIGLAVGLGRHLRAADAFVRSGEFQGWQPQFYGTGLDNATVGI       150
LGMGAIGLAMADRLQGWGATLQYHERKALDTQTEQRLGLRQVACSELFAS       200
SDFILLALPLNADTQHLVNAELLALVRPGALLVNPCRGSVVDEAAVLAAL       250
ERGQLGGYAADVFEMEDWARADRPRLIDPALLAHPNTLFTPHIGSAVRAV       300
RLEIERCAAQNIIQVLAGARPINAANRLPKAEPAAC (SEQ ID NO: 3)      336
```

(D) PTDH E175A, A176R Mutant

```
MLPKLVITHRVHDEILQLLAPHCELMTNQTDSTLTREEILRRCRDAQAMM        50
AFMPDRVDADFLQACPELRVVGCALKGFDNFDVDACTARGVWLTFVPDLL       100
TVPTAELAIGLAVGLGRHLRAADAFVRSGEFQGWQPQFYGTGLDNATVGI       150
LGMGAIGLAMADRLQGWGATLQYHARKALDTQTEQRLGLRQVACSELFAS       200
SDFILLALPLNADTQHLVNAELLALVRPGALLVNPCRGSVVDEAAVLAAL       250
ERGQLGGYAADVFEMEDWARADRPRLIDPALLAHPNTLFTPHIGSAVRAV       300
RLEIERCAAQNIIQVLAGARPINAANRLPKAEPAAC (SEQ ID NO: 4)      336
```

FIG. 7

PTDH Parent (E175A-3B84)

```
  1  atgctgccgaaactcgttataactcaccgagtacacgaagagatcctgcaactgctggcg    60
     tacgacggctttgagcaatattgagtggctcatgtgcttctctaggacgttgacgaccgc
1     M  L  P  K  L  V  I  T  H  R  V  H  E  E  I  L  Q  L  L  A 61  ccacattgcgagctgataaccaaccagaccgacagcacgctgacgcgcgaggaaattctg   120
     ggtgtaacgctcgactattggttggtctggctgtcgtgcgactgcgcgctcctttaagac
21    P  H  C  E  L  I  T  N  Q  T  D  S  T  L  R  E  E  I  L 121  cgccgctgtcgcgatgctcaggcgatgatggcgttcatgcccgatcgggtcgatgcagac   180
     gcggcgacagcgctacgagtccgctactaccgcaagtacgggctagcccagctacgtctg
41    R  R  C  R  D  A  Q  A  M  M  A  F  M  P  D  R  V  D  A  D 181  tttcttcaagcctgccctgagctgcgtgtagtcggctgcgcgctcaagggcttcgacaat   240
     aaagaagttcggacgggactcgacgcacatcagccgacgcgcgagttcccgaagctgtta
61    F  L  Q  A  C  P  E  L  R  V  V  G  C  A  L  K  G  F  D  N 241  ttcgatgtggacgcctgtactgcccgcggggtctggctgaccttcgtgcctgatctgttg   300
     aagctacacctgcggacatgacgggcgccccagaccgactggaagcacggactagacaac
81    F  D  V  D  A  C  T  A  R  G  V  W  L  T  F  V  P  D  L  L 301  acggtcccgactgccgagctggcgatcggactggcggtggggctggggcggcatctgcgg   360
     tgccagggctgacggctcgaccgctagcctgaccgccaccccgacccgccgtagacgcc
101   T  V  P  T  A  E  L  A  I  G  L  A  V  G  L  G  R  H  L  R 361  gcagcagatgcgttcgtccgctctggcgagttccagggctggcaaccacagttctacggc   420
     cgtcgtctacgcaagcaggcgagaccgctcaaggtcccgaccgttggtgtcaagatgccg
121   A  A  D  A  F  V  R  S  G  E  F  Q  G  W  Q  P  Q  F  Y  G 421  acggggctggataacgctacggtcggcatccttggcatgggcgccatcggactggccatg   480
     tgccccgacctattgcgatgccagccgtaggaaccgtacccgcggtagcctgaccggtac
141   T  G  L  D  N  A  T  V  G  I  L  G  M  G  A  I  G  L  A  M 481  gctgatcgcttgcagggatggggcgcgaccctgcagtaccacgcggcgaaggctctggat   540
     cgactagcgaacgtccctaccccgcgctgggacgtcatggtgcgccgcttccgagaccta
161   A  D  R  L  Q  G  W  G  A  T  L  Q  Y  H  A  A  K  A  L  D
      541 acacaaaccgagcaacggctcggcctgcgccaggtggcgtgcagcgaactcttcgccagc   600
          tgtgtttggctcgttgccgagccggacgcggtccaccgcacgtcgcttgagaagcggtcg
181   T  Q  T  E  Q  R  L  G  L  R  Q  V  A  C  S  E  L  F  A  S 601  tcggacttcatcctgctggcgcttcccttgaatgccgatacccagcatctggtcaacgcc   660
```

FIG. 8A

```
             agcctgaagtaggacgaccgcgaagggaacttacggctatgggtcgtagaccagttgcgg
201          S  D  F  I  L  L  A  L  P  L  N  A  D  T  Q  H  L  V  N  A 661    gagctgcttgccctcgtacggccgggcgctctgcttgtaaaccccgtcgtggttcggta    720
             ctcgacgaacgggagcatgccggcccgcgagacgaacatttggggacagcaccaagccat
221          E  L  L  A  L  V  R  P  G  A  L  L  V  N  P  C  R  G  S  V 721    gtggatgaagccgccgtgctcgcggcgcttgagcgaggccagctcggcgggtatgcggcg    780
             cacctacttcggcggcacgagcgccgcgaactcgctccggtcgagccgcccatacgccgc
241          V  D  E  A  A  V  L  A  A  L  E  R  G  Q  L  G  G  Y  A  A 781    gatgtattcgaaatggaagactgggctcgcgcggaccggccgcggctgatcgatcctgcg    840
             ctacataagctttaccttctgacccgagcgcgcctggccggcgccgactagctaggacgc
261          D  V  F  E  M  E  D  W  A  R  A  D  R  P  R  L  I  D  P  A 841    ctgctcgcgcatccgaatacgctgttcactccgcacatagggtcggcagtgcgcgcggtg    900
             gacgagcgcgtaggcttatgcgacaagtgaggcgtgtatcccagccgtcacgcgcgccac
281          L  L  A  H  P  N  T  L  F  T  P  H  I  G  S  A  V  R  A  V 901    cgcctggagattgaacgttgtgcagcgcagaacatcatccaggtattggcaggtgcgcgc    960
             gcggacctctaacttgcaacacgtcgcgtcttgtagtaggtccataaccgtccacgcgcg
301          R  L  E  I  E  R  C  A  A  Q  N  I  I  Q  V  L  A  G  A  R 961    ccaatcaacgctgcgaaccgtctgcccaaggccaatcctgccgcagactga (SEQ ID NO: 26) 1017
             ggttagttgcgacgcttggcagacgggttccggttaggacggcgtctgact
321          P  I  N  A  A  N  R  L  P  K  A  N  P  A  A  D  *   (SEQ ID NO: 5)
```

FIG. 8B

PTDH Q132R Mutant

```
  1   atgctgccgaaactcgttataactcaccgagtacacgaagagatcctgcaactgctggcg   60
      tacgacggctttgagcaatattgagtggctcatgtgcttctctaggacgttgacgaccgc
  1    M   L   P   K   L   V   I   T   H   R   V   H   E   E   I   L   Q   L   L   A 61   ccacattgcgagctgataaccaaccagaccgacagcacgctgacgcgcgaggaaattctg   120
      ggtgtaacgctcgactattggttggtctggctgtcgtgcgactgcgcgctcctttaagac
 21    P   H   C   E   L   I   T   N   Q   T   D   S   T   L   R   E   E   I   L 121   cgccgctgtcgcgatgctcaggcgatgatggcgttcatgcccgatcgggtcgatgcagac   180
      gcggcgacagcgctacgagtccgctactaccgcaagtacgggctagcccagctacgtctg
 41    R   R   C   R   D   A   Q   A   M   M   A   F   M   P   D   R   V   D   A   D 181   tttcttcaagcctgccctgagctgcgtgtagtcggctgcgcgctcaagggcttcgacaat   240
      aaagaagttcggacgggactcgacgcacatcagccgacgcgcgagttcccgaagctgtta
 61    F   L   Q   A   C   P   E   L   R   V   V   G   C   A   L   K   G   F   D   N 241   ttcgatgtggacgcctgtactgcccgcggggtctggctgaccttcgtgcctgatctgttg   300
      aagctacacctgcggacatgacgggcgcccagaccgactggaagcacggactagacaac
 81    F   D   V   D   A   C   T   A   R   G   V   W   L   T   F   V   P   D   L   L 301   acggtcccgactgccgagctggcgatcggactggcggtggggctggggcggcatctgcgg   360
      tgccagggctgacggctcgaccgctagcctgaccgccaccccgaccccgccgtagacgcc
101    T   V   P   T   A   E   L   A   I   G   L   A   V   G   L   G   R   H   L   R 361   gcagcagatgcgttcgtccgctctggcgagttccggggctggcaaccacagttctacggc   420
      cgtcgtctacgcaagcaggcgagaccgctcaaggcccgaccgttggtgtcaagatgccg
121    A   A   D   A   F   V   R   S   E   F   R   G   W   Q   P   Q   F   Y   G 421   acggggctggataacgctacggtcggcatccttggcatgggcgccatcggactggccatg   480
      tgccccgacctattgcgatgccagccgtaggaaccgtacccgcggtagcctgaccggtac
141    T   G   L   D   N   A   T   V   G   I   L   G   M   G   A   I   G   L   A   M 481   gctgatcgcttgcagggatggggcgcgaccctgcagtaccacgcggcgaaggctctggat   540
      cgactagcgaacgtccctaccccgcgctgggacgtcatggtgcgccgcttccgagaccta
161    A   D   R   L   Q   G   W   G   A   T   L   Q   Y   H   A   A   K   A   L   D
181
541   acacaaaccgagcaacggctcggcctgcgccaggtggcgtgcagcgaactcttcgccagc   600
      tgtgtttggctcgttgccgagccggacgcggtccaccgcacgtcgcttgagaagcggtcg
181    T   Q   T   E   Q   R   L   G   L   R   Q   V   A   C   S   E   L   F   A   S 601   tcggacttcatcctgctggcgcttcccttgaatgccgatacccagcatctggtcaacgcc   660
      agcctgaagtaggacgaccgcgaagggaacttacggctatgggtcgtagaccagttgcgg
```

FIG. 9A

201      S  D  F  I  L  L  A  L  P  L  N  A  D  T  Q  H  L  V  N  A 661  gagctgcttgccctcgtacggccgggcgctctgcttgtaaacccctgtcgtggttcggta    720
          ctcgacgaacgggagcatgccggcccgcgagacgaacatttggggacagcaccaagccat

221      E  L  L  A  L  V  R  P  G  A  L  L  V  N  P  C  R  G  S  V 721  gtggatgaagccgccgtgctcgcggcgcttgagcgaggccagctcggcgggtatgcggcg    780
          cacctacttcggcggcacgagcgccgcgaactcgctccggtcgagccgcccatacgccgc

241      V  D  E  A  A  V  L  A  A  L  E  R  G  Q  L  G  G  Y  A  A 781  gatgtattcgaaatggaagactgggctcgcgcggaccggccgcggctgatcgatcctgcg    840
          ctacataagctttaccttctgacccgagcgcgcctggccggcgccgactagctaggacgc

261      D  V  F  E  M  E  D  W  A  R  A  D  R  P  R  L  I  D  P  A 841  ctgctcgcgcatccgaatacgctgttcactccgcatagggtcggcagtgcgcgcggtg     900
          gacgagcgcgtaggcttatgcgacaagtgaggcgtgtatcccagccgtcacgcgcgccac

281      L  L  A  H  P  N  T  L  F  T  P  H  I  G  S  A  V  R  A  V 901  cgcctggagattgaacgttgtgcagcgcagaacatcatccaggtattggcaggtgcgcgc    960
          gcggacctctaacttgcaacacgtcgcgtcttgtagtaggtccataaccgtccacgcgcg

301      R  L  E  I  E  R  C  A  A  Q  N  I  I  Q  V  L  A  G  A  R 961  ccaatcaacgctgcgaaccgtctgcccaaggccaatcctgccgcagactga (SEQ ID NO: 27) 1017
          ggttagttgcgacgcttggcagacgggttccggttaggacggcgtctgact

321      P  I  N  A  A  N  R  L  P  K  A  N  P  A  A  D  *   (SEQ ID NO: 6)

FIG. 9B

PTDH Q137R Mutant

```
  1  atgctgccgaaactcgttataactcaccgagtacacgaagagatcctgcaactgctggcg   60
     tacgacggctttgagcaatattgagtggctcatgtgcttctctaggacgttgacgaccgc 1    M   L   P   K   L   V   I   T   H   R   V   H   E   E   I   L   Q   L   L   A
```

```
 61  ccacattgcgagctgataaccaaccagaccgacagcacgctgacgcgcgaggaaattctg  120
     ggtgtaacgctcgactattggttggtctggctgtcgtgcgactgcgcgctcctttaagac 21    P   H   C   E   L   I   T   N   Q   T   D   S   T   L   T   R   E   E   I   L
```

```
121  cgccgctgtcgcgatgctcaggcgatgatggcgttcatgcccgatcgggtcgatgcagac  180
     gcggcgacagcgctacgagtccgctactaccgcaagtacgggctagcccagctacgtctg 41    R   R   C   R   D   A   Q   A   M   M   A   F   M   P   D   R   V   D   A   D
```

```
181  tttcttcaagcctgccctgagctgcgtgtagtcggctgcgcgctcaagggcttcgacaat  240
     aaagaagttcggacgggactcgacgcacatcagccgacgcgcgagttcccgaagctgtta 61    F   L   Q   A   C   P   E   L   R   V   V   G   C   A   L   K   G   F   D   N
```

```
241  ttcgatgtggacgcctgtactgcccgcggggtctggctgaccttcgtgcctgatctgttg  300
     aagctacacctgcggacatgacgggcgccccagaccgactggaagcacggactagacaac 81    F   D   V   D   A   C   T   A   R   G   V   W   L   T   F   V   P   D   L   L
```

```
301  acggtcccgactgccgagctggcgatcggactggcggtggggctggggcggcatctgcgg  360
     tgccagggctgacggctcgaccgctagcctgaccgccaccccgaccccgccgtagacgcc 101    T   V   P   T   A   E   L   A   I   G   L   A   V   G   L   G   R   H   L   R
```

```
361  gcagcagatgcgttcgtccgctctggcgagttccagggctggcaaccacggttctacggc  420
     cgtcgtctacgcaagcaggcgagaccgctcaaggtcccgaccgttggtgccaagatgccg 121    A   A   D   A   F   V   R   S   G   E   F   Q   G   W   Q   P   R   F   Y   G
```

```
421  acggggctggataacgctacggtcggcatccttggcatgggcgccatcggactggccatg  480
     tgccccgacctattgcgatgccagccgtaggaaccgtacccgcggtagcctgaccggtac 141    T   G   L   D   N   A   T   V   G   I   L   G   M   G   A   I   G   L   A   M
```

```
481  gctgatcgcttgcagggatggggcgcgaccctgcagtaccacgcggcgaaggctctggat  540
     cgactagcgaacgtcctacccgcgctgggacgtcatggtgcgccgcttccgagaccta 161    A   D   R   L   Q   G   W   G   A   T   L   Q   Y   H   A   A   K   A   L   D
```

```
541  acacaaaccgagcaacggctcggcctgcgccaggtggcgtgcagcgaactcttcgccagc  600
     tgtgtttggctcgttgccgagccggacgcggtccaccgcacgtcgcttgaagaagcggtcg 181    T   Q   T   E   Q   R   L   G   L   R   Q   V   A   C   S   E   L   F   A   S
```

```
601  tcggacttcatcctgctggcgcttcccttgaatgccgatacccagcatctggtcaacgcc  660
```

FIG. 10A

```
        agcctgaagtaggacgaccgcgaagggaacttacggctatgggtcgtagaccagttgcgg
201     S   D   F   I   L   L   A   L   P   L   N   A   D   T   Q   H   L   V   N   A 661 gagctgcttgccctcgtacggccgggcgctctgcttgtaaaccnnctgtcgtggttcggta              720
        ctcgacgaacgggagcatgccggcccgcgagacgaacatttggggacagcaccaagccat
221     E   L   L   A   L   V   R   P   G   A   L   L   V   N   P   C   R   G   S   V 721 gtggatgaagccgccgtgctcgcggcgcttgagcgaggccagctcggcgggtatgcggcg              780
        cacctacttcggcggcacgagcgccgcgaactcgctccggtcgagccgcccatacgccgc
241     V   D   E   A   A   V   L   A   A   L   E   R   G   Q   L   G   G   Y   A   A 781 gatgtattcgaaatggaagactgggctcgcgcggaccggccgcggctgatcgatcctgcg              840
        ctacataagctttaccttctgacccgagcgcgcctggccggcgccgactagctaggacgc
261     D   V   F   E   M   E   D   W   A   R   A   D   R   P   R   L   I   D   P   A 841 ctgctcgcgcatccgaatacgctgttcactccgcacatagggtcggcagtgcgcgcggtg              900
        gacgagcgcgtaggcttatgcgacaagtgaggcgtgtatcccagccgtcacgcgcgccac
281     L   L   A   H   P   N   T   L   F   T   P   H   I   G   S   A   V   R   A   V 901 cgcctggagattgaacgttgtgcagcgcagaacatcatccaggtattggcaggtgcgcgc              960
        gcggacctctaacttgcaacacgtcgcgtcttgtagtaggtccataaccgtccacgcgcg
301     R   L   E   I   E   R   C   A   A   Q   N   I   I   Q   V   L   A   G   A   R 961 ccaatcaacgctgcgaaccgtctgcccaaggccaatcctgccgcagactga (SEQ ID NO: 28) 1017
        ggttagttgcgacgcttggcagacgggttccggttaggacggcgtctgact
321     P   I   N   A   A   N   R   L   P   K   A   N   P   A   A   D   *   (SEQ ID NO: 7)
```

FIG. 10B

PTDH I150F Mutant

```
  1   atgctgccgaaactcgttataactcaccgagtacacgaagagatcctgcaactgctggcg   60
      tacgacggctttgagcaatattgagtggctcatgtgcttctctaggacgttgacgaccgc
  1   M   L   P   K   L   V   I   T   H   R   V   H   E   E   I   L   Q   L   L   A 61   ccacattgcgagctgataaccaaccagaccgacagcacgctgacgcgcgaggaaattctg  120
      ggtgtaacgctcgactattggttggtctggctgtcgtgcgactgcgcgctcctttaagac
 21   P   H   C   E   L   I   T   N   Q   T   D   S   T   L   T   R   E   E   I   L 121   cgccgctgtcgcgatgctcaggcgatgatggcgttcatgcccgatcgggtcgatgcagac  180
      gcggcgacagcgctacgagtccgctactaccgcaagtacgggctagcccagctacgtctg
 41   R   R   C   R   D   A   Q   A   M   M   A   F   M   P   D   R   V   D   A   D 181   tttcttcaagcctgccctgagctgcgtgtagtcggctgcgcgctcaagggcttcgacaat  240
      aaagaagttcggacgggactcgacgcacatcagccgacgcgcgagttcccgaagctgtta
 61   F   L   Q   A   C   P   E   L   R   V   V   G   C   A   L   K   G   F   D   N 241   ttcgatgtggacgcctgtactgcccgcggggtctggctgaccttcgtgcctgatctgttg  300
      aagctacacctgcggacatgacgggcgccccagaccgactggaagcacggactagacaac
 81   F   D   V   D   A   C   T   A   R   G   V   W   L   T   F   V   P   D   L   L 301   acggtcccgactgccgagctggcgatcggactggcggtggggctggggcggcatctgcgg  360
      tgccagggctgacggctcgaccgctagcctgaccgccaccccgaccccgccgtagacgcc
101   T   V   P   T   A   E   L   A   I   G   L   A   V   G   L   G   R   H   L   R 361   gcagcagatgcgttcgtccgctctggcgagttccagggctggcaaccacagttctacggc  420
      cgtcgtctacgcaagcaggcgagaccgctcaaggtcccgaccgttggtgtcaagatgccg
121   A   A   D   A   F   V   R   S   G   E   F   Q   G   W   Q   P   Q   F   Y   G 421   acggggctggataacgctacggtcggcttccttggcatgggcgccatcggactggccatg  480
      tgccccgacctattgcgatgccagccgaaggaaccgtacccgcggtagcctgaccggtac
141   T   G   L   D   N   A   T   V   G   F   L   G   M   G   A   I   G   L   A   M 481   gctgatcgcttgcagggatggggcgcgaccctgcagtaccacgcggcgaaggctctggat  540
      cgactagcgaacgtccctacccgcgctgggacgtcatggtgcgccgcttccgagaccta
161   A   D   R   L   Q   G   W   G   A   T   L   Q   Y   H   A   A   K   A   L   D 541   acacaaaccgagcaacggctcggcctgcgccaggtggcgtgcagcgaactcttcgccagc  600
      tgtgtttggctcgttgccgagccggacgcggtccaccgcacgtcgcttgaagaagcggtcg
181   T   Q   T   E   Q   R   L   G   L   R   Q   V   A   C   S   E   L   F   A   S 601   tcggacttcatcctgctggcgcttcccttgaatgccgataccagcatctggtcaacgcc   660
      agcctgaagtaggacgaccgcgaagggaacttacggctatgggtcgtagaccagttgcgg
```

FIG. 11A

```
201        S  D  F  I  L  L  A  L  P  L  N  A  D  T  Q  H  L  V  N  A 661   gagctgcttgccctcgtacggccgggcgctctgcttgtaaaccccctgtcgtggttcggta   720
           ctcgacgaacgggagcatgccggcccgcgagacgaacatttggggacagcaccaagccat

221        E  L  L  A  L  V  R  P  G  A  L  L  V  N  P  C  R  G  S  V 721   gtggatgaagccgccgtgctcgcggcgcttgagcgaggccagctcggcgggtatgcggcg   780
           cacctacttcggcggcacgagcgccgcgaactcgctccggtcgagccgcccatacgccgc

241        V  D  E  A  A  V  L  A  A  L  E  R  G  Q  L  G  G  Y  A  A 781   gatgtattcgaaatggaagactgggctcgcgcggaccggccgcggctgatcgatcctgcg   840
           ctacataagcttaccttctgacccgagcgcgcctggccggcgccgactagctaggacgc

261        D  V  F  E  M  E  D  W  A  R  A  D  R  P  R  L  I  D  P  A 841   ctgctcgcgcatccgaatacgctgttcactccgcacatagggtcggcagtgcgcgcggtg   900
           gacgagcgcgtaggcttatgcgacaagtgaggcgtgtatcccagccgtcacgcgcgccac

281        L  L  A  H  P  N  T  L  F  T  P  H  I  G  S  A  V  R  A  V 901   cgcctggagattgaacgttgtgcagcgcagaacatcatccaggtattggcaggtgcgcgc   960
           gcggacctctaacttgcaacacgtcgcgtcttgtagtaggtccataaccgtccacgcgcg

301        R  L  E  I  E  R  C  A  A  Q  N  I  I  Q  V  L  A  G  A  R 961   ccaatcaacgctgcgaaccgtctgcccaaggccaatcctgccgcagactga (SEQ ID NO: 29) 1017
           ggttagttgcgacgcttggcagacgggttccggttaggacggcgtctgact 321        P  I  N  A  A  N  R  L  P  K  A  N  P  A  A  D  *  (SEQ ID NO: 8)
```

FIG. 11B

PTDH Q215L Mutant

```
  1   atgctgccgaaactcgttataactcaccgagtacacgaagagatcctgcaactgctggcg    60
      tacgacggctttgagcaatattgagtggctcatgtgcttctctaggacgttgacgaccgc
  1    M  L  P  K  L  V  I  T  H  R  V  H  E  E  I  L  Q  L  L  A 61  ccacattgcgagctgataaccaaccagaccgacagcacgctgacgcgcgaggaaattctg   120
      ggtgtaacgctcgactattggttggtctggctgtcgtgcgactgcgcgctcctttaagac
 21    P  H  C  E  L  I  T  N  Q  T  D  S  T  L  T  R  E  E  I  L 121  cgccgctgtcgcgatgctcaggcgatgatggcgttcatgcccgatcgggtcgatgcagac   180
      gcggcgacagcgctacgagtccgctactaccgcaagtacgggctagcccagctacgtctg
 41    R  R  C  R  D  A  Q  A  M  M  A  F  M  P  D  R  V  D  A  D 181  tttcttcaagcctgccctgagctgcgtgtagtcggctgcgcgctcaagggcttcgacaat   240
      aaagaagttcggacgggactcgacgcacatcagccgacgcgcgagttcccgaagctgtta
 61    F  L  Q  A  C  P  E  L  R  V  V  G  C  A  L  K  G  F  D  N 241  ttcgatgtggacgcctgtactgcccgcggggtctggctgaccttcgtgcctgatctgttg   300
      aagctacacctgcggacatgacgggcgccccagaccgactggaagcacggactagacaac
 81    F  D  V  D  A  C  T  A  R  G  V  W  L  T  F  V  P  D  L  L 301  acggtcccgactgccgagctggcgatcggactggcggtggggctggggcggcatctgcgg   360
      tgccagggctgacggctcgaccgctagcctgaccgccaccccgaccccgcgtagacgcc
101    T  V  P  T  A  E  L  A  I  G  L  A  V  G  L  G  R  H  L  R 361  gcagcagatgcgttcgtccgctctggcgagttccagggctggcaaccacagttctacggc   420
      cgtcgtctacgcaagcaggcgagaccgctcaaggtcccgaccgttggtgtcaagatgccg
121    A  A  D  A  F  V  R  S  G  E  F  Q  G  W  Q  P  Q  F  Y  G 421  acggggctggataacgctacggtcggcatccttggcatgggcgccatcggactggccatg   480
      tgccccgacctattgcgatgccagccgtaggaaccgtaccgcggtagcctgaccggtac
141    T  G  L  D  N  A  T  V  G  I  L  G  M  G  A  I  G  L  A  M 481  gctgatcgcttgcagggatggggcgcgaccctgcagtaccacgcggcgaaggctctggat   540
      cgactagcgaacgtccctaccccgcgctgggacgtcatggtgcgccgcttccgagaccta
161    A  D  R  L  Q  G  W  G  A  T  L  Q  Y  H  A  A  K  A  L  D 541  acacaaaccgagcaacggctcggcctgcgccaggtggcgtgcagcgaactcttcgccagc   600
      tgtgtttggctcgttgccgagccggacgcggtccaccgcacgtcgcttgagaagcggtcg
181    T  Q  T  E  Q  R  L  G  L  R  Q  V  A  C  S  E  L  F  A  S 601  tcggacttcatcctgctggcgcttcccttgaatgccgataccctgcatctggtcaacgcc   660
```

FIG. 12A

```
            agcctgaagtaggacgaccgcgaagggaacttacggctatgggacgtagaccagttgcgg
201         S   D   F   I   L   L   A   L   P   L   N   A   D   T   T   H   L   V   N   A 661     gagctgcttgccctcgtacggccgggcgctctgcttgtaaaccsctgtcgtggttcggta     720
            ctcgacgaacgggagcatgccggcccgcgagacgaacatttggggacagcaccaagccat
221         E   L   L   A   L   V   R   P   G   A   L   L   V   N   P   C   R   G   S   V 721     gtggatgaagccgccgtgctcgcggcgcttgagcgaggccagctcggcgggtatgcggcg     780
            cacctacttcggcggcacgagcgccgcgaactcgctccggtcgagccgcccatacgccgc
241         V   D   E   A   A   V   L   A   A   L   E   R   G   Q   L   G   G   Y   A   A 781     gatgtattcgaaatggaagactgggctcgcgcggaccggccgcggctgatcgatcctgcg     840
            ctacataagctttaccttctgacccgagcgcgcctggccggcgccgactagctaggacgc
261         D   V   F   E   M   E   D   W   A   R   A   D   R   P   R   L   I   D   P   A 841     ctgctcgcgcatccgaatacgctgttcactccgcacatagggtcggcagtgcgcgcggtg     900
            gacgagcgcgtaggcttatgcgacaagtgaggcgtgtatcccagccgtcacgcgcgccac
281         L   L   A   H   P   N   T   L   F   T   P   H   I   G   S   A   V   R   A   V 901     cgcctggagattgaacgttgtgcagcgcagaacatcatccaggtattggcaggtgcgcgc     960
            gcggacctctaacttgcaacacgtcgcgtcttgtagtaggtccataaccgtccacgcgcg
301         R   L   E   I   E   R   C   A   A   Q   N   I   I   Q   V   L   A   G   A   R 961     ccaatcaacgctgcgaaccgtctgcccaaggccaatcctgccgcagactga (SEQ ID NO: 30) 1017
            ggttagttgcgacgcttggcagacgggttccggttaggacggcgtctgact
321         P   I   N   A   A   N   R   L   P   K   A   N   P   A   A   D   *   (SEQ ID NO: 9)
```

FIG. 12B

PTDH R275Q Mutant

```
  1  atgctgccgaaactcgttataactcaccgagtacacgaagagatcctgcaactgctggcg    60
     tacgacggctttgagcaatattgagtggctcatgtgcttctctaggacgttgacgaccgc
  1   M  L  P  K  L  V  I  T  H  R  V  H  E  E  I  L  Q  L  L  A 61  ccacattgcgagctgataaccaaccagaccgacagcacgctgacgcgcgaggaaattctg   120
     ggtgtaacgctcgactattggttggtctggctgtcgtgcgactgcgcgctcctttaagac
 21   P  H  C  E  L  I  T  N  Q  T  D  S  T  L  T  R  E  E  I  L 121  cgccgctgtcgcgatgctcaggcgatgatggcgttcatgcccgatcgggtcgatgcagac   180
     gcggcgacagcgctacgagtccgctactaccgcaagtacgggctagcccagctacgtctg
 41   R  R  C  R  D  A  Q  A  M  M  A  F  M  P  D  R  V  D  A  D 181  tttcttcaagcctgccctgagctgcgtgtagtcggctgcgcgctcaagggcttcgacaat   240
     aaagaagttcggacgggactcgacgcacatcagccgacgcgcgagttcccgaagctgtta
 61   F  L  Q  A  C  P  E  L  R  V  V  G  C  A  L  K  G  F  D  N 241  ttcgatgtggacgcctgtactgcccgcggggtctggctgaccttcgtgcctgatctgttg   300
     aagctacacctgcggacatgacgggcgccccagaccgactggaagcacggactagacaac
 81   F  D  V  D  A  C  T  A  R  G  V  W  L  T  F  V  P  D  L  L 301  acggtcccgactgccgagctggcgatcggactggcggtggggctggggcggcatctgcgg   360
     tgccagggctgacggctcgaccgctagcctgaccgccaccccgaccccgccgtagacgcc
101   T  V  P  T  A  E  L  A  I  G  L  A  V  G  L  G  R  H  L  R 361  gcagcagatgcgttcgtccgctctggcgagttccagggctggcaaccacagttctacggc   420
     cgtcgtctacgcaagcaggcgagaccgctcaaggtcccgaccgttggtgtcaagatgccg
121   A  A  D  A  F  V  R  S  G  E  F  Q  G  W  Q  P  Q  F  Y  G 421  acggggctggataacgctacggtcggcatccttggcatgggcgccatcggactggccatg   480
     tgccccgacctattgcgatgccagccgtaggaaccgtacccgcggtagcctgaccggtac
141   T  G  L  D  N  A  T  V  G  I  L  G  M  G  A  I  G  L  A  M 481  gctgatcgcttgcagggatggggcgcgaccctgcagtaccacgcggcgaaggctctggat   540
     cgactagcgaacgtcctaccccgcgctgggacgtcatggtgcgccgcttccgagaccta
161   A  D  R  L  Q  G  W  G  A  T  L  Q  Y  H  A  A  K  A  L  D 541  acacaaaccgagcaacggctcggcctgcgccaggtggcgtgcagcgaactcttcgccagc   600
     tgtgtttggctcgttgccgagccggacgcggtccaccgcacgtcgcttgagaagcggtcg
181   T  Q  T  E  Q  R  L  G  L  R  Q  V  A  C  S  E  L  F  A  S 601  tcggacttcatcctgctggcgcttcccttgaatgccgatacccagcatctggtcaacgcc   660
```

FIG. 13A

```
            agcctgaagtaggacgaccgcgaagggaacttacggctatgggtcgtagaccagttgcgg
201         S  D  F  I  L  L  A  L  P  L  N  A  D  T  Q  H  L  V  N  A 661   gagctgcttgccctcgtacggccgggcgctctgcttgtaaacccctgtcgtggttcggta   720
            ctcgacgaacgggagcatgccggcccgcgagacgaacatttggggacagcaccaagccat
221         E  L  L  A  L  V  R  P  G  A  L  L  V  N  P  C  R  G  S  V 721   gtggatgaagccgccgtgctcgcggcgcttgagcgaggccagctcggcgggtatgcggcg   780
            cacctacttcggcggcacgagcgccgcgaactcgctccggtcgagccgcccatacgccgc
241         V  D  E  A  A  V  L  A  A  L  E  R  G  Q  L  G  G  Y  A  A 781   gatgtattcgaaatggaagactgggctcgcgcggaccggccgcagctgatcgatcctgcg   840
            ctacataagctttaccttctgaccccgagcgcgcctggccggcgtcgactagctaggacgc
261         D  V  F  E  M  E  D  W  A  R  A  D  R  P  Q  L  I  D  P  A 841   ctgctcgcgcatccgaatacgctgttcactccgcacatagggtcggcagtgcgcgcggtg   900
            gacgagcgcgtaggcttatgcgacaagtgaggcgtgtatcccagccgtcacgcgcgccac
281         L  L  A  H  P  N  T  L  F  T  P  H  I  G  S  A  V  R  A  V 901   cgcctggagattgaacgttgtgcagcgcagaacatcatccaggtattggcaggtgcgcgc   960
            gcggacctctaacttgcaacacgtcgcgtcttgtagtaggtccataaccgtccacgcgcg
301         R  L  E  I  E  R  C  A  A  Q  N  I  I  Q  V  L  A  G  A  R 961   ccaatcaacgctgcgaaccgtctgcccaaggccaatcctgccgcagactga (SEQ ID NO: 31) 1017
            ggttagttgcgacgcttggcagacgggttccggttaggacggcgtctgact
321         P  I  N  A  A  N  R  L  P  K  A  N  P  A  A  D  *   (SEQ ID NO: 10)
```

FIG. 13B

PTDH 4x Mutant

```
  1   atgctgccgaaactcgttataactcaccgagtacacgaagagatcctgcaactgctggcg   60
      tacgacggctttgagcaatattgagtggctcatgtgcttctctaggacgttgacgaccgc
  1    M  L  P  K  L  V  I  T  H  R  V  H  E  E  I  L  Q  L  L  A 61   ccacattgcgagctgataaccaaccagaccgacagcacgctgacgcgcgaggaaattctg  120
      ggtgtaacgctcgactattggttggtctggctgtcgtgcgactgcgcgctcctttaagac
 21    P  H  C  E  L  I  T  N  Q  T  D  S  T  L  T  R  E  E  I  L 121   cgccgctgtcgcgatgctcaggcgatgatggcgttcatgcccgatcgggtcgatgcagac  180
      gcggcgacagcgctacgagtccgctactaccgcaagtacgggctagcccagctacgtctg
 41    R  R  C  R  D  A  Q  A  M  M  A  F  M  P  D  R  V  D  A  D 181   tttcttcaagcctgccctgagctgcgtgtagtcggctgcgcgctcaagggcttcgacaat  240
      aaagaagttcggacgggactcgacgcacatcagccgacgcgcgagttcccgaagctgtta
 61    F  L  Q  A  C  P  E  L  R  V  V  G  C  A  L  K  G  F  D  N 241   ttcgatgtggacgcctgtactgcccgcggggtctggctgaccttcgtgcctgatctgttg  300
      aagctacacctgcggacatgacgggcgccccagaccgactggaagcacggactagacaac
 81    F  D  V  D  A  C  T  A  R  G  V  W  L  T  F  V  P  D  L  L 301   acggtcccgactgccgagctggcgatcggactggcggtggggctggggcggcatctgcgg  360
      tgccagggctgacggctcgaccgctagcctgacgccaccccgaccccgccgtagacgcc
101    T  V  P  T  A  E  L  A  I  G  L  A  V  G  L  G  R  H  L  R 361   gcagcagatgcgttcgtccgctctggcgagttccagggctggcaaccacgggttctacggc  420
      cgtcgtctacgcaagcaggcgagaccgctcaaggtcccgaccgttggtgccaagatgccg
121    A  A  D  A  F  V  R  S  G  E  F  Q  G  W  Q  P  R  F  Y  G 421   acggggctggataacgctacggtcggcttccttggcatgggcgccatcggactggccatg  480
      tgccccgacctattgcgatgccagccgaaggaaccgtacccgcggtagcctgaccggtac
141    T  G  L  D  N  A  T  V  G  E  L  G  M  G  A  I  G  L  A  M 481   gctgatcgcttgcagggatggggcgcgaccctgcagtaccacgcggcgaaggctctggat  540
      cgactagcgaacgtccctaccccgcgctgggacgtcatggtgcgccgcttccgagaccta
161    A  D  R  L  Q  G  W  G  A  T  L  Q  Y  H  A  A  K  A  L  D 541   acacaaaccgagcaacggctcggcctgcgccaggtggcgtgcagcgaactcttcgccagc  600
      tgtgtttggctcgttgccgagccggacgcggtccaccgcacgtcgcttgaagaagcggtcg
181    T  Q  T  E  Q  R  L  G  L  R  Q  V  A  C  S  E  L  F  A  S
```

FIG. 14A

```
601  tcggacttcatcctgctggcgcttcccttgaatgccgataccctgcatctggtcaacgcc  660
     agcctgaagtaggacgaccgcgaagggaacttacggctatgggacgtagaccagttgcgg
201   S   D   F   I   L   L   A   L   P   L   N   A   D   T   L   H   L   V   N   A 661  gagctgcttgccctcgtacggccgggcgctctgcttgtaaacccctgtcgtgggtcggta  720
     ctcgacgaacgggagcatgccggcccgcgagacgaacattTggggacagcaccgagccat
221   E   L   L   A   L   V   R   P   G   A   L   L   V   N   P   C   R   G   S   V 721  gtggatgaagccgccgtgctcgcggcgcttgagcgaggccagctcggcgggtatgcggcg  780
     cacctacttcggcggcacgagcgccgcgaactcgctccggtcgagccgcccatacgccgc
241   V   D   E   A   A   V   L   A   A   L   E   R   G   Q   L   G   G   Y   A   A 781  gatgtattcgaaatggaagactgggctcgcgcggaccggccgcagctgatcgatcctgcg  840
     ctacataagctttaccttctgacccgagcgcgcctggccggcgtcgactagctaggacgc
261   D   V   F   E   M   E   D   W   A   R   A   D   R   P   Q   L   I   D   P   A 841  ctgctcgcgcatccgaatacgctgttcactccgcacatagggtcggcagtgcgcgcggtg  900
     gacgagcgcgtaggcttatgcgacaagtgaggcgtgtatcccagccgtcacgcgcgccac
281   L   L   A   H   P   N   T   L   F   T   P   H   I   G   S   A   V   R   A   V 901  cgcctggagattgaacgttgtgcagcgcagaacatcatccaggtattggcaggtgcgcgc  960
     gcggacctctaacttgcaacacgtcgcgtcttgtagtaggtccataaccgtccacgcgcg
301   R   L   E   I   E   R   C   A   A   Q   N   I   I   Q   V   L   A   G   A   R 961  ccaatcaacgctgcgaaccgtctgcccaaggccaatcctgccgcagactga (SEQ ID NO: 32) 1017
     ggttagttgcgacgcttggcagacgggttccggttaggacggcgtctgact
321   P   I   N   A   A   N   R   L   P   K   A   N   P   A   A   D   *   (SEQ ID NO: 11)
```

FIG. 14B

PTDH 5x Mutant

```
  1    atgctgccgaaactcgttataactcaccgagtacacgaagagatcctgcaactgctggcg      60
       tacgacggctttgagcaatattgagtggctcatgtgcttctctaggacgttgacgaccgc 1    M   L   P   K   L   V   I   T   H   R   V   H   E   E   I   L   Q   L   L   A 61   ccacattgcgagctgataaccaaccagaccgacagcacgctgacgcgcgaggaaattctg    120
       ggtgtaacgctcgactattggttggtctggctgtcgtgcgactgcgcgctcctttaagac 21    P   H   C   E   L   I   T   N   Q   T   D   S   T   L   T   R   E   E   I   L 121   cgccgctgtcgcgatgctcaggcgatgatggcgttcatgcccgatcgggtcgatgcagac    180
       gcggcgacagcgctacgagtccgctactaccgcaagtacgggctagcccagctacgtctg 41    R   R   C   R   D   A   Q   A   M   M   A   F   M   P   D   R   V   D   A   D 181   tttcttcaagcctgccctgagctgcgtgtagtcggctgcgcgctcaagggcttcgacaat    240
       aaagaagttcggacgggactcgacgcacatcagccgacgcgcgagttcccgaagctgtta 61    F   L   Q   A   C   P   E   L   R   V   V   G   C   A   L   K   G   F   D   N 241   ttcgatgtggacgcctgtactgcccgcggggtctggctgaccttcgtgcctgatctgttg    300
       aagctacacctgcggacatgacgggcgccccagaccgactggaagcacggactagacaac 81    F   D   V   D   A   C   T   A   R   G   V   W   L   T   F   V   P   D   L   L 301   acggtcccgactgccgagctggcgatcggactggcggtggggctggggcggcatctgcgg    360
       tgccagggctgacggctcgaccgctagcctgaccgccaccccgaccccgccgtagacgcc 101    T   V   P   T   A   E   L   A   I   G   L   A   V   G   L   G   R   H   L   R 361    gcagcagatgcgttcgtccgctctggcgagttccggggctggcaaccacggttctacggc    420
       cgtcgtctacgcaagcaggcgagaccgctcaaggccccgaccgttggtgccaagatgccg 121    A   A   D   A   F   V   R   S   G   E   F   R   G   W   Q   P   R   F   Y   G 421    acggggctggataacgctacggtcggctccttggcatgggcgccatcggactggccatg    480
       tgccccgacctattgcgatgccagccgaaggaaccgtacccgcggtagcctgaccggtac 141    T   G   L   D   N   A   T   V   G   E   L   G   M   G   A   I   G   L   A   M 481    gctgatcgcttgcagggatggggcgcgaccctgcagtaccacgcggcgaaggctctggat    540
       cgactagcgaacgtcccctaccccgcgctgggacgtcatggtgcgccgcttccgagaccta 161    A   D   R   L   Q   G   W   G   A   T   L   Q   Y   H   A   A   K   A   L   D 541    acacaaaccgagcaacggctcggcctgcgccaggtggcgtgcagcgaactcttcgccagc    600
       tgtgttggctcgttgccgagccggacgcggtccaccgcacgtcgcttgagaagcggtcg 181    T   Q   T   E   Q   R   L   G   L   R   Q   V   A   C   S   E   L   F   A   S
```

FIG. 15A

```
601  tcggacttcatcctgctggcgcttcccttgaatgccgatacctgcatctggtcaacgcc  660
     agcctgaagtaggacgaccgcgaagggaacttacggctatgggacgtagaccagttgcgg
201   S   D   F   I   L   L   A   L   P   L   N   A   D   T   L   H   L   V   N   A 661  gagctgcttgccctcgtacggccgggcgctctgcttgtaaaccccctgtcgtggttcggta  720
     ctcgacgaacgggagcatgccggcccgcgagacgaacatttggggacagcaccaagccat
221   E   L   L   A   L   V   R   P   G   A   L   L   V   N   P   C   R   G   S   V 721  gtggatgaagccgccgtgctcgcggcgcttgagcgaggccagctcggcgggtatgcggcg  780
     cacctacttcggcggcacgagcgccgcgaactcgctccggtcgagccgcccatacgccgc
241   V   D   E   A   A   V   L   A   A   L   E   R   G   Q   L   G   G   Y   A   A 781  gatgtattcgaaatggaagactgggctcgcgcggaccggccgcagctgatcgatcctgcg  840
     ctacataagctttaccttctgacccgagcgcgcctggccggcgtcgactagctaggacgc
261   D   V   F   E   M   E   D   W   A   R   A   D   R   P   Q   L   I   D   P   A 841  ctgctcgcgcatccgaatacgctgttcactccgcacatagggtcggcagtgcgcgcggtg  900
     gacgagcgcgtaggcttatgcgacaagtgaggcgtgtatcccagccgtcacgcgcgccac
281   L   L   A   H   P   N   T   L   F   T   P   H   I   G   S   A   V   R   A   V 901  cgcctggagattgaacgttgtgcagcgcagaacatcatccaggtattggcaggtgcgcgc  960
     gcggacctctaacttgcaacacgtcgcgtcttgtagtaggtccataaccgtccacgcgcg
301   R   L   E   I   E   R   C   A   A   Q   N   I   I   Q   V   L   A   G   A   R 961  ccaatcaacgctgcgaaccgtctgcccaaggccaatcctgccgcagactga (SEQ ID NO: 33) 1017
     ggttagttgcgacgcttggcagacgggttccggttaggacggcgtctgact
321   P   I   N   A   A   N   R   L   P   K   A   N   P   A   A   D   *   (SEQ ID NO: 12)
```

FIG. 15B

PHOSPHITE DEHYDROGENASE MUTANTS FOR NICOTINAMIDE COFACTOR REGENERATION

This application claims priority from U.S. Ser. No. 60/477,671 filed Jun. 11, 2003.

BACKGROUND OF THE INVENTION

Driven by recent technical advances in genetic engineering and new societal needs, the use of enzymes and microorganisms as catalysts to synthesize chemicals and materials is rapidly expanding. However, many challenges have yet to be fully addressed, such as developmental costs of biocatalysts and the type of chemistry performed. Most biocatalysts currently used in industry (~65%) are hydrolases that do not perform complex chemistry. The primary reason for this lack of use of complicated chemical reactions is that enzymes catalyzing more involved transformations often require one or more costly cofactors, making these reactions industrially impractical when the cofactor is added in a stoichiometric amount.

Oxidoreductases, for example, can be used for synthesis of chiral compounds, complex carbohydrates, and isotopically labeled compounds, but they often require NADH or NADPH as cofactors. The cost of NADH is about $40/mmol, whereas the price of NADPH is nearly $500/mmol (Sigma 2002 catalog), rendering stoichiometric use of either reduced cofactor at the kilogram scale prohibitively expensive. There is a need, therefore, to develop regeneration systems for NAD(P)(H) that would allow their addition in catalytic amounts, with the goal of making redox bioprocesses industrially feasible. Because approximately 80% of all reductases utilize NAD(P)(H) as a cofactor, probably accounting for over 300 known reactions, regeneration of these cofactors would be particularly advantageous.

A number of enzymatic, electrochemical, chemical, photochemical, and biological methods have been developed to regenerate cofactors. Advantages of cofactor regeneration in addition to reduced costs include simplified reaction work up, prevention of product inhibition from the cofactor, and sometimes a favorable influence on the reaction equilibrium. In some uses, the regenerative system drives the synthetic reaction forward, even when the formation of the desired product is less favored under standard conditions. Specific advantages of enzymatic strategies include high selectivity, compatibility with synthetic enzymes, and high turnover numbers. Aspects to be considered when using enzymatic methods include the expense and stability of the enzyme, cost of the substrate for the regenerative enzyme, ease of product purification, catalytic efficiency, $K_M$ for the cofactor, and thermodynamic driving force of the regenerative enzyme.

Of the enzymatic NADH regeneration systems, the best and most widely used enzyme is formate dehydrogenase (FDH) from *Candida boidini*. Phosphite dehydrogenase (PTDH) may have kinetic and practical advantages over FDH in certain applications, e.g. using PTDH as a regeneration system. This enzyme catalyzes the nearly irreversible oxidation of hydrogen phosphonate (phosphite) to phosphate, with the concomitant reduction of $NAD^+$ to NADH. The large change in free energy of this reaction ($\Delta G° = -63.3$ kJ/mol estimated from redox potentials) and the associated high equilibrium constant ($K_{eq}=1\times10^{11}$) makes PTDH a promising NADH regenerative enzyme. A particularly interesting application of PTDH is the facile production of isotopically labeled products. Deuterium or tritium labeled water can be used to readily and economically prepare labeled phosphite. Subsequent use of isotopically labeled phosphite during a synthetic reduction using PTDH for NADH regeneration has been shown to efficiently generate labeled products in high isotopic purity.

NADPH is significantly more expensive than NADH and currently no widely used system for its regeneration is available. The most promising enzymatic NADPH regeneration system is a mutant FDH from *Pseudomonas* sp. 101 (mut-Pse FDH) available from Jülich Fine Chemicals. However, the enzyme's mutations have not been made public, the catalytic efficiency is low (1 µM min−1), and the cost is high. Another alternative is the use of a soluble pyridine nucleotide transhydrogenase which catalyses the transfer of reducing equivalents between NAD+ and NADP+. Unfortunately, this route would require addition of both cofactors and a third enzyme to the process. Currently, the high cost of regenerating enzymes and inefficient regeneration makes the production of synthetic products requiring the use of NADPH not very attractive.

There are reports about the alteration of nicotinamide cofactor specificity including determinants and evolution of nicotinamide binding sites. However, altering cofactor specificity remains a challenge, because very few examples exist where catalytic efficiency for the disfavored cofactor NADPH has been significantly improved to approximately the activity with the preferred substrate. Even fewer are the examples where specificity becomes relaxed allowing high catalytic efficiency with both NAD(H) and NADP(H). Among this last group are the non-Rossman fold $NAD^+$-dependent isocitrate dehydrogenase, glucose-fructose oxidoreductase, glutathione reductase, and aldehyde dehydrogenase. A comparison of the strategies required to achieve efficient use of the non-physiological cofactor in these enzymes indicates that there is no clear recipe for success.

SUMMARY OF THE DISCLOSURE

Double and single mutations in phosphite dehydrogenase have (1) have relaxed nicotinamide cofactor ($NAD^+$ and $NADP^+$) specificity and increased catalytic efficiency, (2) increased thermostability; or (3) all of these improvements.

Phosphite dehydrogenase catalyses the nearly irreversible ($K_{eq}=1\times10^{11}$) oxidation of hydrogen phosphonate (phosphite) to phosphate with the concomitant reduction of $NAD^+$ to NADH. This enzyme is useful to regenerate NADH for in vivo biocatalytic processes requiring it as a reducing equivalent and also as a cheap source of specifically deuterated $(4R)\text{-}[4\text{-}^2H]\text{-}NAD^2H$.

The mutant enzymes with improved characteristics of the present disclosure were rationally designed by the incorporation of site-specific mutations to use both the natural cofactor NAD and the previously disfavored cofactor NADP with higher catalytic rate ($k_{cat}$) and efficiency ($k_{cat}/K_m$) and to provide thermostability. Mutants with both characteristics are even more valuable.

No three-dimensional structure of phosphite dehydronase is available and thus a homology model was built from three known crystal structures (1PSD, 1GDH, and 2DLD) and then docked with $NAD^+$ and $NADP^+$. From this model and relevant sequence alignments, two residues Glu175 and Ala176 were selected as important for cofactor specificity and were mutated to Ala175 (E175A) and Arg176 (A176R) individually and as a double mutant.

Both of the individual mutants resulted in significantly better efficiency for both cofactors, and the double mutant increased efficiency for $NAD^+$ by approximately 4-fold while increasing efficiency for $NADP^+$ approximately 1000-fold.

Isoelectric focusing of the proteins in a non-denaturing gel showed that the replacement with more basic residues does indeed change the effective pI of the protein. HPLC analysis of the enzymatic products verified that the reaction proceeds to completion using either substrate, and produces only the corresponding reduced cofactor and phosphate. Thermal inactivation studies show that this mutant is as stable as the wild-type enzyme and furthermore is protected from thermal inactivation by both cofactors while the wild-type is protected by NAD$^+$ only. These results provide clear evidence that a mutant with relaxed cofactor specificity has been engineered that appears to form a stable enzyme substrate complex with both cofactors. The double mutant phosphite dehydrogenase is used to regenerate either cofactor as well as produce (4R)-[4-$^2$H]-NADP$^2$H and is the foundation of other rational and irrational design efforts.

Several improved thermostable phosphite dehydrogenase (PTDH) mutants were obtained using directed evolution. Approximately 3200 clones created using error-prone PCR were screened in the first round, with incubation at 43° C. Amino acid substitutions Q132R, Q137R, I150F, Q215L and R275Q were identified as thermostablizing mutations. Site-directed mutagenesis was used to create combined mutants 4× (Q137R, I150F, Q215L, R275Q) and 5× (Q132R, Q137R, I150F, Q215L, R275Q). The $T_{50}$ of the 4× mutant is 13° C. higher and its $t_{1/2}$ at 45° C. is 180 times that of the parent PTDH (FIG. 8).

Mutants combining both relaxed cofactor specificity and increased thermostability compared to wild-type PTDH (PtxD), are formed by transferring the thermostabilizing mutations to mutants such as E175A and A176 with relaxed cofactor specificity.

ABBREVIATIONS

Computer Application and Network Services (CANS)
Dehydrogenases (DH)
Fast performance liquid chromatography (FPLC)
High performance liquid chromatography (HPLC)
Isoelectric focusing (IEF)
Isopropyl-β-D-thiogalactopyranoside (IPTG)
Molecular Operating Environment (MOE)
Nicotinamide adenine dinucleotide (NAD$^+$, NADH)
Nicotinamide adenine dinucleotide phosphate (NADP$^+$, NADPH)
Nitro blue tetrazolium (NBT),
Nuclear Magnetic Resonance (NMR)
Phenazine methosulfate (PMS)
Phosphite dehydrogenase (PTDH) (PtxD)
Polymerase chain reaction (PCR)
Protein Data Bank (PDB)
Root-mean-square (RMS)
Wild type (WT)

| Amino acid | Three-letter abbreviation | One-letter symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

BRIEF DESCRIPTION OF THE DRAWINGS

FIG. 1 shows sequence alignment of wild type (WT) PTDH (SEQ ID NO: 1) with three NAD+-dependent proteins used for homology modeling including glycerate dehydrogenase (1GDH; SEQ ID NO: 13), phosphoglycerate dehydrogenase (1PSD; SEQ ID NO: 14), and D-lactate dehydrogenase (2DLD; SEQ ID NO: 15). Residues under (←→) represent the GxxGxGxxG (SEQ ID NO: 16) nucleotide binding motif, residue under (●) represent the acidic residue responsible for binding the adenine 2'-hydroxyl group of NAD(H), and residues under (■) represent the catalytic residues.

FIG. 7 shows amino acid sequences of (A) PTDH wild-type; (B) E175A mutant; (C) A176R mutant; and (D) E175A, A176R double mutant; designated by SEQ ID NOS: 1-4 respectively. The mutated amino acids, with respect to the wild-type, are shown in bold.

FIG. 8A-B shows amino acid sequence (SEQ ID NO: 5) and a double strand DNA sequence (SEQ ID NO: 26) of the PTDH "parent".

FIG. 9A-B shows amino acid sequence (SEQ ID NO: 6) and a double strand DNA sequence (SEQ ID NO: 27) of Q132R mutant. The mutated amino acids in are highlighted in grey with respect to the parent, as in FIG. 8A-B.

FIG. 10A-B shows amino acid sequence (SEQ ID NO: 7) and a double strand DNA sequence (SEQ ID NO: 28) of Q137R mutant. The mutated amino acids in are highlighted in grey with respect to the parent, as in FIG. 8A-B.

FIG. 11A-B shows amino acid sequence (SEQ ID NO: 8) and a double strand DNA sequence (SEQ ID NO: 29) of I150F mutant. The mutated amino acids in are highlighted in grey with respect to the parent, as in FIG. 8A-B.

FIG. 12A-B shows amino acid sequence (SEQ ID NO: 9) and a double strand DNA sequence (SEQ ID NO: 30) of Q215L mutant. The mutated amino acids in are highlighted in grey with respect to the parent, as in FIG. 8A-B.

FIG. 13A-B shows amino acid sequence (SEQ ID NO: 10) and a double strand DNA sequence (SEQ ID NO: 31) of R275Q mutant. The mutated amino acids in are highlighted in grey with respect to the parent, as in FIG. 8A-B.

FIG. 14A-B shows an amino acid sequence (SEQ ID NO: 11) and a double strand DNA sequence (SEQ ID NO: 32) of PTDH 4× mutant. The mutated amino acids are highlighted in grey with respect to the parent in FIG. 8A-B.

FIG. 15A-B shows an amino acid sequence (SEQ ID NO: 12) and a double strand DNA sequence (SEQ ID NO: 33) of PTDH 5× mutant. The mutated amino acids are highlighted in grey with respect to the parent in FIG. 8A-B.

DETAILED DESCRIPTION OF THE DISCLOSURE

Figure 2:
FIG. 2 is a modeled structure of PTDH in comparison to the crystal structure of D-lactate dehydrogenase. The NAD+-binding domain (Rossmanfold) is on the right of each structure, while the catalytic domain is on the left, forming the active site in the middle. Residues indicated with asterisks represent the acidic residue responsible for binding 2'-hydroxyl of NAD(H) and residues indicated with arrows represent the catalytic residues.

1. Mutant with Relaxed Cofactor Specificity and Increased Catalytic Efficiency

Homology modeling was used to identify two residues, Glu175 and Ala176, in *Pseudomonas stutzeri* phosphite dehydrogenase (PTDH) as the principal determinants of nicotinamide cofactor ($NAD^+$ and $NADP^+$) specificity. Replacement of these two residues by site-directed mutagenesis with Ala175 and Arg176, both separately and in combination, resulted in PTDH mutants with relaxed cofactor specificity. All three mutants (2 singles and 1 double) exhibited significantly better catalytic efficiency for both cofactors, with the best kinetic parameters displayed by the double mutant, which had a 4-fold higher catalytic efficiency for $NAD^+$ and an 1000-fold higher efficiency for $NADP^+$. The cofactor specificity was changed from 100-fold in favor of $NAD^+$ for the wild-type enzyme to 3-fold in favor of $NADP^+$ for the double mutant. Isoelectric focusing of the proteins in a non-denaturing gel showed the replacement with these more basic residues indeed changed the effective pI of the protein. HPLC analysis of the enzymatic products of the double mutant verified that the reaction proceeded to completion using either substrate, and produced only the corresponding reduced cofactor and phosphate. Thermal inactivation studies showed the double mutant was as stable as the wild-type enzyme and was protected from thermal inactivation by both cofactors, while the wild-type enzyme was protected only by $NAD^+$. The combined results provide clear evidence that Glu175 and Ala176 are both critical for nicotinamide cofactor specificity. The rationally designed double mutant is useful for the development of an efficient in vitro NAD(P)H regeneration systems for oxidative biocatalysis.

Rational design was chosen as a means to produce improved enzymes for $NAD^+$ and $NADP^+$ cofactors. Unfortunately, the three-dimensional structure of PTDH had not been elucidated. Some information was gleaned from sequence alignments (FIG. 1) and the literature. PTDH contains the consensus sequence of a typical "Rossman" type fold including the GXXGXGXXG (SEQ ID NO: 16) motif common among D-hydroxy acid DHs (FIG. 1). Incorporated in this fold is an acidic residue (typically an aspartic acid and in rare cases a glutamic acid), located 18 residues downstream of the glycine motif and usually just after an aromatic residue. In PTDH this position (residue 175) is occupied by the less common glutamic acid and the previous residue (His174) is not the typical aromatic residue (FIG. 1). The Asp/Glu residue appears to provide a significant portion of substrate specificity for NAD(H) by hydrogen-bonding to one or both of the 2'- and 3'-hydroxyls of the adenine ribose, whereas NADP(H) specific dehydrogenases typically have a basic residue nearby this region to interact with the negatively charged 2'-phosphate. However, this sequence information alone was not deemed sufficient in lieu of a three-dimensional structure, especially considering the less common glutamic acid is in the proximity (±13 residues) of three other acidic residues and the typically found aromatic residue is absent. A homology model of PTDH was put to the test by using it as a template to create PTDH mutants with relaxed cofactor specificity. Two single mutants and a double mutant were generated using site-directed mutagenesis, and their kinetics, thermal stabilities, and reaction products are disclosed.

Using site-directed mutagenesis of two residues, Glu175 and Ala176, the nicotinamide cofactor specificity of PTDH was relaxed while the enzyme activity with both cofactors was enhanced. The charged residues near the 2'-position of $NAD^+$ are likely responsible for cofactor selectivity. This results differs from previous reports where activity with one or both cofactors is reduced in order to achieve a specificity change. In very few reports of other enzymes high catalytic efficiency accompanies the relaxation of specificity for NAD (H) and NADP(H). These examples include an increased activity with both cofactors for the non Rossman-fold $NAD^+$-dependent isocitrate dehydrogenase by the mutation of Asp328 to Lys, enhanced activity with both cofactors for glutathione reductase by deleting a loop near the cofactor binding domain, changing the catalytic activity of glucose-fructose oxidoreductase to that of a dehydrogenase as well as increasing cofactor promiscuity by various combinations of five mutations, and increasing the catalytic efficiency with both substrates in aldehyde dehydrogenase via a single mutation of Thr175 to Gln. In all these cases either many mutations and combinations were attempted, or extensive knowledge of the enzyme structure and homologous structures with opposite specificity was available.

The primary effect of the mutations in PTDH was on the Michaelis constants ($K_M$) of PTDH for $NADP^+$ and phosphite (in the presence of $NADP^+$), while smaller effects were seen in $k_{cat}$ with both $NAD^+$ and $NADP^+$ as substrates. Previously, the activity of WT PTDH with 1 mM phosphite and $NADP^+$ (6 mM) was estimated to be about 7% compared to the activity with 1 mM NAD$^+$ and 1 mM phosphite. However, an aspect of the mutant enzymes is that the $k_{cat}$ with NADP$^+$ is nearly 50% of the $k_{cat}$ with NAD$^+$. The reason for this discrepancy is that the concentration of phosphite previously used was well below its $K_M$ (in the presence of NADP$^+$). The $K_M$ was not determined for either substrate (NADP$^+$ or phosphite).

Replacing Ala176 with a positively charged residue (Arg) had the largest effect on the $K_M$ of NADP$^+$, but replacing the large negatively charged residue (Glu) with alanine also had a pronounced effect. The synergistic effect of these two mutations was larger than the effect of the two individual mutations. The resulting double mutant uses NADP$^+$ with 1000-fold greater efficiency ($k_{cat}/K_{M, NADP}$) and NAD$^+$ with 3.6-fold greater efficiency ($k_{cat}/K_{M, NAD}$) than WT. When comparing catalytic efficiency, the specificity for the cofactor changes from about 100-fold in favor of NAD$^+$ for the WT enzyme to about 3-fold in favor of NADP$^+$ for the double mutant. With all mutants and for both cofactors the turnover number ($k_{cat}$) was higher than for WT. An increase in the catalytic efficiency upon mutagenesis without adverse effect in some other property such as $k_{cat}$ or $K_M$ for the second substrate is a relatively rare observation, is not predictable.

An important purpose for the mutant enzymes is their use in cofactor regeneration and therefore, a decrease in thermal stability is undesired. The $t_{1/2}$ of thermal inactivation at 40.5° C. was determined for the WT enzyme and the double mutant. Because the half-lives are nearly identical (9.6 and 8.8 min respectively), the mutations have no significant effect on thermal stability. Previous reports were that when dehydrogenases bind their nicotinamide cofactor, they form a thermally more stable enzyme-substrate complex, but little to no effect is seen when the cofactor remains unbound. From the results of thermal inactivation in the presence of either cofactor, it is clear that the WT PTDH forms a complex only with NAD$^+$, whereas the double mutant forms a complex with both NAD$^+$ and NADP$^+$ with complete protection occurring with NADP$^+$. This provides further evidence that the increase in activity with NADP$^+$ is due mostly to enhanced binding of NADP$^+$ to the enzyme without disrupting the binding of NAD$^+$.

Because NAD$^+$ and NADP$^+$ differ only by a 2'-phosphate group, it was possible that the mutant enzyme dephosphorylated NADP$^+$ to NAD$^+$ and the observed activity was due to reduction of NAD$^+$. It was also possible that some NAD$^+$ was present in the NADP$^+$ used in the experiments. Therefore, HPLC was used to analyze the starting materials and enzymatic products. No NAD$^+$ was present in the NADP$^+$ within the detection limits of the HPLC, however the reverse was not true. The slight contamination of NADP$^+$ in the NAD$^+$ was not a problem because the enzymes all utilized NAD$^+$ with low $K_M$'s and the contamination level was only ~2%. When examining the reaction products, NADPH was produced from NADP$^+$ and NADH from NAD$^+$. Further examination of the HPLC data indicated no detectable remaining oxidized cofactor after reaction. This clearly shows that the reaction proceeds essentially to completion under physiological conditions and can provide a potent driving force when coupled to unfavorable reactions.

A useful enzyme for NADP$^+$ regeneration is a mutant Pseudomonas sp. 101 FDH (mut-Pse FDH) available from Juelich Fine Chemicals. Comparatively, the PTDH double mutant of the present disclosure has a catalytic efficiency with NADP$^+$ ($k_{cat}/K_{M,NADP}$) that is about 33-fold higher than that of mut-Pse FDH. Moreover, the PTDH double mutant can regenerate both cofactors and has a catalytic efficiency with NAD$^+$ ($k_{cat}/K_{M, NAD}$) that is 39-fold greater than mut-Pse FDH. In fact, it is also slightly more active (18%) than WT Pse FDH (NAD$^+$-dependent). Additionally, whereas the FDH mutants were assayed near optimal conditions (30° C.), PTDH mutants were assayed at 25° C. The $k_{cat}$ of PTDH is reduced at 25° C. in comparison to its activity at 35° C., and hence the improvement over mut-Pse FDH is underestimated. Finally, approximately 100-fold lower concentration of the second substrate (phosphite versus formate) is required for maximal activity with PTDH than with mut-Pse FDH. From this vantage point, the PTDH double mutant represents a very useful NADP$^+$ regeneration system.

Figure 4:
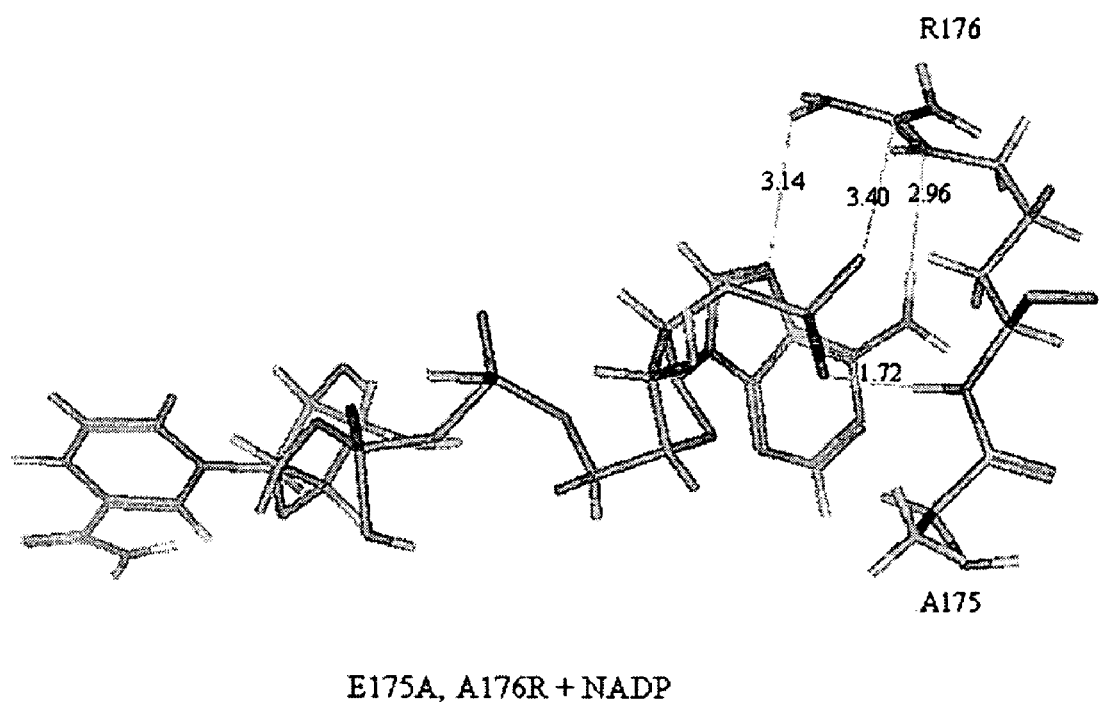
FIG. 4 is a model of the double mutant showing that R176 forms both ionic interactions and H-bonding interactions with NADP$^+$ while A175 allows sufficient room for binding of the 2'-phosphate of NADP$^+$.
Figure 5:
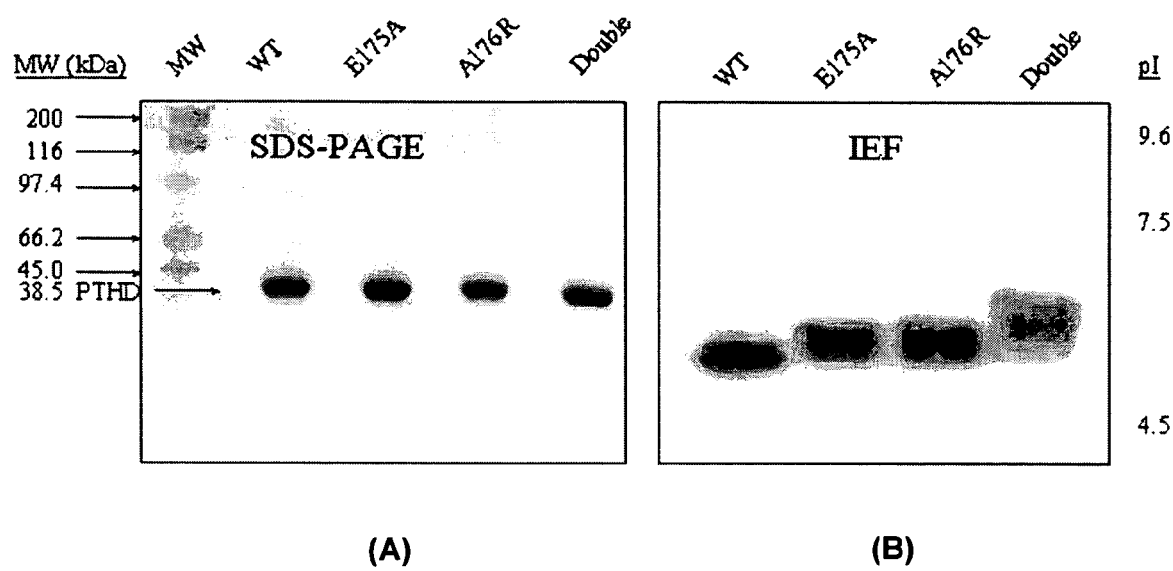
FIG. 5 shows (A) SDS-PAGE analysis of the purified WT and mutant PTDH proteins. (B) Isoelectric focusing native gel analysis of the same protein samples. The proteins are separated based on pI showing that both single mutants have a higher pI as predicted and that the effect is additive for the double mutant.

The relaxation of cofactor specificity of the mutants of the present disclosure was achieved by protein engineering based largely on structural information derived from homology modeling and sequence similarity with other NAD(P)$^+$-dependent dehydrogenases. From the homology model, it was predicted that the double mutant should bind NADP$^+$ by electrostatic and hydrogen-bond interactions between Arg176 and the cofactor, whereas Ala175 would not interfere with its binding (FIG. 4). The success of this strategy suggests that the homology model is at least a good working hypothesis for the structure of PTDH.

Homology Modeling. A protein sequence BLAST search was performed against the Protein Data Bank, and four sequences were chosen from the highest scoring results. They were D-glycerate DH from *Hyphomicrobium methylovorum* (1GDH), D-3-phosphoglycerate DH from *E. coli* (1PSD), D-lactate DH from *Lactobacillus helveticus* (2DLD) and NAD-dependent FDH from *Pseudomonas* sp. 101 (2NAC). These four enzymes represent NAD-specific two domain D-hydroxy acid dehydrogenases, and share between 25% and 30% sequence identity with PTDH. FDH (2NAC) was later excluded from this group because its structure was the most divergent and made the initial structural alignment difficult. The structural model was built as described in the Materials and Methods section. After the model was completed, it bore a striking resemblance to D-lactate dehydrogenase as seen in FIG. 2, with a RMS difference of 0.55 Å in the polypeptide backbone of the two structures. Using ProStat (Insight II) under default parameters the Phi and Psi angles were determined to be 79% within their expected values, comparing favorably to the 74.3%, 80.6% and 85.8% for the analysis of the template PDB structures 2DLD, 1PSD, and 1GDH respectively. A value of 90% correct self-compatability of amino acids with the modeled structure was obtained when inspected by Profiles3-D (Insight II, default parameters).

Three active site residues (Arg237, Glu266, and His292 in PTDH) are highlighted in both the sequence alignment (FIG. 1) and the structure comparison (FIG. 2). The location of these residues in the structure and the sequence is highly conserved in D-hydroxy acid dehydrogenases (Kochhar et al., 2000). In their typical roles, the histidine acts as an active site base, while the glutamic acid is hydrogen bonded to and raises the pKa of the histidine, thus making it a stronger base. The arginine is likely to be involved in binding the typically negatively charged substrates (D-hydroxy acids). These residues, through several possible mechanisms, are involved in catalysis for PTDH. This is supported by the model showing the close interactions of His292 and Glu266, with Arg237 positioned nearby this dyad. In addition, the hydride-accepting carbon of the modeled NAD$^+$ is very close to these residues (within 5.5 Å of the nearest heavy atom of His292).

When comparing different iterations of the modeling output, it was apparent that two regions are highly variable. The first is the loop directly after active site residue Glu266 containing the sequence 267-DWARADRPR-275 (SEQ ID NO: 17) and the second is the C-terminal region containing approximately the last 15 residues. The homologous regions for the template dehydrogenases are not well structurally conserved, introducing more freedom in modeling these regions. Furthermore, it is not unusual for loops and termini to obtain several conformations that are nearly equal in energy. The significance of the loop region in this model is that it is involved in the dimerization interface of the protein (in both the model and templates) and is located near the active site. The loop region is fairly well conserved in dehydrogenases that can oxidize phosphite, but not in other dehydrogenases. Thus, it is likely that this region containing three arginines is involved in binding phosphite. The flexibility of the C-terminal region may be in part responsible for the difficulties experienced during crystallization efforts. In many of the iterations of model structures, this region is found at or near the $NAD^+$ binding site. Interestingly, PTDH ends with Cys336 and it has previously been reported that for $NADP^+$-dependent malate dehydrogenase, a C-terminal disulfide bond helps regulate enzyme activity by blocking the $NADP^+$ binding site (Issakidis et al., 1994; Krimm et. al., 1999). Thus, it is possible that a similar disulfide is formed under certain conditions in PTDH. There is reduced activity when PTDH is purified in the absence of a thiol-reducing reagent such as DTT.

Modeling of Mutants with Relaxed Cofactor Specificity. It is apparent from the sequence alignments that PTDH binds $NAD^+$ by a Rossman-type fold, characterized by alternating $\alpha/\beta$ regions with a helixes on either side of a plane of 6 antiparallel $\beta$-sheets, and indeed this substructure is present in the model (FIG. 2). Among the various hydrogen bond contacts with $NAD^+$ created by the loop regions at the ends of the $\beta$-sheets, one particular residue, Glu175, stood out as a possible determinant of cofactor specificity. In the model, it is this residue that forms hydrogen-bonds with the hydroxyls of the adenine ribose of $NAD^+$ (FIG. 3) consistent with the sequence alignment prediction (FIG. 1). Glu175 would sterically and electrostatically repulse the 2'-phosphate of $NADP^+$, resulting in its poor binding by the WT enzyme. Replacing Glu175 with sterically smaller residues such as alanine, glycine, and valine might enhance the energetics of $NADP^+$ binding.

Figure 3:
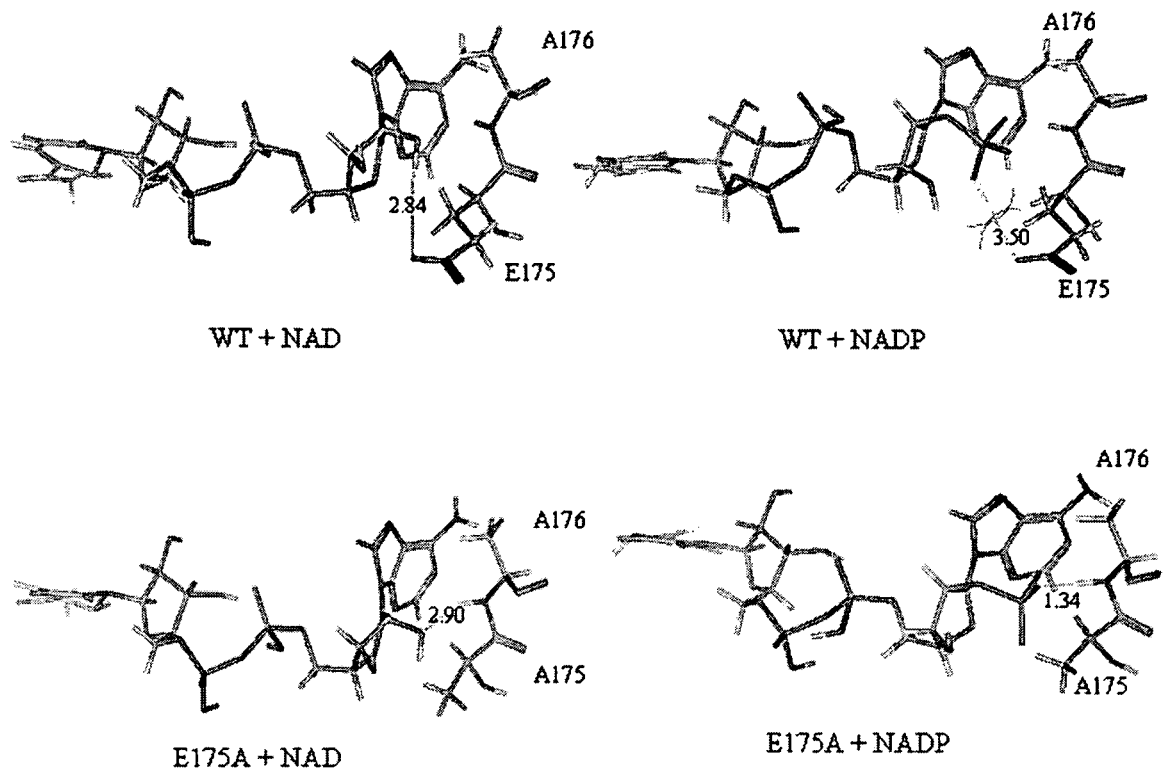
FIG. 3 shows a modeled cofactor interactions with mutant enzymes. The interaction between residue E175 of the WT enzyme and the 2'-hydroxyl of NAD$^+$ and the repulsion of this same residue by the 2'-phosphate of NADP$^+$ are apparent. Replacement of this residue with alanine in silico allows both cofactors to form stable interactions with the enzyme.

The model of a Glu175Ala mutant is shown in FIG. 3 in which the phosphate group of $NADP^+$ is not repelled, but is allowed to hydrogen-bond with the amide backbone proton. This figure also demonstrates that $NAD^+$ can still interact with the mutant enzyme in a similar manner as the WT enzyme with the exceptions of the hydrogen-bond contribution from Glu175 and more steric freedom in the mutant binding site. Unlike many Rossman $NAD^+$ binding sites, there is no aromatic residue in the +1 site relative to the acidic residue to sterically exclude a phosphate group. In $NADP^+$ dependent dehydrogenases, a basic residue (most commonly an arginine) involved in binding the 2'-phosphate moiety is typically present at this +1 position. In PTDH, a histidine is present at the −1 site with the +1 site was occupied by an alanine (FIG. 3). Therefore to probe potential interactions without steric interference, a double mutant Glu175Ala, Ala176Arg was modeled (FIG. 4). In the modeled binding of $NADP^+$ to this mutant, it was clear that the Arg could engage in electrostatic interactions with the 2'-phosphate of $NADP^+$, while also making hydrogen-bond contacts with the adenine base. It was therefore considered that this mutant would be capable of increasing the catalytic efficiency with $NADP^+$ without significantly reducing the catalytic efficiency with $NAD^+$.

Mutant Creation, Expression, and Purification. To explore the activity of the modeled mutants, they were first tested with the cell lysate activity assay described in Materials and Methods. Three mutations (Ala, Gly, and Val) at the Glu175 position were generated using mutagenic primers with a single degenerate codon as described in the Materials and Methods section. Thus, three different gene products were subcloned into the arabinose inducible pRW2 vector and tested simultaneously. The WM1788 strain of *E. coli* was used in the cell based assay since it contains a phoBR deletion that suppresses activation of endogenous phosphite oxidation pathways in *E. coli* resulting in minimized background activity. When the lysates of ten transformed clones expressing Glu175Ala, Glu175Gly, or Glu175Val mutants were assayed with $NADP^+$, four showed significant activity, while the others had activity indistinguishable from background. All ten clones were subsequently sequenced revealing that the four active clones contained the Glu175Ala mutation, while Glu175Val and Glu175Gly mutations were both represented in the sequenced DNA from inactive clones. The same pattern was observed in a $NAD^+$-dependent cell lysate activity assay. This suggests that the Glu175Val and Glu175Gly mutations resulted in inactive proteins, possibly as a result of misfolding, insolubility, or some other type of inactivation. Therefore, Glu175Ala was chosen for additional studies. Two additional mutants, Ala176Arg and the double mutant Glu175Ala-Ala176Arg were subsequently generated and assayed. These two mutants showed a qualitative increase in activity with $NADP^+$ over Glu175Ala and retained high activity with $NAD^+$.

To further characterize these mutants, proteins were overexpressed for large-scale purification as $His_6$-tag (tag shown in SEQ ID NO: 34) fusion proteins. The three mutant genes were inserted into the pET15b expression vector via described in the Materials and Methods. Overexpression in *E. coli* BL21 (DE3) resulted in production of PTDH at levels greater than 20% of total cellular protein. $Ni^{2+}$ affinity purification resulted in approximately 30-50 mg of highly pure protein from 1.5 L of each culture. SDS-PAGE analysis of the proteins showed no contaminating bands with only the expected 38.5 kDa band from the His6-tagged (tag shown in SEQ ID NO: 34) monomer. When the WT protein and the mutant proteins were analyzed based on pI by IEF, a clear distinction could be noticed. Both Glu175Ala and Ala176Arg had a more basic pI (~6.2) than the WT protein (~5.8) due to the removal of the negatively charged residue (Glu175Ala) and the addition of a positively charged residue (Ala176Arg), respectively. The double mutant resulted in a shift towards more basic pI (~6.6) approximately twice as large as for either single mutant when compared to the WT protein, due to the introduction of a positive residue and the loss of a negative residue. The proteins were activity stained based on NAD+-dependent PTDH activity, thus clearly showing that all mutants were active with the natural substrate.

Kinetic Analysis. The effect of the mutations on the nicotinamide cofactor preference of PTDH was assessed by comparing the kinetic parameters in the forward reaction (reduction of cofactor). The reverse reaction is too energetically unfavorable to assay by conventional means. The activities of the enzymes were determined as a function of concentration of either cofactor under saturating phosphite concentrations. Then activities were determined as a function of phosphite concentration in the presence of either cofactor at saturating concentration. The results of the kinetic analyses are depicted in Table 1. The turnover number ($k_{cat}$) of the WT enzyme is lower than previously described due to the assays being performed at 25° C. rather than at 30° C. and a slight deactivation by introduction of the His6-tag (SEQ ID NO: 34). The WT enzyme has a clear preference for NAD+ over NADP+ by about 100-fold when comparing catalytic efficiency ($k_{cat}/K_{M, NAD(P)}$), primarily as a function of lowered $K_M$. The effect of the mutations on relaxing this preference by lowering the $K_M$ for $NADP^{30}$ is clear. Glu175Ala lowers the $K_M$ by a factor of about 17, while Ala176Arg lowers the $K_M$ by a factor of about 33 compared to the WT enzyme. The synergistic effect of these two mutations results in a $K_M$ for $NADP^+$ approximately 700-fold lower in the double mutant. Unexpectedly, the turnover number improves approximately 35-55% in all cases. Therefore the overall efficiency with $NADP^+$ of the double mutant ($k_{cat}/K_{M, NADP}$) is approximately 1000-fold better than the WT enzyme. An additional 90-fold improvement in the $K_M$ for phosphite in the presence of $NADP^+$ was observed in the double mutant over the WT enzyme ($K_{M,Phosphite}$ in the presence of $NAD^+$ remains about the same).

For each mutant enzyme, an improvement in efficiency ($k_{cat}/K_{M, NAD}$) was also obtained with $NAD^+$ as the substrate. The $K_M$ for $NAD^+$ was reduced for both Glu175Ala and the double mutant while it was similar to WT for Ala176Arg, suggesting that the Glu175Ala mutation was responsible for reducing the $K_M$ in the double mutant. The turnover number was improved as well, with the highest increase of nearly 46% for Ala176Arg. The increase in $k_{cat}$ for the double mutant of about 34% coupled with the reduction in $K_M$ for $NAD^+$ (2.7-fold) resulted in an approximate 3.6-fold increase in catalytic efficiency ($k_{cat}/K_{M, NAD}$). In the presence of $NAD^+$, the $K_M$ of the double mutant for phosphite was not significantly changed.

HPLC Analysis. The purity of the nicotinamide substrates was analyzed to verify that none of the observed activity was the result of contamination. Samples of the oxidized cofactors $NAD(P)^+$ were therefore prepared (Sigma) and analyzed by ion-pair HPLC as described herein. There was no discernable $NAD^+$ present in the $NADP^+$ sample, which appeared to be greater than 99% pure. However, when analyzing $NAD^+$, a small amount of (~2%) of $NADP^+$ was present. In order to verify that NADPH was the respective product of $NADP^+$ reduction by the double mutant PTDH, a small-scale reaction was carried out. When the products were analyzed by HPLC, a single peak (UV 340 nm) was observed that had the same retention time as the authentic NADPH. The same process was carried out for $NAD^+$ as the substrate and again a peak was observed with a retention time corresponding to an authentic sample of NADH. A small peak with the retention time of NADPH was also observed corresponding to the reduction of the small amount (~2%) of $NADP^+$ present in the $NAD^+$ starting material, providing an internal control.

Figure 6:
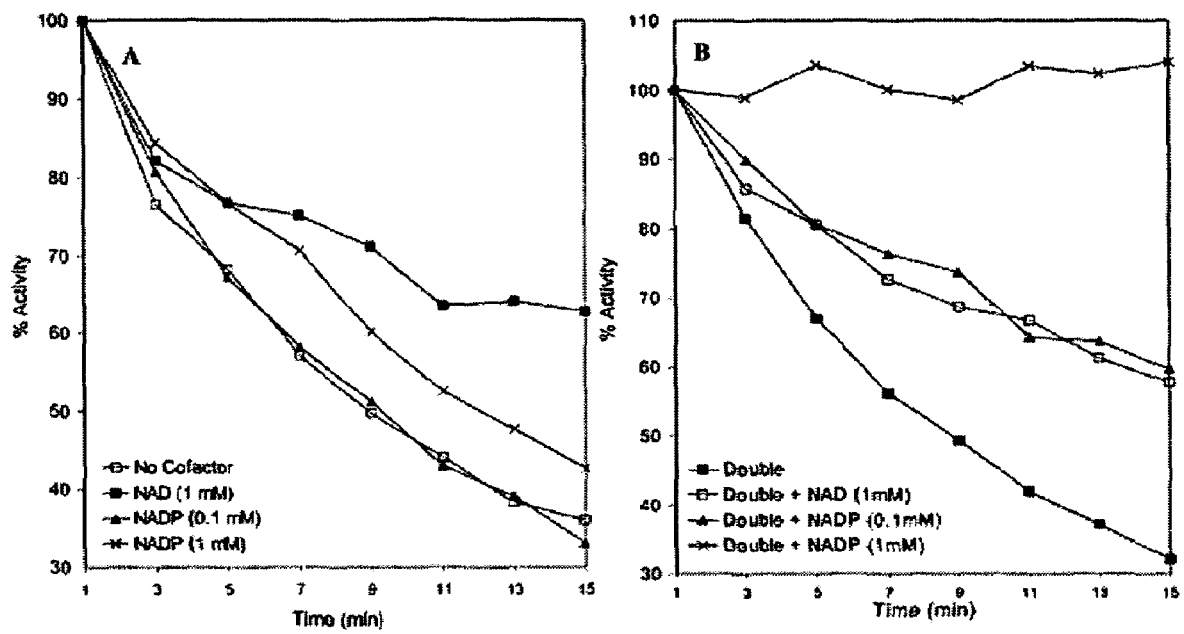
FIG. 6 shows thermal inactivation of WT and the double mutant (E175A; A176R) PTDH at 40.5° C. (A) WT PTDH is inactivated with a half-life of 9.6 min, but in the presence of 1 mM NAD$^+$ (and not 0.1 mM or 1 mM NADP$^+$), it forms a more thermally stable enzyme-substrate complex with a half-life of 23 min; (B) the double mutant PTDH is inactivated with a half-life of 8.8 min. In the presence of both 1 mM NAD$^+$ and 0.1 mM NADP$^+$ the double mutant forms a thermally stable enzyme substrate complex with half-lives around 19 min. In the presence of 1 mM NADP$^+$ the double mutant retains approximately 100% activity over a 15 minute period.
Figure 16:
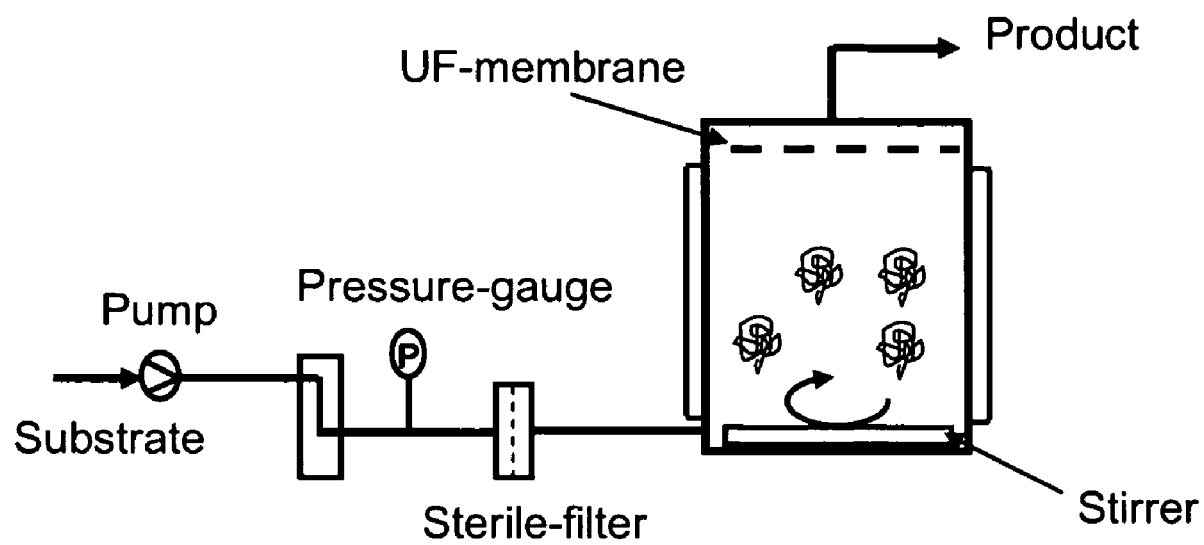
FIG. 16 shows an illustration of a membrane bioreactor to evaluate the catalytic performance of the wild type PTDH enzyme, the engineered PTDH variants, and the FDH enzyme, respectively.

Thermal Stability and NAD(P) Protection. WT PTDH proved relatively stable at 37° C., however at higher temperatures, irreversible thermal inactivation was observed. The WT enzyme gradually lost its activity over a 15-min period at 40.5° C. [FIG. 6(A)] with a half-life ($t_{1/2}$) of 9.6 min. The thermal stability of the double mutant was very similar, with a $t_{1/2}$ of 8.8 min [FIG. 6(B)]. Pre-incubation of the WT enzyme with 1 mM $NAD^+$ protected the enzyme from inactivation, lengthening the $t_{1/2}$ to nearly 23 min, while pre-incubation with 1 mM $NADP^+$ afforded almost no protection ($t_{1/2}$=11.1 min) [FIG. 6(A)]. Performing the same experiment with the double mutant resulted in complete protection from thermal inactivation by 1 mM $NADP^+$, retaining 100% activity after 15 min, and protection with 1 mM $NAD^+$ was similar to that of WT ($t_{1/2}$=18.9 min) [FIG. 6(B)]. Furthermore, when the $NADP^+$ concentrations were reduced to 0.1 mM, the WT enzyme was not protected ($t_{1/2}$=9.1 min), while the double mutant was still significantly protected with a $t_{1/2}$=19.1 min. The WT enzyme has a higher affinity for $NAD^+$, while the double mutant has relaxed cofactor specificity and strongly binds $NADP^+$.

2. Mutants with Improved Thermostability

Error-prone PCR was used to create a library of PTDHs with an average of 1-2 amino acid substitutions per variant. Approximately 3200 clones were screened for increased enzyme activity and thermostability, with incubation at 43° C. Five thermostable variants were identified that had half-lives and $T_{50}$ values greater than the parent (FIG. 8, Table 2). All five variants had single amino acid substitutions (Q132R, Q137R, I150F, Q215L and R275Q). All five first generation variants showed similar enzymatic activities to the parent, while the $K_M^{NAD+}$ varied slightly. Variant I150F had a 74% increase in $K_M^{Pt-H}$ (54 mM to 99 mM) compared to the parent.

Sequential site-directed mutagenesis was used to combine thermostable mutations from the first generation variants. 4× and 5× mutants were created using this method. The 4× mutant contains all the single amino acid substitutions except Q132R. This mutation was excluded based on its proximity to Q137R. The 4× mutant had a $T_{50}$ that is 13° C. higher and its $t_{1/2}$ at 45° C. is 180 times that of the parent PTDH. The 5× mutant had a $T_{50}$ that is 14° C. higher; however, its $t_{1/2}$ at 45° C. is only 150 fold better than the parent PTDH. The catalytic efficiency of the 4× mutant is ~17% lower than the parent, while the 5× mutant is ~35% lower. Both combined mutants had higher $K_M^{Pt-H}$ than the parent PTDH.

3. Mutants with Improved Thermostability and Relaxed Cofactor Specificity

The thermostabilizing mutations disclosed herein from directed evolution are introduced into the rationally designed mutants with relaxed cofactor specificity one by one using site-directed mutagenesis. Each variant is tested for its thermostability and activity toward both cofactors. Because the effects of thermostabilizing mutations are usually independent and cumulative, most of the thermostabilizing mutations should be able to be transplanted into the mutants with improved activity without losing their thermostabilizing effects. The final resulting mutant is highly thermostable and highly active toward both cofactors.

TABLE 1

Table 1:
Kinetic Parameters for Recombinant WT Phosphite Dehydrogenase and Mutants using $NADP^+$ and $NAD^+$ as Substrates

| Enzyme | $NAD^+$ | | | | $NADP^+$ | | | |
| --- | --- | --- | --- | --- | --- | --- | --- | --- |
| | $K_M$ (mM, $NAD^+$) | $k_{cat}$ (l/s)* | $k_{cat}/K_{M, NAD}$ (l/mM*min) | $K_M$ (mM, Pt—H) | $K_M$ (mM, $NADP^+$) | $k_{cat}$ (l/s) | $k_{cat}/K_{M, NADP}$ (l/mM*min) | $K_M$ (mM, Pt—H) |
| WT | 53 ± 9.0 | 2.93 ± 0.14 | 3.3 | 47 ± 6.0 | 2510 ± 410 | 1.41 ± 0.08 | 3.37E−02 | 1880 ± 325 |
| E175A | 16 ± 0.8 | 3.50 ± 0.05 | 13.1 | 23 ± 2.9 | 144 ± 14 | 2.18 ± 0.07 | 0.91 | 138 ± 25 |
| A176R | 60 ± 7.0 | 4.28 ± 0.08 | 4.3 | 156 ± 60 | 77 ± 8.4 | 2.18 ± 0.07 | 1.7 | 140 ± 20 |
| E175A, A176R | 20 ± 1.3 | 3.94 ± 0.08 | 11.8 | 61 ± 13 | 3.5 ± 0.5 | 1.90 ± 0.08 | 32.5 | 21 ± 2.7 |

*All assays were performed at 25° C. pH 7.25 in 50 mM MOPS

TABLE 2

Table 1:
Kinetic and thermostability parameters for the parent phosphite dehydorgenase, single mutants and combined mutants.[a]

|  | PTDH variant | $k_{cat}$ (min$^{-1}$) | $K_M$ (μM, NAD) | $k_{cat}/K_{M, NAD}$ (μM$^{-1}$min$^{-1}$) | $K_M$ (μM, Pt—H) | $t_{1/2}$ (min, 45° C.) | Fold Improvement ($t_{1/2}$ Mutant/$t_{1,2}$ Parent) | $T_{50}$ (° C.) |
|---|---|---|---|---|---|---|---|---|
|  | Parent | 262 ± 7.0 | 75 ± 18 | 3.4 | 57 ± 4.0 | 1.1 ± 0.3 | 1 | 39.0 ± 0.1 |
| Single Mutants | Q132R | 238 ± 21 | 60 ± 14 | 4.0 | 45 ± 3.0 | 2.3 ± 0.1 | 2.1 | 40.0 ± 0.3 |
|  | Q137R | 285 ± 25 | 66 ± 1.0 | 4.0 | 48 ± 5.0 | 3.8 ± 0.8 | 3.5 | 41.9 ± 0.2 |
|  | I150F | 262 ± 15 | 75 ± 30 | 3.5 | 99 ± 33 | 7.0 ± 1.6 | 6.4 | 42.2 ± 0.8 |
|  | Q215L | 278 ± 13 | 64 ± 16 | 4.5 | 58 ± 1.0 | 8.7 ± 0.8 | 7.9 | 42.5 ± 0.9 |
|  | R275Q | 244 ± 16 | 70 ± 11 | 3.3 | 78 ± 16 | 4.6 ± 0.4 | 4.2 | 40.7 ± 0.1 |
| 4x Mutant | Q137R/I150F/Q215L/R275Q | 218 ± 16 | 74 ± 18 | 3.0 | 144 ± 38 | 200 ± 8 | 182 | 52.4 ± 0.2 |
| 5x Mutant | Q132R/Q137R/I150F/Q215L/R275Q | 170 ± 3.0 | 46 ± 1.0 | 3.7 | 75 ± 18 | 161 ± 10 | 146 | 53.4 ± 0.2 |

[a]All assays were performed at 25° C., pH 7.25, in 50 mM MOPS.

Materials and Methods

Materials for Relaxed Specificity Mutants

*Escherichia coli* BL21 (DE3) and pET-15b were purchased from Novagen™(Madison, Wis.). *E. coli* WM1788 and plasmid pLA2 were provided by the inventors (Woodyer et al., 2003). The plasmid pRW2 was created from the pLA2 vector by digestion with Nde I and Pci I to remove the majority of lacZ, followed by directional cloning of the PTDH gene digested with the same enzymes. Cloned Pfu turbo polymerase was obtained from Stratagene™(La Jolla, Calif.) and Taq polymerase was obtained from Promega™(Madison, Wis.). PCR grade dNTPs were obtained from Roche Applied Sciences (Indianapolis, Ind.). DNA modifying enzymes Nde I, Pci I, Dpn I, Barn HI and T4 DNA ligase and their corresponding buffers were purchased from New England Biolabs (NEB) (Beverly, Mass.). D-glucose was purchased from Fisher Scientific (Pittsburgh, Pa.), while L-(+)-arabinose and tetrabutylammonium hydrogen sulfate were purchased from Fluka™(St. Louis, Mo.). Ampicillin, kanamycin, isopropyl-β-D-thiogalactopyranoside (IPTG), nitro blue tetrazolium (NBT), phenazine methosulfate (PMS), NAD+, NADP+, NADH, and NADPH were purchased from Sigma (St. Louis, Mo.). Phosphorous acid was obtained from Aldrich (Milwaukee, Wis.) and sodium phosphite from Riedel-de Haënel (Seelze, Germany). Other required salts and reagents were purchased from either Fisher or Sigma-Aldrich. QIAprep™ spin plasmid mini-prep kit, QIAEX II gel purification kit, and QIAquick™ PCR purification kit were purchased from Qiagen (Valencia, Calif.). Various oligonucleotide primers were obtained from Integrated DNA Technologies (Coralville, Iowa). Isoelectric focusing gels (pH 3-9), buffers, SDS-PAGE gels (12%) and protein size markers were purchased from Bio-Rad™(Hercules, Calif.).

Materials for Thermastable Mutants

*Escherichia coli* WM1788 and plasmid pLA2 (Woodyer et al., 2003) and modified plasmid pRW2 containing the mutant E175A gene was obtained as disclosed by Woodyer (2003). Taq DNA polymerase was obtained from Promega (Madison, Wis.) and cloned PfuTurbo DNA polymerase was obtained from Stratagene (La Jolla, Calif.). The DNA-modifying enzymes NdeI, PciI, BamHI, and T4 DNA ligase were purchased from New England Biolabs (NEB) (Beverly, Mass.). PCR grade dNTPs and DNaseI were obtained from Roche Applied Sciences (Indianapolis, Ind.).

Homology modeling. The following structures were downloaded from the Protein Data Bank (PDB) database (PDB accession code): glycerate dehydrogenase (1GDH) (Goldberg et al., 1994), phosphoglycerate dehydrogenase (IPSD) (Schuller et al., 1995), and D-lactate dehydrogenase (2DLD). Insight II software (Insight II, version 2000, Accelrys Inc., San Diego, Calif.) was used to align these three structures by conserved structural regions to achieve the lowest root-mean-square (RMS) score. The amino acid sequence of PTDH was then manually aligned by sequence with the structural alignment, taking great care to make sure the aligned sequences represented homologous structural regions. This alignment was then used as input for the automated MODELER module within Insight II using default parameters with moderate refinement of the structure and loop regions. Of approximately thirty structural models created, the best model was selected based on visual inspection for obvious flaws, the score from the Profiles 3-D function, and the ProStat inspection of psi and phi angles. NAD$^+$ from the 2DLD crystal structure was manually docked using Molecular Operating Environment (MOE, Chemical Computing Group Inc., Montreal, Canada) into the created model and then the whole structure was subjected to energy minimization to relieve steric and torsional artifacts from the modeling and docking processes. To create mutant enzymes in MOE, a rotamer search was performed with the mutated residue implemented in the homology model of the wild type (WT) enzyme. The lowest energy conformation was selected and energy minimized with the bound cofactor. All Insight II and MOE calculations were performed in the University of Illinois' School of Chemical Sciences' Computer Application and Network Services (CANS) in the VizLab laboratory.

Site-directed Muta genesis for Relaxed Spec ficity Mutants. An overlap extension PCR (OE-PCR) method was utilized to introduce site specific mutations using purified pRW2-PTDH-wild-type enzyme as the template. Two oligonucleotide primers flanking the gene were used in combination with the following mutagenic primers (underlined codons encode desired amino acid substitutions): E175A/G/V forward (5'-CTG CAG TAC CAC GBG GCG AAG GCT CTG-3' B=T,C,G) (SEQ ID NO: 18), E175A/G/V reverse (5'-CAG AGC CTT CGC CVC GTG GTA CTG CAG-3' V+A,C,G) (SEQ ID NO: 19), A176R forward (5'-CAG TAC CAC GAG CGG AAG GCT CTG GAT-3') (SEQ ID NO: 20), A176R reverse (5'- ATC CAG AGC CTT CCG CTC GTG GTA CTG-3') (SEQ ID NO: 21), double mutant forward (5'-CTG CAG TAC CAC GCG CGG AAG GCT CTG GAT AC-3') (SEQ ID NO: 22), double mutant reverse (5'-GT ATC CAT AGC CTT CCG CGC GTG GTA CTG CAG-3') (SEQ ID NO: 23). For the construction of each mutant, two separate PCR reactions were carried out, each containing one flanking primer and one mutagenic primer. The two PCR products were purified from the agarose gel after DNA electrophoresis, treated with Dpn I to remove methylated template, and then elongated by OE-PCR and amplified with the two flanking primers. Products of the correct size were purified from the gel, digested with Pci I and Nde I, and ligated into the Pci I-Nde I digested pRW2 vector. E. coli WM1788 was then transformed with the ligation mixture and grown on agar plates containing 50 µg/mL kanamycin. Several colonies were picked and clones were first analyzed by cell extract activity assay as described herein. Cultures of the clones with desired activity were grown again and the subsequently isolated plasmids were sequenced in both directions at the Biotechnology Center of the University of Illinois using the Big Dye™ Terminator sequencing method and an ABI PRISM® 3700 sequencer (Applied Biosystems, Foster City, Calif.). The genes containing the desired mutations were then subcloned into the pET15b expression vector as a N-terminal His6-Tag (tag shown in SEQ ID NO: 34) fusion using Nde I and BamH I restriction sites. Following subcloning, the mutant genes were again sequenced to eliminate the chance of PCR-introduced random mutations being incorporated into the final DNA construct. The plasmids containing the correct mutant genes were then used to transform E. coli BL21 (DE3) and colonies selected by ampicillin resistance were used for protein expression and purification.

Cell Extract Activity Assay. A solution of 100 mM Tris HCl pH 7.4 with 0.13% (w/v) gelatin and a 10× assay solution consisting of 1 mg/mL NBT, 0.5 mg/mL PMS, 15 mM NAD$^+$ or 60 mM NADP$^+$, and 40 mM phosphite were prepared. Directly prior to the assay, the latter mixture was diluted ten-fold in the Tris-HCl buffer. Cell lysates from arabinose induced E. coli WM1788 cells containing pRW2-PTDH were prepared by lysozyme incubation and freeze-thaw. Clarified cell extract (50 µL) was aliquoted into a 96-well plate followed by rapid addition of assay mix (150 µL) to each well using a multichannel pipetter. The initial rates of reaction and timed endpoints were observed by measuring the OD$_{580}$ in a Spectramax 340PC microplate reader (Molecular Devices, Sunnyvale, Calif.).

Overexpression and Purification of PTDH The buffers used for protein purification included start buffer A (SBA) (0.5 M NaCl, 20% glycerol, and 20 mM Tris, pH 7.6), start buffer B (SBB) (same as A but with 10 mM imidazole) and elute buffer (EB) (0.5 M imidazole, 0.5 M NaCl, 20% glycerol, and 20 mM Tris, pH 7.6). The transformants with pET15b derived vectors were grown in LB medium containing 100 µg/mL ampicillin at 37° C. with good aeration (shaking at 250 RPM). Upon reaching the log phase (OD$_{600}$~0.6) cells were induced with IPTG (final concentration 0.3 mM) and incubated at 25° C. for 8 h. Cells were harvested by centrifugation at 5,000 xg, 4° C., for is mm and then resuspended in 3 mL/(g cell pellet) start buffer containing 0.6 mg/g lysozyme and stored at −80° C. The frozen cell suspension was thawed at room temperature and lysed by sonication using a Vibracell™ sonicator (Newtown, Conn.) with amplitude set at 40%, and with a pulse sequence of 5 s on, 9.9 s off, for about 8-10 mm. Cells were centrifuged at 20,000 xg at 40° C. for 10 mm and the supernatant containing the crude extract was filtered through a 0.45 µm filter to remove any particles. The clarified supernatant was purified by FPLC, with a flow rate of 6 mL/min and fraction size of 8 mL. A POROS MC20 column (7.9 mL bed volume) (Boehringer Mannheim) was charged and equilibrated according to the manufacturer's protocol. The following method was used for purification of PTDH (with His$_6$-Tag) (tag shown in SEQ ID NO: 34) from a 20-60 mL of clarified supernatant (from 5-15 g cell paste): 1) load sample through pump, 100 mL, 2) wash column with 100 mL SBB, 3) elute with a linear gradient of 100 mL 100% SBB to 100% EB in 16.7 mm, and 4) wash with 100 mL EB. The elute fractions were monitored at λ280 nm. PTDH (with His6-Tag (tag shown in SEQ ID NO: 34)) typically eluted from the column halfway through the gradient (40% EB). The protein was concentrated using a Millipore Amicon 8400 stirred ultrafiltration cell with a YM10 membrane at 40° C., washed twice with 75 mL of 50 mM MOPS buffer (pH 7.25 containing 1 mM DTT and 200 mM NaCl) and concentrated again. The enzyme was then stored as concentrated as possible (usually>2 mg/ml) in 200 µL aliquots at −80° C., in a solution of Amicon wash buffer containing 20% glycerol.

Protein Characterization. Protein concentration was determined by the Bradford method (1976) using bovine serum albumin as a standard. The purity of the protein was analyzed by SDS-PAGE (Laemmli, 1970). SDS-PAGE gels were stained with coomassie brilliant blue. The net pI of the purified mutants and wild type proteins was determined by nondenaturing isoelectric focusing (IEF) (Hara et. al., 1982). The native IEF gel was subsequently activity stained by the same substrate mixture described above for cell extract activity assay, allowing visualization of the protein by NBT precipitation.

Kinetic Analysis. Initial rates were determined by monitoring the increase in absorbance, corresponding to the production of NAD(P)H ($\epsilon_{NAD(P)H}$=6.22 mM$^{-1}$cm$^{-1}$ at 340 nm). All initial rate assays were carried out at 25° C. using a Varian Cary 100 Bio UV-Visible spectrophotometer. The reaction was initiated by addition of 1.5-3.5 µg of PTDH. Concentrations of NAD$^+$ stock solutions were determined by UV-Visible spectroscopy ($\epsilon_{NAD^+}$=18 mM$^{-1}$cm$^{-1}$ at 260 nm). Phosphite concentrations were determined enzymatically by measuring the amount of NADH produced after all phosphite had been oxidized. Michaelis-Menten constants V$_{max}$ and K$_M$ were determined by a series of assays in which five varying concentrations of one substrate were used in the presence of saturating concentrations of the second substrate. The data was then converted to specific activity and fitted with the Michaelis-Menten equation. The WT and double mutants were also analyzed by a sequential matrix of 25 assays. This kinetic data was analyzed with a modified version of Cleland's program (1979). V$_{max}$ and K$_M$ for both phosphite and NAD(P)$^+$, were obtained by fitting the data to a sequential ordered mechanism with NAD(P)$^+$ binding first, where v is the initial velocity, V is the maximum velocity, K$_A$ and K$_B$ are the Michaelis-Menten constants for NAD(P)$^+$ and phosphite respectively, A and B are the concentrations of NAD(P)$^+$ and phosphite respectively, and K$_{ia}$ is the dissociation constant for A (NAD(P)$^+$) (eq. 1). All assays were performed in duplicate and each series of duplicates was performed a minimum of two times. Data presented in Table 1 represents an average of all statistically relevant data.

$$v=VAB/(K_{ia}K_B+K_AB+K_BA+AB) \qquad \text{(eq. 1)}$$

Thermal Inactivation. Thermal inactivation was studied by incubating either WT or the double mutant at 40.5° C. in 50 mM MOPS (pH 7.25) at a protein concentration of approximately 200 ng/µL. The samples were pre-incubated on ice for 5 min in the presence of 0.1 mM NADP$^+$, 1 mM NAD$^+$, or no cofactor, and then placed in the water bath. At various time points 10 µL of the protein sample was used to initiate the reaction of 0.5 mM of NAD$^+$ and 0.5 mM phosphite. Plotting the data as activity versus time followed by fitting to an exponential curve was performed to determine the half-lives of thermal inactivation.

HPLC Analysis of Reaction Products. The purity of the nicotinamide cofactor substrates and reaction products was assessed by HPLC. The separation of $NAD^+$, $NADP^+$, NADH, and NADPH was carried out as described by Micheli et al. (1993) with the following changes. An Agilent 1100 series solvent selector, pump, column and detector modules were utilized with a Zorbax 150 mm×3.0 mm C-18 (3.5 µm) column and a flow rate of 0.5 mL/min. Instead of 6 mM tetrabutylammonium phosphate, 5 mM tetrabutylammonium sulfate was used in the mobile phase. The total run time was increased to 20 min by the addition of a 5-min isocratic elution at the end of the gradient. Sample volumes for each pure substrate were 20 µL at a concentration of 1 mM in 50 mM MOPS (pH 7.25). Reaction products were prepared by mixing equal parts of 1 mM of the $NAD(P)^+$ with 5 mM phosphite, adding approximately 1 µg of enzyme, and allowing the reaction to proceed for 20 min at 30° C. These samples were then treated the same as other samples, tracking the UV absorbance at both 260 nm ($\lambda_{max}$ $NAD(P)^+$) and 340 nm ($\lambda_{max}$ NAD(P)H).

Random Mutagenesis and Library Creation

A mutant PTDH isolated by one of the inventors (Woodyer) served as the parent enzyme. The parent PTDH differs from wild type PTDH by five mutations (D13E, M26I, E175A, E332N and C336D). These mutations help increase enzyme solubility and enhance activity. Random mutagenesis was carried out by error-prone PCR as described by Zhao (1999). Plasmid pRW2 containing the parent gene was used as the template for the first generation mutagenesis. For the 1.0-kb PTDH-parent target gene, 0.20 mM $MnCl_2$ was required to obtain the desired level of mutagenesis (~1-2 amino acid substitutions). Forward (5'-TTTTTGGATG-GAGGAATT CATATG-3') (SEQ ID NO: 24) and reverse (5'-CGGGAAGACGTACGGGGTATACATGT-3') (SEQ ID NO: 25) primers were designed to amplify the gene. Restriction enzyme recognition sites, NdeI in the forward primer and PciI in the reverse primer, are shown in italics. PCR-mutated genes were digested with NdeI and PciI and ligated into a high copy shuttle vector. Ligation reactions (10 µl total volume) contained ~50 ng inserts, ~50 ng vector, 1X T4 DNA ligase buffer and 0.5 U T4 DNA ligase and were incubated at 16° C. for 16 h. The resulting plasmids were transformed into freshly prepared electrocompetent WM1788 cells, which were plated on Luria-Bertani agar plates containing 50 µg/ml kanamycin.

Thermostability Screening

Colonies were grown in 96-well plates containing 100 µL of LB media and 50 mg/ml kanamycin. The plates were incubated at 37° C. for 5 hours, and then the cultures were induced by adding 10 mM arabinose final concentration and incubating at 30° C. overnight. Cells were lysed by adding lysozyme (1 mg/ml) and Dnase 1 (4 U/ml) followed by a freeze-thaw. The plates were centrifuged at 4000 rpm for 15 min at 4° C. and 50 µL of clarified supernatant was transferred to two fresh plates. One plate was placed into a machined aluminum block holder that had been pre-incubated in an oven set at a specific temperature. After 10 min incubation at the elevated temperature, the plate was allowed to cool at room temperature. Initial and residual activities were determined by adding NBT assay solution and monitoring the change in absorbance at 580 nm for 5 min in a Spectramax 340PC microplate reader (Molecular Devices, Sunnyvale, Calif.). Thermostable mutants were identified by comparing residual activity to initial activity ($R_A/I_A$).

Cell Extract Activity Assay

A 100 mM solution of Tris-HCL buffer with 0.13%(w/v) was prepared, and the pH adjusted to 7.4 using 2 M HCl. A 10× assay mix consisting of 1 mg/ml NBT, 0.5 mg/ml PMS, 5 mM $NAD^+$ and 40 mM phosphite (phosphorous acid) was thawed and diluted in the Tris-HCL buffer to a 1× concentration directly prior to use. The assay mix was stored in 1 ml aliquots at −20° C. A 50 µL aliquot of E. coli cell lysate was placed in the desired well of a 96-well plate followed by the immediate addition of 150 µL of 1× assay mix to each well using a BioHit mulichannel pipetter. The $OD_{580}$ was measured in a Spectra Max 340 PC plate reader by Molecular Devices to determine the initial rate of reaction. The apparent $V_{max}$ for each well was analyzed by Softmax Pro Software.

DNA Sequencing and Analysis

Plasmid DNA from E. coli WM1788 was isolated using QIAprep spin plasmid mini-prep kits. Sequencing reactions consisted of 100-200 ng of template DNA, 10 pmol each primer, sequencing buffer and the BigDye reagent. Reactions were carried out for 25 cycles of 96° C. for 30 s, 50° C. for 15 s, 60° C. for 4 min in a PTC-200 Peltier thermal cycler from MJ Research. Prepared samples were submitted to the Biotechnology Center at the University of Illinois for sequencing on an ABI PRISM 3700 sequencer (Applied Biosystems, Foster City, Calif.).

PTDH Overexpression and Purification

Purifying the parent and mutant PTDHs was carried out by using a modified protocol as in Woodyer et al., 2003. Small-scale spin columns containing approximately 0.5 ml of BD Talon™ resin were used to purify multiple enzymes in parallel. The columns were equilibrated in start buffer A (SBA) (0.5 M NaCl, 20% glycerol, and 20 mM Tris-HCl, Ph=7.6) and proteins were eluted with 100% elution buffer (EB) (0.5 M imidazole, 0.5 M NaCl, 20% glycerol, and 20 mM Tris-HCl, Ph 7.6). Enzyme concentration was determined by measuring $A_{280}$ ($\epsilon$=30,000 $M^{-1}$ $cm^{-1}$).

Site-Directed Mutagenesis for Thermostable Mutants

A modified Megaprimer PCR method was used to introduce site-specific mutations using purified pRW2-parent as the template (Sarkar and Somner, 1990). For the construction of the combined 4× and 5× mutants, sequential PCR reactions were used to introduce each mutation. The 4× mutant contains the all single thermostable mutations except Q132R. The 5× mutant contains all single thermostable mutations. The genes were subcloned into pET15b as described by Woodyer et al. (2003).

Enzyme Kinetics

The kinetic rate constants for the mutant PTDHs were determined as described by Woodyer et al. (2003). The kinetic data combined with the thermostability parameters are summarized in Table 2.

Half-Lives of Thermal Inactivation

Purified enzymes (0.2 mg/ml) were incubated in an MJ Research (Watertown, Mass.) PTC-200 thermocylcer to study enzyme inactivation. Timed aliquots were taken at specific time points and placed on ice before assaying. Half-lives of thermal inactivation were calculated using $t_{1/2}=\ln2/k_{inact}$ where $k_{inact}$ is the inactivation rate constant obtained from the slope by plotting log (residual activity/initial activity) versus time.

Purified enzymes (0.2 mg/ml) were incubated for 20 min at various fixed elevated temperatures. After incubation, samples were placed on ice for 15 min before being assayed. Residual activity was determined and expressed as a percentage of the initial activity.

Production of PTDH in a Bioreactor

PTDH mutant enzymes can be produced in a large-scale bioreactor using standard techniques in microbiological fermentation and downstream processing. For example, a batch reactor containing suitable growth media for bacterial can be operated to grow the bacterial cells (harboring a plasmid that encodes a PTDH enzyme) to appropriate growth density for further downstream processing. Other cultures such as yeast can also be used and other modes of bioreactors such as continuous stirred reactor can also be used to produce and purify the enzyme in a large scale. Appropriate selection markers, oxygen concentration, agitation speeds, nutrient supplements can be optimized using techniques known in the art.

The standard downstream processing steps usually include harvesting cells by continuous centrifugation or cross-flow filtration. For intracellular products, cells are lysed by a French press, mill, sonication, or detergent and the cell debris is removed via crossflow filtration. Crude purification of the protein is generally performed via ammonium sulfate precipitation followed by chromatography (gel permeation, ion exchange, hydrophobic interaction, hydrophilic interaction, and/or metal affinity) and desalting with a dialysis membrane. The purified product is concentrated under vacuum with or without centrifugation and followed by freeze-drying if necessary. Concentration of the protein and activity of the enzyme can be performed using standard assays known to those of ordinary skill in the art.

Perform membrane reactor analysis on the phosphite/PTDH system and the formate/FDH system, respectively.

A membrane bioreactor is used as described by Wichmann (1981) to evaluate the catalytic performance of the wild type PTDH enzyme, the engineered PTDH variants, and the FDH enzyme, respectively. To save time and minimize the variations from reactor setup, a lab-scale enzyme membrane reactor has been purchased from Julich Fine Chemical which was founded by the scientists who developed the original formate/FDH system (Drs. R. -M. Kula and C. Wandrey). In the case of using $NAD^+$ as a cofactor, both enzymatic systems are coupled to the production of L-tert-Leucine from trimethylpyruvate using L-Leucine dehydrogenase. The product formation and substrate depletion is monitored by high-pressure liquid chromatography (HPLC). The total turnover number and stability of each system are determined. Data for the FDH system is consistent with those reported in the literature, which will be used as a benchmark for the development of our proposed phosphite/PtxD system. In the case of using $NADP^+$ as a cofactor, the engineered PtxD variants are coupled with recently discovered xylose reductase to convert xylose and glucose into xylitol and sorbitol, respectively. Similarly, the total turnover number and stability of each system will be determined. In both cases, the cofactors are tethered to polyethyleneglycol (PEG, MW=20,000) to increase their sizes as did in the existing FDH-based cofactor regeneration system.

DOCUMENTS CITED

These publications are incorporated by reference to the extent they disclose material relevant to the present application.

Banta, S., and Anderson, S. (2002) *J. Mol. Evol.* 55, 623-31.

Banta, S., Swanson, B. A., Wu, S., Jarnagin, A., and Anderson, S. (2002) *Biochemistry* 41, 6226-36.

Berrios-Rivera, S. J., Bennett, G. N., and San, K. Y. (2002) *Metab. Eng.* 4, 217-29.

Bocanegra, J. A., Scrutton, N. S., and Perham, R. N. (1993) *Biochemistry* 32, 2737-40.

Bommarius, A. S., and Drauz, K. (1994) *Bioorg. Med. Chem.* 2, 617-26.

Boonstra, B., Rathbone, D. A., French, C. E., Walker, E. H., and Bruce, N. C. (2000) *Appl. Environ. Microbiol.* 66, 5161-6.

Bradford, M. M. (1976) *Anal. Biochem.* 72, 248-54.

Carugo, O., and Argos, P. (1997) *Proteins* 28, 10-28.

Carugo, O., and Argos, P. (1997) *Proteins* 28, 29-40.

Chen, R., Greer, A., and Dean, A. M. (1995) *Proc. Natl. Acad Sci.* U.S.A. 92, 11666-70.

Chen, R., Greer, A., and Dean, A. M. (1996) *Proc. Natl. Acad. Sci.* U.S.A. 93, 12171-6.

Chenault, H. K., and Whitesides, G. M. (1987) *Appl. Biochem. Biotechnol.* 14, 147-97.

Cleland, W. W. (1979) *Methods Enzymol.* 63, 103-38.

Corbier, C., Clermont, S., Billard, P., Skarzynski, T., Branlant, C., Wonacott, A., and Branlant, G. (1990) *Biochemistry* 29, 7101-6.

Costas, A. M., White, A. K., and Metcalf, W. W. (2001) *J. Biol. Chem.* 276, 17429-36.

Danielson, U. H., Jiang, F., Hansson, L. O., and Mannervik, B. (1999) *Biochemistry* 38, 9254-63.

Faber, K. (1997) *Biotransformations In Organic Chemistry*: A Textbook, 3rd ed., Springer-Verlag, Berlin, Germany.

Feeney, R., Clarke, A. R., and Holbrook, J. J. (1990) *Biochem. Biophys. Res. Commun.* 166, 667-72.

Galkin, A., Kulakova, L., Ohshima, T., Esaki, N., and Soda, K. (1997) *Protein. Eng.* 10, 687-90.

Goldberg, J. D., Yoshida, T., and Brick, P. (1994) *J. Mol. Biol.* 236, 1123-40.

Grimshaw, C. E., Matthews, D. A., Varughese, K. I., Skinner, M., Xuong, N. H., Bray, T., Hoch, J., and Whiteley, J. M. (1992) *J. Biol. Chem.* 267, 15334-9.

Haldimann, A., and Wanner, B. L. (2001) *J. Bacteriol.* 183, 6384-93.

Hara, A., Deyashiki, Y., Nakagawa, M., Nakayama, T., and Sawada, H. (1982) *J. Biochem.* 92, 1753-62.

Holderman, A. and Wanner B. L. (2001) *I of Bact.* 183, 6384-6393.

Holmberg, N., Ryde, U., and Bulow, L. (1999) *Protein. Eng.* 12, 851-6.

Huang, Y. W., Pineau, I., Chang, H. J., Azzi, A., Bellemare, V., Laberge, S., and Lin, S. X. (2001) *Mol. Endocrinol.* 15, 2010-20.

Hurley, J. H., Chen, R., and Dean, A. M. (1996) *Biochemistry* 35, 5670-8.

Issakidis, E., Saarinen, M., Decottignies, P., Jacquot, J. P., Cretin, C., Gadal, P., and Miginiac-Maslow, M. (1994) *J. Biol. Chem.* 269, 3511-7.

Kochhar, S., Lamzin, V. S., Razeto, A., Delley, M., Hottinger, H., and Germond, J. E. (2000) *Eur. J. Biochem.* 267, 1633-9.

Koeller, K. M., and Wong, C. H. (2001) *Nature* 409, 232-40.

Krimm, I., Goyer, A., Issakidis-Bourguet, E., Miginiac-Maslow, M., and Lancelin, J. M. (1999) *J. Biol. Chem.* 274, 34539-42.

Laemmli, U. K. (1970) *Nature* 227, 680-5.

Lauvergeat, V., Kennedy, K., Feuillet, C., McKie, J. H., Gorrichon, L., Baltas, M., Boudet, A. M., Grima-Pettenati, J., and Douglas, K. T. (1995) *Biochemistry* 34, 12426-34.

Leonida, M. D. (2001) *Curr. Med. Chem.* 8, 345-69.

Liese, A., and Filho, M. V. (1999) *Curr. Opin. Biotechnol.* 10, 595-603.

McCoy, M. (2001) *C. & E.N.* 79, 37-43.

Micheli, V., Simmonds, H. A., Bari, M., and Pompucci, G. (1993) *Clin. Chim. Acta.* 220, 1-17.

Nakanishi, M., Matsuura, K., Kaibe, H., Tanaka, N., Nonaka, T., Mitsui, Y., and Hara, A. (1997) *J. Biol. Chem.* 272, 2218-22.

Nishiyama, M., Birktoft, J. J., and Beppu, T. (1993) *J. Biol. Chem.* 268, 4656-60.

Rossmann, M. G., Moras, D., and Olsen, K. W. (1974) *Nature* 250, 194-9.

Sarkar, G., and Sommer, S. S. (1990) *Biotechniques* 8, 404-407.

Schepens, I., Johansson, K., Decottignies, P., Gillibert, M., Hirasawa, M., Knaff, D. B., and Miginiac-Maslow, M. (2000) *J. Biol. Chem.* 275, 20996-1001.

Schmid, A., Dordick, J. S., Hauer, B., Kiener, A., Wubbolts, M., and Witholt, B. (2001) *Nature* 409, 258-68.

Schuller, D. J., Grant, G. A., and Banaszak, L. J. (1995) *Nat. Struct. Biol.* 2, 69-76.

Scrutton, N. S., Berry, A., and Perham, R. N. (1990) *Nature* 343, 38-43.

Serov, A. E., Popova, A. S., Fedorchuk, V. V., and Tishkov, V. I. (2002) *Biochem. J.* 367, 841-7.

Steen, I. H., Lien, T., Madsen, M. S., and Birkeland, N. K. (2002) *Arch. Microbiol.* 178, 297-300.

Tishkov, V. I., Galkin, A. G., Fedorchuk, V. V., Savitsky, P. A., Rojkova, A. M., Gieren, H., and Kula, M. R. (1999) *Biotechnol. Bioeng.* 64, 187-93.

van der Donk, W. A., and Zhao, H. (2003) *Curr. Opin. Biotechnol.*, in press.

Vrtis, J. M., White, A. K., Metcalf, W. W., and van der Donk, W. A. (2001) *J. Am. Chem. Soc.* 123, 2672-3.

Vrtis, J. M.; White, A. K.; Metcalf, W. W.; Van der Donk, W. A. *Angew. Chem., Intl. Ed.* 2002, 41, 3257

Vrtis, J. M., White, A., Metcalf, W.W, van der Donk, W.A. (2002) *Angew. Chem. Int. Ed. Engl.* 41, 3257-3259.

Wang, H., Lei, B., and Tu, S. C. (2000) *Biochemistry* 39, 7813-9.

Wichmann, R., et al. (1981). *Biotechnol Bioeng*, 67(6): p. 791-804.

Wiegert, T., Sahm, H., and Sprenger, G. A. (1997) *J. Biol. Chem.* 272, 13126-33.

Wierenga, R. K., De Maeyer, M. C. H., and Hol, W. G. J. (1985) *Biochemistry* 24, 1346-1357.

Woodyer, R., van der Donk, W. A., and Zhao, H. (2003) *Biochemistry* 42, 11604-11614.

Yaoi, T., Miyazaki, K., Oshima, T., Komukai, Y., and Go, M. (1996) *J. Biochem.* 119, 1014-8.

Zaks, A. (2001) *Curr. Opin. Chem. Biol.* 5, 130-6.

Zhang, L., Ahvazi, B., Szittner, R., Vrielink, A., and Meighen, E. (1999) *Biochemistry* 38, 11440-7.

Zhao, H., Chockalingam, K., and Chen, Z. (2002) *Curr. Opin. Biotechnol.* 13, 104-10.

Zhao, H., Moore, J. C., Volkov, A. A., and Arnold, F. H. (1999) in *Manual of Industrial Microbiology and Biotechnology* (Demain, A. L., and Davies, J. E., Eds.) pp 597-604, ASM Press, Washington, D.C.

The invention claimed is:

1. A purified mutant of a wild-type phosphite dehydrogenase comprising the amino acid sequence of SEQ ID NO: 1, with improved catalytic activity for nicotinamide cofactor regeneration as compared with a wild-type phosphite dehydrogenase, and wherein the mutant phosphite dehydrogenase consists of an amino acid mutation selected from the group consisting of Glu175 to Ala 175 and Ala176 to Arg 176 of SEQ ID NO: 1.

2. The phosphite dehydrogenase of claim 1, further defined as having increased catalytic efficiency for cofactors $NAD^+$ and $NADP^+$ as compared to a wild-type phosphite dehydrogenase, wherein the catalytic efficiency ($k_{cat}/K_M$) with $NADP^+$ is about 1000-fold higher than the wild-type phosphite dehydrogenase.

3. The phosphite dehydrogenase of claim 2 consisting of the mutations from Glu175 to Ala 175 and from Ala176 to Arg176 of SEQ ID NO:1.

4. The phosphite dehydrogenase of claim 2 consisting of a mutation from Glu175 to Ala175 of SEQ ID NO:1.

5. The phosphite dehydrogenase of claim 2 consisting of a mutation from Ala176 to Arg 176 of SEQ ID NO:1.

6. A mutant of a wild-type phosphite dehydrogenase comprising the amino acid sequence of SEQ ID NO: 1, with improved thermostability and improved catalytic activity for nicotinamide cofactor regeneration as compared with a wild-type phosphite dehydrogenase and, wherein the mutant phosuhite dehydrogenase consists of one or more mutations selected from the group consisting of E175A; A176R; Q132R; Q137R; I150F; Q 215 L; R275Q; Q137R, I150F, Q215L, and R275Q; and Q132R, Q137R, I150F, Q215L, and R275Q of SEQ ID NO: 1.

7. The phosphite dehydrogenase mutant of claim 1 characterized by relaxed cofactor specificity and improved thermostability compared to the wild-type phosphite dehydrogenase, wherein the relaxed cofactor specificity is the ability of the phosphite dehydrogenase to binding to cofactors $NAD^+$ and $NADP^+$.

* * * * *

SEQUENCE LISTING

<160> NUMBER OF SEQ ID NOS: 34

<210> SEQ ID NO 1
<211> LENGTH: 336
<212> TYPE: PRT
<213> ORGANISM: Pseudomonas stutzeri

<400> SEQUENCE: 1

```
Met Leu Pro Lys Leu Val Ile Thr His Arg Val His Asp Glu Ile Leu
 1               5                  10                  15

Gln Leu Leu Ala Pro His Cys Glu Leu Met Thr Asn Gln Thr Asp Ser
             20                  25                  30

Thr Leu Thr Arg Glu Glu Ile Leu Arg Arg Cys Arg Asp Ala Gln Ala
         35                  40                  45

Met Met Ala Phe Met Pro Asp Arg Val Asp Ala Asp Phe Leu Gln Ala
     50                  55                  60

Cys Pro Glu Leu Arg Val Val Gly Cys Ala Leu Lys Gly Phe Asp Asn
 65                  70                  75                  80

Phe Asp Val Asp Ala Cys Thr Ala Arg Gly Val Trp Leu Thr Phe Val
                 85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125

Gly Glu Phe Gln Gly Trp Gln Pro Gln Phe Tyr Gly Thr Gly Leu Asp
    130                 135                 140

Asn Ala Thr Val Gly Ile Leu Gly Met Gly Ala Ile Gly Leu Ala Met
145                 150                 155                 160
```

```
Ala Asp Arg Leu Gln Gly Trp Gly Ala Thr Leu Gln Tyr His Glu Ala
            165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
            195                 200                 205

Pro Leu Asn Ala Asp Thr Gln His Leu Val Asn Ala Glu Leu Leu Ala
            210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
            245                 250                 255

Gly Tyr Ala Ala Asp Val Phe Glu Met Glu Asp Trp Ala Arg Ala Asp
            260                 265                 270

Arg Pro Arg Leu Ile Asp Pro Ala Leu Leu Ala His Pro Asn Thr Leu
            275                 280                 285

Phe Thr Pro His Ile Gly Ser Ala Val Arg Ala Val Arg Leu Glu Ile
            290                 295                 300

Glu Arg Cys Ala Ala Gln Asn Ile Ile Gln Val Leu Ala Gly Ala Arg
305                 310                 315                 320

Pro Ile Asn Ala Ala Asn Arg Leu Pro Lys Ala Glu Pro Ala Ala Cys
            325                 330                 335

<210> SEQ ID NO 2
<211> LENGTH: 336
<212> TYPE: PRT
<213> ORGANISM: Pseudomonas stutzeri

<400> SEQUENCE: 2

Met Leu Pro Lys Leu Val Ile Thr His Arg Val His Asp Glu Ile Leu
  1                 5                  10                  15

Gln Leu Leu Ala Pro His Cys Glu Leu Met Thr Asn Gln Thr Asp Ser
            20                  25                  30

Thr Leu Thr Arg Glu Glu Ile Leu Arg Arg Cys Arg Asp Ala Gln Ala
            35                  40                  45

Met Met Ala Phe Met Pro Asp Arg Val Asp Ala Asp Phe Leu Gln Ala
        50                  55                  60

Cys Pro Glu Leu Arg Val Val Gly Cys Ala Leu Lys Gly Phe Asp Asn
 65                 70                  75                  80

Phe Asp Val Asp Ala Cys Thr Ala Arg Gly Val Trp Leu Thr Phe Val
            85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
            115                 120                 125

Gly Glu Phe Gln Gly Trp Gln Pro Gln Phe Tyr Gly Thr Gly Leu Asp
            130                 135                 140

Asn Ala Thr Val Gly Ile Leu Gly Met Gly Ala Ile Gly Leu Ala Met
145                 150                 155                 160

Ala Asp Arg Leu Gln Gly Trp Gly Ala Thr Leu Gln Tyr His Ala Ala
            165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
            195                 200                 205
```

```
Pro Leu Asn Ala Asp Thr Gln His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
                260                 265                 270

Arg Pro Arg Leu Ile Asp Pro Ala Leu Leu Ala His Pro Asn Thr Leu
            275                 280                 285

Phe Thr Pro His Ile Gly Ser Ala Val Arg Ala Val Arg Leu Glu Ile
        290                 295                 300

Glu Arg Cys Ala Ala Gln Asn Ile Ile Gln Val Leu Ala Gly Ala Arg
305                 310                 315                 320

Pro Ile Asn Ala Ala Asn Arg Leu Pro Lys Ala Glu Pro Ala Ala Cys
                325                 330                 335
```

<210> SEQ ID NO 3
<211> LENGTH: 336
<212> TYPE: PRT
<213> ORGANISM: Pseudomonas stutzeri

<400> SEQUENCE: 3

```
Met Leu Pro Lys Leu Val Ile Thr His Arg Val His Asp Glu Ile Leu
1               5                   10                  15

Gln Leu Leu Ala Pro His Cys Glu Leu Met Thr Asn Gln Thr Asp Ser
                20                  25                  30

Thr Leu Thr Arg Glu Glu Ile Leu Arg Arg Cys Arg Asp Ala Gln Ala
            35                  40                  45

Met Met Ala Phe Met Pro Asp Arg Val Asp Ala Asp Phe Leu Gln Ala
        50                  55                  60

Cys Pro Glu Leu Arg Val Val Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125

Gly Glu Phe Gln Gly Trp Gln Pro Gln Phe Tyr Gly Thr Gly Leu Asp
    130                 135                 140

Asn Ala Thr Val Gly Ile Leu Gly Met Gly Ala Ile Gly Leu Ala Met
145                 150                 155                 160

Ala Asp Arg Leu Gln Gly Trp Gly Ala Thr Leu Gln Tyr His Glu Arg
                165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Gln His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
```

```
                   245                 250                 255
Gly Tyr Ala Ala Asp Val Phe Glu Met Glu Asp Trp Ala Arg Ala Asp
            260                 265                 270

Arg Pro Arg Leu Ile Asp Pro Ala Leu Leu Ala His Pro Asn Thr Leu
        275                 280                 285

Phe Thr Pro His Ile Gly Ser Ala Val Arg Ala Val Arg Leu Glu Ile
    290                 295                 300

Glu Arg Cys Ala Ala Gln Asn Ile Ile Gln Val Leu Ala Gly Ala Arg
305                 310                 315                 320

Pro Ile Asn Ala Ala Asn Arg Leu Pro Lys Ala Glu Pro Ala Ala Cys
                325                 330                 335

<210> SEQ ID NO 4
<211> LENGTH: 336
<212> TYPE: PRT
<213> ORGANISM: Pseudomonas stutzeri

<400> SEQUENCE: 4

Met Leu Pro Lys Leu Val Ile Thr His Arg Val His Asp Glu Ile Leu
 1               5                  10                  15

Gln Leu Leu Ala Pro His Cys Glu Leu Met Thr Asn Gln Thr Asp Ser
             20                  25                  30

Thr Leu Thr Arg Glu Glu Ile Leu Arg Arg Cys Arg Asp Ala Gln Ala
         35                  40                  45

Met Met Ala Phe Met Pro Asp Arg Val Asp Ala Asp Phe Leu Gln Ala
     50                  55                  60

Cys Pro Glu Leu Arg Val Val Gly Cys Ala Leu Lys Gly Phe Asp Asn
 65                  70                  75                  80

Phe Asp Val Asp Ala Cys Thr Ala Arg Gly Val Trp Leu Thr Phe Val
                 85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125

Gly Glu Phe Gln Gly Trp Gln Pro Gln Phe Tyr Gly Thr Gly Leu Asp
    130                 135                 140

Asn Ala Thr Val Gly Ile Leu Gly Met Gly Ala Ile Gly Leu Ala Met
145                 150                 155                 160

Ala Asp Arg Leu Gln Gly Trp Gly Ala Thr Leu Gln Tyr His Ala Arg
                165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Gln His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Arg Leu Ile Asp Pro Ala Leu Leu Ala His Pro Asn Thr Leu
        275                 280                 285
```

```
Phe Thr Pro His Ile Gly Ser Ala Val Arg Ala Val Arg Leu Glu Ile
        290                 295                 300

Glu Arg Cys Ala Ala Gln Asn Ile Ile Gln Val Leu Ala Gly Ala Arg
305                 310                 315                 320

Pro Ile Asn Ala Ala Asn Arg Leu Pro Lys Ala Glu Pro Ala Ala Cys
                325                 330                 335

<210> SEQ ID NO 5
<211> LENGTH: 336
<212> TYPE: PRT
<213> ORGANISM: Pseudomonas stutzeri

<400> SEQUENCE: 5

Met Leu Pro Lys Leu Val Ile Thr His Arg Val His Glu Glu Ile Leu
  1               5                  10                  15

Gln Leu Leu Ala Pro His Cys Glu Leu Ile Thr Asn Gln Thr Asp Ser
                 20                  25                  30

Thr Leu Thr Arg Glu Glu Ile Leu Arg Arg Cys Arg Asp Ala Gln Ala
             35                  40                  45

Met Met Ala Phe Met Pro Asp Arg Val Asp Ala Asp Phe Leu Gln Ala
     50                  55                  60

Cys Pro Glu Leu Arg Val Val Gly Cys Ala Leu Lys Gly Phe Asp Asn
 65                  70                  75                  80

Phe Asp Val Asp Ala Cys Thr Ala Arg Gly Val Trp Leu Thr Phe Val
                 85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
            115                 120                 125

Gly Glu Phe Gln Gly Trp Gln Pro Gln Phe Tyr Gly Thr Gly Leu Asp
        130                 135                 140

Asn Ala Thr Val Gly Ile Leu Gly Met Gly Ala Ile Gly Leu Ala Met
145                 150                 155                 160

Ala Asp Arg Leu Gln Gly Trp Gly Ala Thr Leu Gln Tyr His Ala Ala
                165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Gln His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Arg Leu Ile Asp Pro Ala Leu Leu Ala His Pro Asn Thr Leu
        275                 280                 285

Phe Thr Pro His Ile Gly Ser Ala Val Arg Ala Val Arg Leu Glu Ile
    290                 295                 300

Glu Arg Cys Ala Ala Gln Asn Ile Ile Gln Val Leu Ala Gly Ala Arg
305                 310                 315                 320

Pro Ile Asn Ala Ala Asn Arg Leu Pro Lys Ala Asn Pro Ala Ala Asp
                325                 330                 335
```

<210> SEQ ID NO 6
<211> LENGTH: 336
<212> TYPE: PRT
<213> ORGANISM: Pseudomonas stutzeri

<400> SEQUENCE: 6

Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Arg Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Val Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125

Gly Glu Phe Arg Gly Trp Gln Pro Gln Phe Tyr Gly Thr Gly Leu Asp
    130                 135                 140

Asn Ala Thr Val Gly Ile Leu Gly Met Gly Ala Ile Gly Leu Ala Met
145                 150                 155                 160

Ala Asp Arg Leu Gln Gly Trp Gly Ala Thr Leu Gln Tyr His Ala Ala
                165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Gln His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Arg Leu Ile Asp Pro Ala Leu Leu Ala His Pro Asn Thr Leu
        275                 280                 285

Phe Thr Pro His Ile Gly Ser Ala Val Arg Ala Val Arg Leu Glu Ile
    290                 295                 300

Glu Arg Cys Ala Ala Gln Asn Ile Ile Gln Val Leu Ala Gly Ala Arg
305                 310                 315                 320

Pro Ile Asn Ala Ala Asn Arg Leu Pro Lys Ala Asn Pro Ala Ala Asp
                325                 330                 335

<210> SEQ ID NO 7
<211> LENGTH: 336
<212> TYPE: PRT
<213> ORGANISM: Pseudomonas stutzeri

<400> SEQUENCE: 7

```
Met Leu Pro Lys Leu Val Ile Thr His Arg Val His Glu Glu Ile Leu
 1               5                  10                  15

Gln Leu Leu Ala Pro His Cys Glu Leu Ile Thr Asn Gln Thr Asp Ser
             20                  25                  30

Thr Leu Thr Arg Glu Glu Ile Leu Arg Arg Cys Arg Asp Ala Gln Ala
         35                  40                  45

Met Met Ala Phe Met Pro Asp Arg Val Asp Ala Asp Phe Leu Gln Ala
 50                  55                  60

Cys Pro Glu Leu Arg Val Val Gly Cys Ala Leu Lys Gly Phe Asp Asn
 65                  70                  75                  80

Phe Asp Val Asp Ala Cys Thr Ala Arg Gly Val Trp Leu Thr Phe Val
                 85                  90                  95

Pro Asp Leu Leu Thr Val Pro Thr Ala Glu Leu Ala Ile Gly Leu Ala
             100                 105                 110

Val Gly Leu Gly Arg His Leu Arg Ala Ala Asp Ala Phe Val Arg Ser
         115                 120                 125

Gly Glu Phe Gln Gly Trp Gln Pro Arg Phe Tyr Gly Thr Gly Leu Asp
 130                 135                 140

Asn Ala Thr Val Gly Ile Leu Gly Met Gly Ala Ile Gly Leu Ala Met
145                 150                 155                 160

Ala Asp Arg Leu Gln Gly Trp Gly Ala Thr Leu Gln Tyr His Ala Ala
                 165                 170                 175

Lys Ala Leu Asp Thr Gln Thr Glu Gln Arg Leu Gly Leu Arg Gln Val
             180                 185                 190

Ala Cys Ser Glu Leu Phe Ala Ser Ser Asp Phe Ile Leu Leu Ala Leu
         195                 200                 205

Pro Leu Asn Ala Asp Thr Gln His Leu Val Asn Ala Glu Leu Leu Ala
 210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                 245                 250                 255

Gly Tyr Ala Ala Asp Val Phe Glu Met Glu Asp Trp Ala Arg Ala Asp
             260                 265                 270

Arg Pro Arg Leu Ile Asp Pro Ala Leu Leu Ala His Pro Asn Thr Leu
         275                 280                 285

Phe Thr Pro His Ile Gly Ser Ala Val Arg Ala Val Arg Leu Glu Ile
 290                 295                 300

Glu Arg Cys Ala Ala Gln Asn Ile Ile Gln Val Leu Ala Gly Ala Arg
305                 310                 315                 320

Pro Ile Asn Ala Ala Asn Arg Leu Pro Lys Ala Asn Pro Ala Ala Asp
                 325                 330                 335

<210> SEQ ID NO 8
<211> LENGTH: 336
<212> TYPE: PRT
<213> ORGANISM: Pseudomonas stutzeri

<400> SEQUENCE: 8

Met Leu Pro Lys Leu Val Ile Thr His Arg Val His Glu Glu Ile Leu
 1               5                  10                  15

Gln Leu Leu Ala Pro His Cys Glu Leu Ile Thr Asn Gln Thr Asp Ser
             20                  25                  30

Thr Leu Thr Arg Glu Glu Ile Leu Arg Arg Cys Arg Asp Ala Gln Ala
```

```
                35                  40                  45
Met Met Ala Phe Met Pro Asp Arg Val Asp Ala Asp Phe Leu Gln Ala
             50                  55                  60

Cys Pro Glu Leu Arg Val Val Gly Cys Ala Leu Lys Gly Phe Asp Asn
 65                  70                  75                  80

Phe Asp Val Asp Ala Cys Thr Ala Arg Gly Val Trp Leu Thr Phe Val
                 85                  90                  95

Pro Asp Leu Leu Thr Val Pro Thr Ala Glu Leu Ala Ile Gly Leu Ala
                100                 105                 110

Val Gly Leu Gly Arg His Leu Arg Ala Ala Asp Ala Phe Val Arg Ser
            115                 120                 125

Gly Glu Phe Gln Gly Trp Gln Pro Gln Phe Tyr Gly Thr Gly Leu Asp
        130                 135                 140

Asn Ala Thr Val Gly Phe Leu Gly Met Gly Ala Ile Gly Leu Ala Met
145                 150                 155                 160

Ala Asp Arg Leu Gln Gly Trp Gly Ala Thr Leu Gln Tyr His Ala Ala
                165                 170                 175

Lys Ala Leu Asp Thr Gln Thr Glu Gln Arg Leu Gly Leu Arg Gln Val
                180                 185                 190

Ala Cys Ser Glu Leu Phe Ala Ser Ser Asp Phe Ile Leu Leu Ala Leu
            195                 200                 205

Pro Leu Asn Ala Asp Thr Gln His Leu Val Asn Ala Glu Leu Leu Ala
        210                 215                 220

Leu Val Arg Pro Gly Ala Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
                260                 265                 270

Arg Pro Arg Leu Ile Asp Pro Ala Leu Leu Ala His Pro Asn Thr Leu
            275                 280                 285

Phe Thr Pro His Ile Gly Ser Ala Val Arg Ala Val Arg Leu Glu Ile
        290                 295                 300

Glu Arg Cys Ala Ala Gln Asn Ile Ile Gln Val Leu Ala Gly Ala Arg
305                 310                 315                 320

Pro Ile Asn Ala Ala Asn Arg Leu Pro Lys Ala Asn Pro Ala Ala Asp
                325                 330                 335

<210> SEQ ID NO 9
<211> LENGTH: 336
<212> TYPE: PRT
<213> ORGANISM: Pseudomonas stutzeri

<400> SEQUENCE: 9

Met Leu Pro Lys Leu Val Ile Thr His Arg Val His Glu Glu Ile Leu
 1               5                  10                  15

Gln Leu Leu Ala Pro His Cys Glu Leu Ile Thr Asn Gln Thr Asp Ser
                20                  25                  30

Thr Leu Thr Arg Glu Glu Ile Leu Arg Arg Cys Arg Asp Ala Gln Ala
            35                  40                  45

Met Met Ala Phe Met Pro Asp Arg Val Asp Ala Asp Phe Leu Gln Ala
        50                  55                  60

Cys Pro Glu Leu Arg Val Val Gly Cys Ala Leu Lys Gly Phe Asp Asn
 65                  70                  75                  80
```

```
Phe Asp Val Asp Ala Cys Thr Ala Arg Gly Val Trp Leu Thr Phe Val
                85                  90                  95
Pro Asp Leu Leu Thr Val Pro Thr Ala Glu Leu Ala Ile Gly Leu Ala
            100                 105                 110
Val Gly Leu Gly Arg His Leu Arg Ala Ala Asp Ala Phe Val Arg Ser
        115                 120                 125
Gly Glu Phe Gln Gly Trp Gln Pro Gln Phe Tyr Gly Thr Gly Leu Asp
    130                 135                 140
Asn Ala Thr Val Gly Ile Leu Gly Met Gly Ala Ile Gly Leu Ala Met
145                 150                 155                 160
Ala Asp Arg Leu Gln Gly Trp Gly Ala Thr Leu Gln Tyr His Ala Ala
                165                 170                 175
Lys Ala Leu Asp Thr Gln Thr Glu Gln Arg Leu Gly Leu Arg Gln Val
            180                 185                 190
Ala Cys Ser Glu Leu Phe Ala Ser Ser Asp Phe Ile Leu Leu Ala Leu
        195                 200                 205
Pro Leu Asn Ala Asp Thr Leu His Leu Val Asn Ala Glu Leu Leu Ala
    210                 215                 220
Leu Val Arg Pro Gly Ala Leu Val Asn Pro Cys Arg Gly Ser Val
225                 230                 235                 240
Val Asp Glu Ala Ala Val Leu Ala Ala Leu Glu Arg Gly Gln Leu Gly
                245                 250                 255
Gly Tyr Ala Ala Asp Val Phe Glu Met Glu Asp Trp Ala Arg Ala Asp
            260                 265                 270
Arg Pro Arg Leu Ile Asp Pro Ala Leu Leu Ala His Pro Asn Thr Leu
        275                 280                 285
Phe Thr Pro His Ile Gly Ser Ala Val Arg Ala Val Arg Leu Glu Ile
    290                 295                 300
Glu Arg Cys Ala Ala Gln Asn Ile Ile Gln Val Leu Ala Gly Ala Arg
305                 310                 315                 320
Pro Ile Asn Ala Ala Asn Arg Leu Pro Lys Ala Asn Pro Ala Ala Asp
                325                 330                 335

<210> SEQ ID NO 10
<211> LENGTH: 336
<212> TYPE: PRT
<213> ORGANISM: Pseudomonas stutzeri

<400> SEQUENCE: 10

Met Leu Pro Lys Leu Val Ile Thr His Arg Val His Glu Glu Ile Leu
 1               5                  10                  15
Gln Leu Leu Ala Pro His Cys Glu Leu Ile Thr Asn Gln Thr Asp Ser
            20                  25                  30
Thr Leu Thr Arg Glu Glu Ile Leu Arg Arg Cys Arg Asp Ala Gln Ala
        35                  40                  45
Met Met Ala Phe Met Pro Asp Arg Val Asp Ala Asp Phe Leu Gln Ala
    50                  55                  60
Cys Pro Glu Leu Arg Val Val Gly Cys Ala Leu Lys Gly Phe Asp Asn
65                  70                  75                  80
Phe Asp Val Asp Ala Cys Thr Ala Arg Gly Val Trp Leu Thr Phe Val
                85                  90                  95
Pro Asp Leu Leu Thr Val Pro Thr Ala Glu Leu Ala Ile Gly Leu Ala
            100                 105                 110
Val Gly Leu Gly Arg His Leu Arg Ala Ala Asp Ala Phe Val Arg Ser
        115                 120                 125
```

```
Gly Glu Phe Gln Gly Trp Gln Pro Gln Phe Tyr Gly Thr Gly Leu Asp
            130                 135                 140

Asn Ala Thr Val Gly Ile Leu Met Gly Ala Ile Gly Leu Ala Met
145                 150                 155                 160

Ala Asp Arg Leu Gln Gly Trp Gly Ala Thr Leu Gln Tyr His Ala Ala
                165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
                195                 200                 205

Pro Leu Asn Ala Asp Thr Gln His Leu Val Asn Ala Glu Leu Leu Ala
            210                 215                 220

Leu Val Arg Pro Gly Ala Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
                260                 265                 270

Arg Pro Gln Leu Ile Asp Pro Ala Leu Leu Ala His Pro Asn Thr Leu
            275                 280                 285

Phe Thr Pro His Ile Gly Ser Ala Val Arg Ala Val Arg Leu Glu Ile
            290                 295                 300

Glu Arg Cys Ala Ala Gln Asn Ile Ile Gln Val Leu Ala Gly Ala Arg
305                 310                 315                 320

Pro Ile Asn Ala Ala Asn Arg Leu Pro Lys Ala Asn Pro Ala Ala Asp
                325                 330                 335

<210> SEQ ID NO 11
<211> LENGTH: 336
<212> TYPE: PRT
<213> ORGANISM: Pseudomonas stutzeri

<400> SEQUENCE: 11

Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
                20                  25                  30

Thr Leu Thr Arg Glu Glu Ile Leu Arg Arg Cys Arg Asp Ala Gln Ala
            35                  40                  45

Met Met Ala Phe Met Pro Asp Arg Val Asp Ala Asp Phe Leu Gln Ala
        50                  55                  60

Cys Pro Glu Leu Arg Val Val Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125

Gly Glu Phe Gln Gly Trp Gln Pro Arg Phe Tyr Gly Thr Gly Leu Asp
            130                 135                 140

Asn Ala Thr Val Gly Phe Leu Gly Met Gly Ala Ile Gly Leu Ala Met
145                 150                 155                 160

Ala Asp Arg Leu Gln Gly Trp Gly Ala Thr Leu Gln Tyr His Ala Ala
```

-continued

```
                165                 170                 175
Lys Ala Leu Asp Thr Gln Thr Glu Gln Arg Leu Gly Leu Arg Gln Val
                180                 185                 190

Ala Cys Ser Glu Leu Phe Ala Ser Ser Asp Phe Ile Leu Leu Ala Leu
                195                 200                 205

Pro Leu Asn Ala Asp Thr Leu His Leu Val Asn Ala Glu Leu Leu Ala
            210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Gln Leu Ile Asp Pro Ala Leu Leu Ala His Pro Asn Thr Leu
            275                 280                 285

Phe Thr Pro His Ile Gly Ser Ala Val Arg Ala Val Arg Leu Glu Ile
            290                 295                 300

Glu Arg Cys Ala Ala Gln Asn Ile Ile Gln Val Leu Ala Gly Ala Arg
305                 310                 315                 320

Pro Ile Asn Ala Ala Asn Arg Leu Pro Lys Ala Asn Pro Ala Ala Asp
                325                 330                 335
```

<210> SEQ ID NO 12
<211> LENGTH: 336
<212> TYPE: PRT
<213> ORGANISM: Pseudomonas stutzeri

<400> SEQUENCE: 12

```
Met Leu Pro Lys Leu Val Ile Thr His Arg Val His Glu Glu Ile Leu
  1               5                  10                  15

Gln Leu Leu Ala Pro His Cys Glu Leu Ile Thr Asn Gln Thr Asp Ser
                20                  25                  30

Thr Leu Thr Arg Glu Glu Ile Leu Arg Arg Cys Arg Asp Ala Gln Ala
            35                  40                  45

Met Met Ala Phe Met Pro Asp Arg Val Asp Ala Asp Phe Leu Gln Ala
        50                  55                  60

Cys Pro Glu Leu Arg Val Val Gly Cys Ala Leu Lys Gly Phe Asp Asn
 65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125

Gly Glu Phe Arg Gly Trp Gln Pro Arg Phe Tyr Gly Thr Gly Leu Asp
    130                 135                 140

Asn Ala Thr Val Gly Phe Leu Gly Met Gly Ala Ile Gly Leu Ala Met
145                 150                 155                 160

Ala Asp Arg Leu Gln Gly Trp Gly Ala Thr Leu Gln Tyr His Ala Ala
                165                 170                 175

Lys Ala Leu Asp Thr Gln Thr Glu Gln Arg Leu Gly Leu Arg Gln Val
                180                 185                 190

Ala Cys Ser Glu Leu Phe Ala Ser Ser Asp Phe Ile Leu Leu Ala Leu
                195                 200                 205
```

```
Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                    245                 250                 255

Gly Tyr Ala Ala Asp Val Phe Glu Met Glu Asp Trp Ala Arg Ala Asp
                260                 265                 270

Arg Pro Gln Leu Ile Asp Pro Ala Leu Leu Ala His Pro Asn Thr Leu
            275                 280                 285

Phe Thr Pro His Ile Gly Ser Ala Val Arg Ala Val Arg Leu Glu Ile
    290                 295                 300

Glu Arg Cys Ala Ala Gln Asn Ile Ile Gln Val Leu Ala Gly Ala Arg
305                 310                 315                 320

Pro Ile Asn Ala Ala Asn Arg Leu Pro Lys Ala Asn Pro Ala Ala Asp
                    325                 330                 335

<210> SEQ ID NO 13
<211> LENGTH: 320
<212> TYPE: PRT
<213> ORGANISM: Hyphomicrobium methylovorum

<400> SEQUENCE: 13

Lys Lys Lys Ile Leu Ile Thr Trp Pro Leu Pro Glu Ala Ala Met Ala
  1               5                  10                  15

Arg Ala Arg Glu Ser Tyr Asp Val Ile Ala His Gly Asp Asp Pro Lys
                 20                  25                  30

Ile Thr Ile Asp Glu Met Ile Glu Thr Ala Lys Ser Val Asp Ala Leu
             35                  40                  45

Leu Ile Thr Leu Asn Glu Lys Cys Arg Lys Glu Val Ile Asp Arg Ile
         50                  55                  60

Pro Glu Asn Ile Lys Cys Ile Ser Thr Tyr Ser Ile Gly Phe Asp His
 65                  70                  75                  80

Ile Asp Leu Asp Ala Cys Lys Ala Arg Gly Ile Lys Val Gly Asn Ala
                 85                  90                  95

Pro His Gly Val Thr Val Ala Thr Ala Glu Ile Ala Met Leu Leu Leu
                100                 105                 110

Leu Gly Ser Ala Arg Arg Ala Gly Glu Gly Lys Met Ile Arg Thr
            115                 120                 125

Arg Ser Trp Pro Gly Trp Glu Pro Leu Glu Leu Val Gly Glu Lys Leu
            130                 135                 140

Asp Asn Lys Thr Leu Gly Ile Tyr Gly Phe Gly Ser Ile Gly Gln Ala
145                 150                 155                 160

Leu Ala Lys Arg Ala Gln Gly Phe Asp Met Asp Ile Asp Tyr Phe Asp
                165                 170                 175

Thr His Arg Ala Ser Ser Asp Glu Ala Ser Tyr Gln Ala Thr Phe
            180                 185                 190

His Asp Ser Leu Asp Ser Leu Leu Ser Val Ser Gln Phe Phe Ser Leu
            195                 200                 205

Asn Ala Pro Ser Thr Pro Glu Thr Arg Tyr Phe Phe Asn Lys Ala Thr
    210                 215                 220

Ile Lys Ser Leu Pro Gln Gly Ala Ile Val Val Asn Thr Ala Arg Gly
225                 230                 235                 240

Asp Leu Val Asp Asn Glu Leu Val Val Ala Ala Leu Glu Ala Gly Arg
                245                 250                 255
```

```
Leu Ala Tyr Ala Gly Phe Asp Val Phe Ala Gly Glu Pro Asn Ile Asn
            260                 265                 270

Glu Gly Tyr Tyr Asp Leu Pro Asn Thr Phe Leu Phe Pro His Ile Gly
        275                 280                 285

Ser Ala Ala Thr Gln Ala Arg Glu Asp Met Ala His Gln Ala Asn Asp
            290                 295                 300

Leu Ile Asp Ala Leu Phe Gly Ala Asp Met Ser Tyr Ala Leu Ala
305                 310                 315                 320

<210> SEQ ID NO 14
<211> LENGTH: 409
<212> TYPE: PRT
<213> ORGANISM: Shigella flexneri

<400> SEQUENCE: 14

Ala Lys Val Ser Leu Glu Lys Asp Lys Ile Lys Phe Leu Leu Val Glu
1               5                   10                  15

Gly Val His Gln Lys Ala Leu Glu Ser Leu Arg Ala Ala Gly Tyr Thr
            20                  25                  30

Asn Ile Glu Phe His Lys Gly Ala Leu Asp Asp Glu Gln Leu Lys Glu
        35                  40                  45

Ser Ile Arg Asp Ala His Phe Ile Gly Leu Arg Ser Arg Thr His Leu
    50                  55                  60

Thr Glu Asp Val Ile Asn Ala Ala Glu Lys Leu Val Ala Ile Gly Cys
65                  70                  75                  80

Phe Cys Ile Gly Thr Asn Gln Val Asp Leu Asp Ala Ala Ala Lys Arg
                85                  90                  95

Gly Ile Pro Val Phe Asn Ala Pro Phe Ser Asn Thr Arg Ser Val Ala
            100                 105                 110

Glu Leu Val Ile Gly Glu Leu Leu Leu Leu Arg Gly Val Pro Glu
        115                 120                 125

Ala Asn Ala Lys Ala His Arg Gly Val Trp Asn Lys Leu Ala Ala Gly
    130                 135                 140

Ser Phe Glu Ala Arg Gly Lys Lys Leu Gly Ile Ile Gly Tyr Gly His
145                 150                 155                 160

Ile Gly Thr Gln Leu Gly Ile Leu Ala Glu Ser Leu Gly Met Tyr Val
                165                 170                 175

Tyr Phe Tyr Asp Ile Glu Asn Lys Leu Pro Leu Gly Asn Ala Thr Gln
            180                 185                 190

Val Gln His Leu Ser Asp Leu Leu Asn Met Ser Asp Val Val Ser Leu
        195                 200                 205

His Val Pro Glu Asn Pro Ser Thr Lys Asn Met Met Gly Ala Lys Glu
    210                 215                 220

Ile Ser Leu Met Lys Pro Gly Ser Leu Leu Ile Asn Ala Ser Arg Gly
225                 230                 235                 240

Thr Val Val Asp Ile Pro Ala Leu Cys Asp Ala Leu Ala Ser Lys His
                245                 250                 255

Leu Ala Gly Ala Ala Ile Asp Val Phe Pro Thr Glu Pro Ala Thr Asn
            260                 265                 270

Ser Asp Pro Phe Thr Ser Pro Leu Cys Glu Phe Asp Asn Val Leu Leu
        275                 280                 285

Thr Pro His Ile Gly Gly Ser Thr Gln Glu Ala Gln Glu Asn Ile Gly
    290                 295                 300

Leu Glu Val Ala Gly Lys Leu Ile Lys Tyr Ser Asp Asn Gly Ser Thr
```

```
                305                 310                 315                 320

Leu Ser Ala Val Asn Phe Pro Glu Val Ser Leu Pro Leu His Gly Gly
                325                 330                 335

Arg Arg Leu Met His Ile His Glu Asn Arg Pro Gly Val Leu Thr Ala
                340                 345                 350

Leu Asn Lys Ile Phe Ala Glu Gln Gly Val Asn Ile Ala Ala Gln Tyr
                355                 360                 365

Leu Gln Thr Ser Ala Gln Met Gly Tyr Val Val Ile Asp Ile Glu Ala
                370                 375                 380

Asp Glu Asp Val Ala Glu Lys Ala Leu Gln Ala Met Lys Ala Ile Pro
385                 390                 395                 400

Gly Thr Ile Arg Ala Arg Leu Leu Tyr
                405

<210> SEQ ID NO 15
<211> LENGTH: 337
<212> TYPE: PRT
<213> ORGANISM: Lactobacillus helveticus

<400> SEQUENCE: 15

Met Thr Lys Val Phe Ala Tyr Ala Ile Arg Lys Asp Glu Glu Pro Phe
1               5                   10                  15

Leu Asn Glu Trp Lys Glu Ala His Lys Asp Ile Asp Val Asp Tyr Thr
                20                  25                  30

Asp Lys Leu Leu Thr Pro Glu Thr Ala Lys Leu Ala Lys Gly Ala Asp
            35                  40                  45

Gly Val Val Tyr Gln Gln Leu Asp Tyr Thr Ala Asp Thr Leu Gln
        50                  55                  60

Ala Leu Ala Asp Ala Gly Val Thr Lys Met Ser Leu Arg Asn Val Gly
65                  70                  75                  80

Val Asp Asn Ile Asp Met Asp Lys Ala Lys Glu Leu Gly Phe Gln Ile
                85                  90                  95

Thr Asn Val Pro Val Tyr Ser Pro Asn Ala Ile Ala Glu His Ala Ala
                100                 105                 110

Ile Gln Ala Ala Arg Val Leu Arg Gln Asp Lys Arg Met Asp Glu Lys
            115                 120                 125

Met Ala Lys Arg Asp Leu Arg Trp Ala Pro Thr Ile Gly Arg Glu Val
        130                 135                 140

Arg Asp Gln Val Val Gly Val Val Gly Thr Gly His Ile Gly Gln Val
145                 150                 155                 160

Phe Met Arg Ile Met Glu Gly Phe Gly Ala Lys Val Ile Ala Tyr Asp
                165                 170                 175

Ile Phe Lys Asn Pro Glu Leu Glu Lys Lys Gly Tyr Tyr Val Asp Ser
                180                 185                 190

Leu Asp Asp Leu Tyr Lys Gln Ala Asp Val Ile Ser Leu His Val Pro
            195                 200                 205

Asp Val Pro Ala Asn Val His Met Ile Asn Asp Lys Ser Ile Ala Glu
        210                 215                 220

Met Lys Asp Gly Val Val Ile Val Asn Cys Ser Arg Gly Arg Leu Val
225                 230                 235                 240

Asp Thr Asp Ala Val Ile Arg Gly Leu Asp Ser Gly Lys Ile Phe Gly
                245                 250                 255

Phe Val Met Asp Thr Tyr Glu Asp Glu Val Gly Val Phe Asn Lys Asp
                260                 265                 270
```

```
Trp Glu Gly Lys Glu Phe Pro Asp Lys Arg Leu Ala Asp Leu Ile Asp
        275                 280                 285

Arg Pro Asn Val Leu Val Thr Pro His Thr Ala Phe Tyr Thr Thr His
        290                 295                 300

Ala Val Arg Asn Met Val Val Lys Ala Phe Asn Asn Asn Leu Lys Leu
305                 310                 315                 320

Ile Asn Gly Glu Lys Pro Asp Ser Pro Val Ala Leu Asn Lys Asn Lys
                325                 330                 335

Phe

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Consensus
      binding motif
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)
<223> OTHER INFORMATION: Variable amino acid
<220> FEATURE:
<221> NAME/KEY: MOD_RES
<222> LOCATION: (7)..(8)
<223> OTHER INFORMATION: Variable amino acid

<400> SEQUENCE: 16

Gly Xaa Xaa Gly Xaa Gly Xaa Xaa Gly
 1               5

<210> SEQ ID NO 17
<211> LENGTH: 9
<212> TYPE: PRT
<213> ORGANISM: Pseudomonas stutzeri

<400> SEQUENCE: 17

Asp Trp Ala Arg Ala Asp Arg Pro Arg
 1               5

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 18
ctgcagtacc acgbggcgaa ggctctg                                    27

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 19
cagagccttc gccvcgtggt actgcag                                    27

<210> SEQ ID NO 20
<211> LENGTH: 27
<212> TYPE: DNA
```

```
<213> ORGANISM: Artificial Sequence
<220> FEATURE:
<223> OTHER INFORMATION: Description of Artificial Sequence: Primer

<400> SEQUENCE: 20
cagtaccacg agcggaaggc tctggat                                           27

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 21
atccagagcc ttccgctcgt ggtactg                                           27

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 22
ctgcagtacc acgcgcggaa ggctctggat ac                                     32

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 23
gtatccatag ccttccgcgc gtggtactgc ag                                     32

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 24
tttttggatg gaggaattca tatg                                              24

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 25
cgggaagacg tacggggtat acatgt                                            26

<210> SEQ ID NO 26
<211> LENGTH: 1011
<212> TYPE: DNA
<213> ORGANISM: Pseudomonas stutzeri
<220> FEATURE:
<221> NAME/KEY: CDS
<222> LOCATION: (1)..(1008)

<400> SEQUENCE: 26
```

```
atg ctg ccg aaa ctc gtt ata act cac cga gta cac gaa gag atc ctg      48
Met Leu Pro Lys Leu Val Ile Thr His Arg Val His Glu Glu Ile Leu
  1               5                  10                  15 caa ctg ctg gcg cca cat tgc gag ctg ata acc aac cag acc gac agc      96
Gln Leu Leu Ala Pro His Cys Glu Leu Ile Thr Asn Gln Thr Asp Ser
             20                  25                  30 acg ctg acg cgc gag gaa att ctg cgc cgc tgt cgc gat gct cag gcg     144
Thr Leu Thr Arg Glu Glu Ile Leu Arg Arg Cys Arg Asp Ala Gln Ala
         35                  40                  45 atg atg gcg ttc atg ccc gat cgg gtc gat gca gac ttt ctt caa gcc     192
Met Met Ala Phe Met Pro Asp Arg Val Asp Ala Asp Phe Leu Gln Ala
     50                  55                  60 tgc cct gag ctg cgt gta gtc ggc tgc gcg ctc aag ggc ttc gac aat     240
Cys Pro Glu Leu Arg Val Val Gly Cys Ala Leu Lys Gly Phe Asp Asn
 65                  70                  75                  80 ttc gat gtg gac gcc tgt act gcc cgc ggg gtc tgg ctg acc ttc gtg     288
Phe Asp Val Asp Ala Cys Thr Ala Arg Gly Val Trp Leu Thr Phe Val
                 85                  90                  95 cct gat ctg ttg acg gtc ccg act gcc gag ctg gcg atc gga ctg gcg     336
Pro Asp Leu Leu Thr Val Pro Thr Ala Glu Leu Ala Ile Gly Leu Ala
            100                 105                 110 gtg ggg ctg ggg cgg cat ctg cgg gca gca gat gcg ttc gtc cgc tct     384
Val Gly Leu Gly Arg His Leu Arg Ala Ala Asp Ala Phe Val Arg Ser
        115                 120                 125 ggc gag ttc cag ggc tgg caa cca cag ttc tac ggc acg ggg ctg gat     432
Gly Glu Phe Gln Gly Trp Gln Pro Gln Phe Tyr Gly Thr Gly Leu Asp
    130                 135                 140 aac gct acg gtc ggc atc ctt ggc atg ggc gcc atc gga ctg gcc atg     480
Asn Ala Thr Val Gly Ile Leu Gly Met Gly Ala Ile Gly Leu Ala Met
145                 150                 155                 160 gct gat cgc ttg cag gga tgg ggc gcg acc ctg cag tac cac gcg gcg     528
Ala Asp Arg Leu Gln Gly Trp Gly Ala Thr Leu Gln Tyr His Ala Ala
                165                 170                 175 aag gct ctg gat aca caa acc gag caa cgg ctc ggc ctg cgc cag gtg     576
Lys Ala Leu Asp Thr Gln Thr Glu Gln Arg Leu Gly Leu Arg Gln Val
            180                 185                 190 gcg tgc agc gaa ctc ttc gcc agc tcg gac ttc atc ctg ctg gcg ctt     624
Ala Cys Ser Glu Leu Phe Ala Ser Ser Asp Phe Ile Leu Leu Ala Leu
        195                 200                 205 ccc ttg aat gcc gat acc cag cat ctg gtc aac gcc gag ctg ctt gcc     672
Pro Leu Asn Ala Asp Thr Gln His Leu Val Asn Ala Glu Leu Leu Ala
    210                 215                 220 ctc gta cgg ccg ggc gct ctg ctt gta aac ccc tgt cgt ggt tcg gta     720
Leu Val Arg Pro Gly Ala Leu Leu Val Asn Pro Cys Arg Gly Ser Val
225                 230                 235                 240 gtg gat gaa gcc gcc gtg ctc gcg gcg ctt gag cga ggc cag ctc ggc     768
Val Asp Glu Ala Ala Val Leu Ala Ala Leu Glu Arg Gly Gln Leu Gly
                245                 250                 255 ggg tat gcg gcg gat gta ttc gaa atg gaa gac tgg gct cgc gcg gac     816
Gly Tyr Ala Ala Asp Val Phe Glu Met Glu Asp Trp Ala Arg Ala Asp
            260                 265                 270 cgg ccg cgg ctg atc gat cct gcg ctg ctc gcg cat ccg aat acg ctg     864
Arg Pro Arg Leu Ile Asp Pro Ala Leu Leu Ala His Pro Asn Thr Leu
        275                 280                 285 ttc act ccg cac ata ggg tcg gca gtg cgc gcg gtg cgc ctg gag att     912
Phe Thr Pro His Ile Gly Ser Ala Val Arg Ala Val Arg Leu Glu Ile
    290                 295                 300 gaa cgt tgt gca gcg cag aac atc atc cag gta ttg gca ggt gcg cgc     960
Glu Arg Cys Ala Ala Gln Asn Ile Ile Gln Val Leu Ala Gly Ala Arg
305                 310                 315                 320
```

```
cca atc aac gct gcg aac cgt ctg ccc aag gcc aat cct gcc gca gac      1008
Pro Ile Asn Ala Ala Asn Arg Leu Pro Lys Ala Asn Pro Ala Ala Asp
                325                 330                 335 tga                                                                   1011

<210> SEQ ID NO 27
<211> LENGTH: 1011
<212> TYPE: DNA
<213> ORGANISM: Pseudomonas stutzeri
<220> FEATURE:
<221> NAME/KEY: CDS
<222> LOCATION: (1)..(1008)

<400> SEQUENCE: 27 atg ctg ccg aaa ctc gtt ata act cac cga gta cac gaa gag atc ctg        48
Met Leu Pro Lys Leu Val Ile Thr His Arg Val His Glu Glu Ile Leu
  1               5                  10                  15 caa ctg ctg gcg cca cat tgc gag ctg ata acc aac cag acc gac agc        96
Gln Leu Leu Ala Pro His Cys Glu Leu Ile Thr Asn Gln Thr Asp Ser
             20                  25                  30 acg ctg acg cgc gag gaa att ctg cgc cgc tgt cgc gat gct cag gcg       144
Thr Leu Thr Arg Glu Glu Ile Leu Arg Arg Cys Arg Asp Ala Gln Ala
         35                  40                  45 atg atg gcg ttc atg ccc gat cgg gtc gat gca gac ttt ctt caa gcc       192
Met Met Ala Phe Met Pro Asp Arg Val Asp Ala Asp Phe Leu Gln Ala
 50                  55                  60 tgc cct gag ctg cgt gta gtc ggc tgc gcg ctc aag ggc ttc gac aat       240
Cys Pro Glu Leu Arg Val Val Gly Cys Ala Leu Lys Gly Phe Asp Asn
 65                  70                  75                  80 ttc gat gtg gac gcc tgt act gcc cgc ggg gtc tgg ctg acc ttc gtg       288
Phe Asp Val Asp Ala Cys Thr Ala Arg Gly Val Trp Leu Thr Phe Val
                 85                  90                  95 cct gat ctg ttg acg gtc ccg act gcc gag ctg gcg atc gga ctg gcg       336
Pro Asp Leu Leu Thr Val Pro Thr Ala Glu Leu Ala Ile Gly Leu Ala
            100                 105                 110 gtg ggg ctg ggg cgg cat ctg cgg gca gca gat gcg ttc gtc cgc tct       384
Val Gly Leu Gly Arg His Leu Arg Ala Ala Asp Ala Phe Val Arg Ser
        115                 120                 125 ggc gag ttc cgg ggc tgg caa cca cag ttc tac ggc acg ggg ctg gat       432
Gly Glu Phe Arg Gly Trp Gln Pro Gln Phe Tyr Gly Thr Gly Leu Asp
    130                 135                 140 aac gct acg gtc ggc atc ctt ggc atg ggc gcc atc gga ctg gcc atg       480
Asn Ala Thr Val Gly Ile Leu Gly Met Gly Ala Ile Gly Leu Ala Met
145                 150                 155                 160 gct gat cgc ttg cag gga tgg ggc gcg acc ctg cag tac cac gcg gcg       528
Ala Asp Arg Leu Gln Gly Trp Gly Ala Thr Leu Gln Tyr His Ala Ala
                165                 170                 175 aag gct ctg gat aca caa acc gag caa cgg ctc ggc ctg cgc cag gtg       576
Lys Ala Leu Asp Thr Gln Thr Glu Gln Arg Leu Gly Leu Arg Gln Val
            180                 185                 190 gcg tgc agc gaa ctc ttc gcc agc tcg gac ttc atc ctg ctg gcg ctt       624
Ala Cys Ser Glu Leu Phe Ala Ser Ser Asp Phe Ile Leu Leu Ala Leu
        195                 200                 205 ccc ttg aat gcc gat acc cag cat ctg gtc aac gcc gag ctg ctt gcc       672
Pro Leu Asn Ala Asp Thr Gln His Leu Val Asn Ala Glu Leu Leu Ala
    210                 215                 220 ctc gta cgg ccg ggc gct ctg ctt gta aac ccc tgt cgt ggt tcg gta       720
Leu Val Arg Pro Gly Ala Leu Leu Val Asn Pro Cys Arg Gly Ser Val
225                 230                 235                 240 gtg gat gaa gcc gcc gtg ctc gcg gcg ctt gag cga ggc cag ctc ggc       768
```

```
                                                                                          -continued Val Asp Glu Ala Ala Val Leu Ala Ala Leu Glu Arg Gly Gln Leu Gly
                245                 250                 255 ggg tat gcg gcg gat gta ttc gaa atg gaa gac tgg gct cgc gcg gac      816
Gly Tyr Ala Ala Asp Val Phe Glu Met Glu Asp Trp Ala Arg Ala Asp
            260                 265                 270 cgg ccg cgg ctg atc gat cct gcg ctg ctc gcg cat ccg aat acg ctg      864
Arg Pro Arg Leu Ile Asp Pro Ala Leu Leu Ala His Pro Asn Thr Leu
        275                 280                 285 ttc act ccg cac ata ggg tcg gca gtg cgc gcg gtg cgc ctg gag att      912
Phe Thr Pro His Ile Gly Ser Ala Val Arg Ala Val Arg Leu Glu Ile
    290                 295                 300 gaa cgt tgt gca gcg cag aac atc atc cag gta ttg gca ggt gcg cgc      960
Glu Arg Cys Ala Ala Gln Asn Ile Ile Gln Val Leu Ala Gly Ala Arg
305                 310                 315                 320 cca atc aac gct gcg aac cgt ctg ccc aag gcc aat cct gcc gca gac     1008
Pro Ile Asn Ala Ala Asn Arg Leu Pro Lys Ala Asn Pro Ala Ala Asp
                325                 330                 335 tga                                                                 1011

<210> SEQ ID NO 28
<211> LENGTH: 1011
<212> TYPE: DNA
<213> ORGANISM: Pseudomonas stutzeri
<220> FEATURE:
<221> NAME/KEY: CDS
<222> LOCATION: (1)..(1008)

<400> SEQUENCE: 28 atg ctg ccg aaa ctc gtt ata act cac cga gta cac gaa gag atc ctg       48
Met Leu Pro Lys Leu Val Ile Thr His Arg Val His Glu Glu Ile Leu
 1               5                  10                  15 caa ctg ctg gcg cca cat tgc gag ctg ata acc aac cag acc gac agc       96
Gln Leu Leu Ala Pro His Cys Glu Leu Ile Thr Asn Gln Thr Asp Ser
            20                  25                  30 acg ctg acg cgc gag gaa att ctg cgc cgc tgt cgc gat gct cag gcg      144
Thr Leu Thr Arg Glu Glu Ile Leu Arg Arg Cys Arg Asp Ala Gln Ala
        35                  40                  45 atg atg gcg ttc atg ccc gat cgg gtc gat gca gac ttt ctt caa gcc      192
Met Met Ala Phe Met Pro Asp Arg Val Asp Ala Asp Phe Leu Gln Ala
    50                  55                  60 tgc cct gag ctg cgt gta gtc ggc tgc gcg ctc aag ggc ttc gac aat      240
Cys Pro Glu Leu Arg Val Val Gly Cys Ala Leu Lys Gly Phe Asp Asn
65                  70                  75                  80 ttc gat gtg gac gcc tgt act gcc cgc ggg gtc tgg ctg acc ttc gtg      288
Phe Asp Val Asp Ala Cys Thr Ala Arg Gly Val Trp Leu Thr Phe Val
                85                  90                  95 cct gat ctg ttg acg gtc ccg act gcc gag ctg gcg atc gga ctg gcg      336
Pro Asp Leu Leu Thr Val Pro Thr Ala Glu Leu Ala Ile Gly Leu Ala
            100                 105                 110 gtg ggg ctg ggg cgg cat ctg cgg gca gca gat gcg ttc gtc cgc tct      384
Val Gly Leu Gly Arg His Leu Arg Ala Ala Asp Ala Phe Val Arg Ser
        115                 120                 125 ggc gag ttc cag ggc tgg caa cca cgg ttc tac ggc acg ggg ctg gat      432
Gly Glu Phe Gln Gly Trp Gln Pro Arg Phe Tyr Gly Thr Gly Leu Asp
    130                 135                 140 aac gct acg gtc ggc atc ctt ggc atg ggc gcc atc gga ctg gcc atg      480
Asn Ala Thr Val Gly Ile Leu Gly Met Gly Ala Ile Gly Leu Ala Met
145                 150                 155                 160 gct gat cgc ttg cag gga tgg ggc gcg acc ctg cag tac cac gcg gcg      528
Ala Asp Arg Leu Gln Gly Trp Gly Ala Thr Leu Gln Tyr His Ala Ala
                165                 170                 175
```

-continued

```
aag gct ctg gat aca caa acc gag caa cgg ctc ggc ctg cgc cag gtg      576
Lys Ala Leu Asp Thr Gln Thr Glu Gln Arg Leu Gly Leu Arg Gln Val
            180                 185                 190 gcg tgc agc gaa ctc ttc gcc agc tcg gac ttc atc ctg ctg gcg ctt      624
Ala Cys Ser Glu Leu Phe Ala Ser Ser Asp Phe Ile Leu Leu Ala Leu
        195                 200                 205 ccc ttg aat gcc gat acc cag cat ctg gtc aac gcc gag ctg ctt gcc      672
Pro Leu Asn Ala Asp Thr Gln His Leu Val Asn Ala Glu Leu Leu Ala
    210                 215                 220 ctc gta cgg ccg ggc gct ctg ctt gta aac ccc tgt cgt ggt tcg gta      720
Leu Val Arg Pro Gly Ala Leu Leu Val Asn Pro Cys Arg Gly Ser Val
225                 230                 235                 240 gtg gat gaa gcc gcc gtg ctc gcg gcg ctt gag cga ggc cag ctc ggc      768
Val Asp Glu Ala Ala Val Leu Ala Ala Leu Glu Arg Gly Gln Leu Gly
                245                 250                 255 ggg tat gcg gcg gat gta ttc gaa atg gaa gac tgg gct cgc gcg gac      816
Gly Tyr Ala Ala Asp Val Phe Glu Met Glu Asp Trp Ala Arg Ala Asp
            260                 265                 270 cgg ccg cgg ctg atc gat cct gcg ctg ctc gcg cat ccg aat acg ctg      864
Arg Pro Arg Leu Ile Asp Pro Ala Leu Leu Ala His Pro Asn Thr Leu
        275                 280                 285 ttc act ccg cac ata ggg tcg gca gtg cgc gcg gtg cgc ctg gag att      912
Phe Thr Pro His Ile Gly Ser Ala Val Arg Ala Val Arg Leu Glu Ile
    290                 295                 300 gaa cgt tgt gca gcg cag aac atc atc cag gta ttg gca ggt gcg cgc      960
Glu Arg Cys Ala Ala Gln Asn Ile Ile Gln Val Leu Ala Gly Ala Arg
305                 310                 315                 320 cca atc aac gct gcg aac cgt ctg ccc aag gcc aat cct gcc gca gac     1008
Pro Ile Asn Ala Ala Asn Arg Leu Pro Lys Ala Asn Pro Ala Ala Asp
                325                 330                 335 tga                                                                 1011

<210> SEQ ID NO 29
<211> LENGTH: 1011
<212> TYPE: DNA
<213> ORGANISM: Pseudomonas stutzeri
<220> FEATURE:
<221> NAME/KEY: CDS
<222> LOCATION: (1)..(1008)

<400> SEQUENCE: 29 atg ctg ccg aaa ctc gtt ata act cac cga gta cac gaa gag atc ctg       48
Met Leu Pro Lys Leu Val Ile Thr His Arg Val His Glu Glu Ile Leu
  1               5                  10                  15 caa ctg ctg gcg cca cat tgc gag ctg ata acc aac cag acc gac agc       96
Gln Leu Leu Ala Pro His Cys Glu Leu Ile Thr Asn Gln Thr Asp Ser
            20                  25                  30 acg ctg acg cgc gag gaa att ctg cgc cgc tgt cgc gat gct cag gcg      144
Thr Leu Thr Arg Glu Glu Ile Leu Arg Arg Cys Arg Asp Ala Gln Ala
        35                  40                  45 atg atg gcg ttc atg ccc gat cgg gtc gat gca gac ttt ctt caa gcc      192
Met Met Ala Phe Met Pro Asp Arg Val Asp Ala Asp Phe Leu Gln Ala
    50                  55                  60 tgc cct gag ctg cgt gta gtc ggc tgc gcg ctc aag ggc ttc gac aat      240
Cys Pro Glu Leu Arg Val Val Gly Cys Ala Leu Lys Gly Phe Asp Asn
65                  70                  75                  80 ttc gat gtg gac gcc tgt act gcc cgc ggg gtc tgg ctg acc ttc gtg      288
Phe Asp Val Asp Ala Cys Thr Ala Arg Gly Val Trp Leu Thr Phe Val
                85                  90                  95 cct gat ctg ttg acg gtc ccg act gcc gag ctg gcg atc gga ctg gcg      336
```

```
            Pro Asp Leu Leu Thr Val Pro Thr Ala Glu Leu Ala Ile Gly Leu Ala
                        100                 105                 110 gtg ggg ctg ggg cgg cat ctg cgg gca gca gat gcg ttc gtc cgc tct            384
Val Gly Leu Gly Arg His Leu Arg Ala Ala Asp Ala Phe Val Arg Ser
            115                 120                 125 ggc gag ttc cag ggc tgg caa cca cag ttc tac ggc acg ggg ctg gat            432
Gly Glu Phe Gln Gly Trp Gln Pro Gln Phe Tyr Gly Thr Gly Leu Asp
130                 135                 140 aac gct acg gtc ggc ttc ctt ggc atg ggc gcc atc gga ctg gcc atg            480
Asn Ala Thr Val Gly Phe Leu Gly Met Gly Ala Ile Gly Leu Ala Met
145                 150                 155                 160 gct gat cgc ttg cag gga tgg ggc gcg acc ctg cag tac cac gcg gcg            528
Ala Asp Arg Leu Gln Gly Trp Gly Ala Thr Leu Gln Tyr His Ala Ala
                165                 170                 175 aag gct ctg gat aca caa acc gag caa cgg ctc ggc ctg cgc cag gtg            576
Lys Ala Leu Asp Thr Gln Thr Glu Gln Arg Leu Gly Leu Arg Gln Val
            180                 185                 190 gcg tgc agc gaa ctc ttc gcc agc tcg gac ttc atc ctg ctg gcg ctt            624
Ala Cys Ser Glu Leu Phe Ala Ser Ser Asp Phe Ile Leu Leu Ala Leu
        195                 200                 205 ccc ttg aat gcc gat acc cag cat ctg gtc aac gcc gag ctg ctt gcc            672
Pro Leu Asn Ala Asp Thr Gln His Leu Val Asn Ala Glu Leu Leu Ala
210                 215                 220 ctc gta cgg ccg ggc gct ctg ctt gta aac ccc tgt cgt ggt tcg gta            720
Leu Val Arg Pro Gly Ala Leu Leu Val Asn Pro Cys Arg Gly Ser Val
225                 230                 235                 240 gtg gat gaa gcc gcc gtg ctc gcg gcg ctt gag cga ggc cag ctc ggc            768
Val Asp Glu Ala Ala Val Leu Ala Ala Leu Glu Arg Gly Gln Leu Gly
                245                 250                 255 ggg tat gcg gcg gat gta ttc gaa atg gaa gac tgg gct cgc gcg gac            816
Gly Tyr Ala Ala Asp Val Phe Glu Met Glu Asp Trp Ala Arg Ala Asp
            260                 265                 270 cgg ccg cgg ctg atc gat cct gcg ctg ctc gcg cat ccg aat acg ctg            864
Arg Pro Arg Leu Ile Asp Pro Ala Leu Leu Ala His Pro Asn Thr Leu
        275                 280                 285 ttc act ccg cac ata ggg tcg gca gtg cgc gcg gtg cgc ctg gag att            912
Phe Thr Pro His Ile Gly Ser Ala Val Arg Ala Val Arg Leu Glu Ile
290                 295                 300 gaa cgt tgt gca gcg cag aac atc atc cag gta ttg gca ggt gcg cgc            960
Glu Arg Cys Ala Ala Gln Asn Ile Ile Gln Val Leu Ala Gly Ala Arg
305                 310                 315                 320 cca atc aac gct gcg aac cgt ctg ccc aag gcc aat cct gcc gca gac           1008
Pro Ile Asn Ala Ala Asn Arg Leu Pro Lys Ala Asn Pro Ala Ala Asp
                325                 330                 335 tga                                                                        1011
```

<210> SEQ ID NO 30
<211> LENGTH: 1011
<212> TYPE: DNA
<213> ORGANISM: Pseudomonas stutzeri
<220> FEATURE:
<221> NAME/KEY: CDS
<222> LOCATION: (1)..(1008)

<400> SEQUENCE: 30

```
atg ctg ccg aaa ctc gtt ata act cac cga gta cac gaa gag atc ctg             48
Met Leu Pro Lys Leu Val Ile Thr His Arg Val His Glu Glu Ile Leu
1               5                   10                  15 caa ctg ctg gcg cca cat tgc gag ctg ata acc aac cag acc gac agc             96
Gln Leu Leu Ala Pro His Cys Glu Leu Ile Thr Asn Gln Thr Asp Ser
            20                  25                  30
```

-continued

```
acg ctg acg cgc gag gaa att ctg cgc cgc tgt cgc gat gct cag gcg      144
Thr Leu Thr Arg Glu Glu Ile Leu Arg Arg Cys Arg Asp Ala Gln Ala
         35                  40                  45 atg atg gcg ttc atg ccc gat cgg gtc gat gca gac ttt ctt caa gcc      192
Met Met Ala Phe Met Pro Asp Arg Val Asp Ala Asp Phe Leu Gln Ala
 50                  55                  60 tgc cct gag ctg cgt gta gtc ggc tgc gcg ctc aag ggc ttc gac aat      240
Cys Pro Glu Leu Arg Val Val Gly Cys Ala Leu Lys Gly Phe Asp Asn
 65                  70                  75                  80 ttc gat gtg gac gcc tgt act gcc cgc ggg gtc tgg ctg acc ttc gtg      288
Phe Asp Val Asp Ala Cys Thr Ala Arg Gly Val Trp Leu Thr Phe Val
                 85                  90                  95 cct gat ctg ttg acg gtc ccg act gcc gag ctg gcg atc gga ctg gcg      336
Pro Asp Leu Leu Thr Val Pro Thr Ala Glu Leu Ala Ile Gly Leu Ala
            100                 105                 110 gtg ggg ctg ggg cgg cat ctg cgg gca gca gat gcg ttc gtc cgc tct      384
Val Gly Leu Gly Arg His Leu Arg Ala Ala Asp Ala Phe Val Arg Ser
        115                 120                 125 ggc gag ttc cag ggc tgg caa cca cag ttc tac ggc acg ggg ctg gat      432
Gly Glu Phe Gln Gly Trp Gln Pro Gln Phe Tyr Gly Thr Gly Leu Asp
130                 135                 140 aac gct acg gtc ggc atc ctt ggc atg ggc gcc atc gga ctg gcc atg      480
Asn Ala Thr Val Gly Ile Leu Gly Met Gly Ala Ile Gly Leu Ala Met
145                 150                 155                 160 gct gat cgc ttg cag gga tgg ggc gcg acc ctg cag tac cac gcg gcg      528
Ala Asp Arg Leu Gln Gly Trp Gly Ala Thr Leu Gln Tyr His Ala Ala
                165                 170                 175 aag gct ctg gat aca caa acc gag caa cgg ctc ggc ctg cgc cag gtg      576
Lys Ala Leu Asp Thr Gln Thr Glu Gln Arg Leu Gly Leu Arg Gln Val
            180                 185                 190 gcg tgc agc gaa ctc ttc gcc agc tcg gac ttc atc ctg ctg gcg ctt      624
Ala Cys Ser Glu Leu Phe Ala Ser Ser Asp Phe Ile Leu Leu Ala Leu
        195                 200                 205 ccc ttg aat gcc gat acc ctg cat ctg gtc aac gcc gag ctg ctt gcc      672
Pro Leu Asn Ala Asp Thr Leu His Leu Val Asn Ala Glu Leu Leu Ala
210                 215                 220 ctc gta cgg ccg ggc gct ctg ctt gta aac ccc tgt cgt ggt tcg gta      720
Leu Val Arg Pro Gly Ala Leu Leu Val Asn Pro Cys Arg Gly Ser Val
225                 230                 235                 240 gtg gat gaa gcc gcc gtg ctc gcg gcg ctt gag cga ggc cag ctc ggc      768
Val Asp Glu Ala Ala Val Leu Ala Ala Leu Glu Arg Gly Gln Leu Gly
                245                 250                 255 ggg tat gcg gcg gat gta ttc gaa atg gaa gac tgg gct cgc gcg gac      816
Gly Tyr Ala Ala Asp Val Phe Glu Met Glu Asp Trp Ala Arg Ala Asp
            260                 265                 270 cgg ccg cgg ctg atc gat cct gcg ctg ctc gcg cat ccg aat acg ctg      864
Arg Pro Arg Leu Ile Asp Pro Ala Leu Leu Ala His Pro Asn Thr Leu
        275                 280                 285 ttc act ccg cac ata ggg tcg gca gtg cgc gcg gtg cgc ctg gag att      912
Phe Thr Pro His Ile Gly Ser Ala Val Arg Ala Val Arg Leu Glu Ile
290                 295                 300 gaa cgt tgt gca gcg cag aac atc atc cag gta ttg gca ggt gcg cgc      960
Glu Arg Cys Ala Ala Gln Asn Ile Ile Gln Val Leu Ala Gly Ala Arg
305                 310                 315                 320 cca atc aac gct gcg aac cgt ctg ccc aag gcc aat cct gcc gca gac     1008
Pro Ile Asn Ala Ala Asn Arg Leu Pro Lys Ala Asn Pro Ala Ala Asp
                325                 330                 335 tga                                                                 1011
```

-continued

<210> SEQ ID NO 31
<211> LENGTH: 1011
<212> TYPE: DNA
<213> ORGANISM: Pseudomonas stutzeri
<220> FEATURE:
<221> NAME/KEY: CDS
<222> LOCATION: (1)..(1008)

<400> SEQUENCE: 31

| | | | | | | | | | | | | | | | | |
|---|---|---|---|---|---|---|---|---|---|---|---|---|---|---|---|---|
| atg | ctg | ccg | aaa | ctc | gtt | ata | act | cac | cga | gta | cac | gaa | gag | atc | ctg | 48 |
| Met | Leu | Pro | Lys | Leu | Val | Ile | Thr | His | Arg | Val | His | Glu | Glu | Ile | Leu | |
| 1 | | | | 5 | | | | | 10 | | | | | 15 | | |

| caa | ctg | ctg | gcg | cca | cat | tgc | gag | ctg | ata | acc | aac | cag | acc | gac | agc | 96 |
|---|---|---|---|---|---|---|---|---|---|---|---|---|---|---|---|---|
| Gln | Leu | Leu | Ala | Pro | His | Cys | Glu | Leu | Ile | Thr | Asn | Gln | Thr | Asp | Ser | |
| | | | 20 | | | | | 25 | | | | | 30 | | | |

| acg | ctg | acg | cgc | gag | gaa | att | ctg | cgc | cgc | tgt | cgc | gat | gct | cag | gcg | 144 |
|---|---|---|---|---|---|---|---|---|---|---|---|---|---|---|---|---|
| Thr | Leu | Thr | Arg | Glu | Glu | Ile | Leu | Arg | Arg | Cys | Arg | Asp | Ala | Gln | Ala | |
| | | 35 | | | | | 40 | | | | | 45 | | | | |

| atg | atg | gcg | ttc | atg | ccc | gat | cgg | gtc | gat | gca | gac | ttt | ctt | caa | gcc | 192 |
|---|---|---|---|---|---|---|---|---|---|---|---|---|---|---|---|---|
| Met | Met | Ala | Phe | Met | Pro | Asp | Arg | Val | Asp | Ala | Asp | Phe | Leu | Gln | Ala | |
| 50 | | | | | 55 | | | | | 60 | | | | | | |

| tgc | cct | gag | ctg | cgt | gta | gtc | ggc | tgc | gcg | ctc | aag | ggc | ttc | gac | aat | 240 |
|---|---|---|---|---|---|---|---|---|---|---|---|---|---|---|---|---|
| Cys | Pro | Glu | Leu | Arg | Val | Val | Gly | Cys | Ala | Leu | Lys | Gly | Phe | Asp | Asn | |
| 65 | | | | 70 | | | | | 75 | | | | | 80 | | |

| ttc | gat | gtg | gac | gcc | tgt | act | gcc | cgc | ggg | gtc | tgg | ctg | acc | ttc | gtg | 288 |
|---|---|---|---|---|---|---|---|---|---|---|---|---|---|---|---|---|
| Phe | Asp | Val | Asp | Ala | Cys | Thr | Ala | Arg | Gly | Val | Trp | Leu | Thr | Phe | Val | |
| | | | | 85 | | | | | 90 | | | | | 95 | | |

| cct | gat | ctg | ttg | acg | gtc | ccg | act | gcc | gag | ctg | gcg | atc | gga | ctg | gcg | 336 |
|---|---|---|---|---|---|---|---|---|---|---|---|---|---|---|---|---|
| Pro | Asp | Leu | Leu | Thr | Val | Pro | Thr | Ala | Glu | Leu | Ala | Ile | Gly | Leu | Ala | |
| | | | | 100 | | | | | 105 | | | | | 110 | | |

| gtg | ggg | ctg | ggg | cgg | cat | ctg | cgg | gca | gca | gat | gcg | ttc | gtc | cgc | tct | 384 |
|---|---|---|---|---|---|---|---|---|---|---|---|---|---|---|---|---|
| Val | Gly | Leu | Gly | Arg | His | Leu | Arg | Ala | Ala | Asp | Ala | Phe | Val | Arg | Ser | |
| | | 115 | | | | | 120 | | | | | 125 | | | | |

| ggc | gag | ttc | cag | ggc | tgg | caa | cca | cag | ttc | tac | ggc | acg | ggg | ctg | gat | 432 |
|---|---|---|---|---|---|---|---|---|---|---|---|---|---|---|---|---|
| Gly | Glu | Phe | Gln | Gly | Trp | Gln | Pro | Gln | Phe | Tyr | Gly | Thr | Gly | Leu | Asp | |
| 130 | | | | | 135 | | | | | 140 | | | | | | |

| aac | gct | acg | gtc | ggc | atc | ctt | ggc | atg | ggc | gcc | atc | gga | ctg | gcc | atg | 480 |
|---|---|---|---|---|---|---|---|---|---|---|---|---|---|---|---|---|
| Asn | Ala | Thr | Val | Gly | Ile | Leu | Gly | Met | Gly | Ala | Ile | Gly | Leu | Ala | Met | |
| 145 | | | | 150 | | | | | 155 | | | | | 160 | | |

| gct | gat | cgc | ttg | cag | gga | tgg | ggc | gcg | acc | ctg | cag | tac | cac | gcg | gcg | 528 |
|---|---|---|---|---|---|---|---|---|---|---|---|---|---|---|---|---|
| Ala | Asp | Arg | Leu | Gln | Gly | Trp | Gly | Ala | Thr | Leu | Gln | Tyr | His | Ala | Ala | |
| | | | | 165 | | | | | 170 | | | | | 175 | | |

| aag | gct | ctg | gat | aca | caa | acc | gag | caa | cgg | ctc | ggc | ctg | cgc | cag | gtg | 576 |
|---|---|---|---|---|---|---|---|---|---|---|---|---|---|---|---|---|
| Lys | Ala | Leu | Asp | Thr | Gln | Thr | Glu | Gln | Arg | Leu | Gly | Leu | Arg | Gln | Val | |
| | | | 180 | | | | | 185 | | | | | 190 | | | |

| gcg | tgc | agc | gaa | ctc | ttc | gcc | agc | tcg | gac | ttc | atc | ctg | ctg | gcg | ctt | 624 |
|---|---|---|---|---|---|---|---|---|---|---|---|---|---|---|---|---|
| Ala | Cys | Ser | Glu | Leu | Phe | Ala | Ser | Ser | Asp | Phe | Ile | Leu | Leu | Ala | Leu | |
| | | 195 | | | | | 200 | | | | | 205 | | | | |

| ccc | ttg | aat | gcc | gat | acc | cag | cat | ctg | gtc | aac | gcc | gag | ctg | ctt | gcc | 672 |
|---|---|---|---|---|---|---|---|---|---|---|---|---|---|---|---|---|
| Pro | Leu | Asn | Ala | Asp | Thr | Gln | His | Leu | Val | Asn | Ala | Glu | Leu | Leu | Ala | |
| | 210 | | | | | 215 | | | | | 220 | | | | | |

| ctc | gta | cgg | ccg | ggc | gct | ctg | ctt | gta | aac | ccc | tgt | cgt | ggt | tcg | gta | 720 |
|---|---|---|---|---|---|---|---|---|---|---|---|---|---|---|---|---|
| Leu | Val | Arg | Pro | Gly | Ala | Leu | Leu | Val | Asn | Pro | Cys | Arg | Gly | Ser | Val | |
| 225 | | | | | 230 | | | | | 235 | | | | | 240 | |

| gtg | gat | gaa | gcc | gcc | gtg | ctc | gcg | gcg | ctt | gag | cga | ggc | cag | ctc | ggc | 768 |
|---|---|---|---|---|---|---|---|---|---|---|---|---|---|---|---|---|
| Val | Asp | Glu | Ala | Ala | Val | Leu | Ala | Ala | Leu | Glu | Arg | Gly | Gln | Leu | Gly | |
| | | | | 245 | | | | | 250 | | | | | 255 | | |

| ggg | tat | gcg | gcg | gat | gta | ttc | gaa | atg | gaa | gac | tgg | gct | cgc | gcg | gac | 816 |
|---|---|---|---|---|---|---|---|---|---|---|---|---|---|---|---|---|
| Gly | Tyr | Ala | Ala | Asp | Val | Phe | Glu | Met | Glu | Asp | Trp | Ala | Arg | Ala | Asp | |
| | | | 260 | | | | | 265 | | | | | 270 | | | |

-continued

| | | | | | | | | | | | | | | | |
|---|---|---|---|---|---|---|---|---|---|---|---|---|---|---|---|
| cgg | ccg | cag | ctg | atc | gat | cct | gcg | ctg | ctc | gcg | cat | ccg | aat | acg | ctg | 864 |
| Arg | Pro | Gln | Leu | Ile | Asp | Pro | Ala | Leu | Leu | Ala | His | Pro | Asn | Thr | Leu |
| | 275 | | | | | 280 | | | | | 285 | | | | | ttc act ccg cac ata ggg tcg gca gtg cgc gcg gtg cgc ctg gag att 912
Phe Thr Pro His Ile Gly Ser Ala Val Arg Ala Val Arg Leu Glu Ile
        290               295               300 gaa cgt tgt gca gcg cag aac atc atc cag gta ttg gca ggt gcg cgc 960
Glu Arg Cys Ala Ala Gln Asn Ile Ile Gln Val Leu Ala Gly Ala Arg
305               310               315               320 cca atc aac gct gcg aac cgt ctg ccc aag gcc aat cct gcc gca gac 1008
Pro Ile Asn Ala Ala Asn Arg Leu Pro Lys Ala Asn Pro Ala Ala Asp
                325               330               335 tga                                                              1011

<210> SEQ ID NO 32
<211> LENGTH: 1011
<212> TYPE: DNA
<213> ORGANISM: Pseudomonas stutzeri
<220> FEATURE:
<221> NAME/KEY: CDS
<222> LOCATION: (1)..(1008)

<400> SEQUENCE: 32 atg ctg ccg aaa ctc gtt ata act cac cga gta cac gaa gag atc ctg   48
Met Leu Pro Lys Leu Val Ile Thr His Arg Val His Glu Glu Ile Leu
 1               5                   10                  15 caa ctg ctg gcg cca cat tgc gag ctg ata acc aac cag acc gac agc   96
Gln Leu Leu Ala Pro His Cys Glu Leu Ile Thr Asn Gln Thr Asp Ser
                20                  25                  30 acg ctg acg cgc gag gaa att ctg cgc cgc tgt cgc gat gct cag gcg  144
Thr Leu Thr Arg Glu Glu Ile Leu Arg Arg Cys Arg Asp Ala Gln Ala
            35                  40                  45 atg atg gcg ttc atg ccc gat cgg gtc gat gca gac ttt ctt caa gcc  192
Met Met Ala Phe Met Pro Asp Arg Val Asp Ala Asp Phe Leu Gln Ala
        50                  55                  60 tgc cct gag ctg cgt gta gtc ggc tgc gcg ctc aag ggc ttc gac aat  240
Cys Pro Glu Leu Arg Val Val Gly Cys Ala Leu Lys Gly Phe Asp Asn
65                  70                  75                  80 ttc gat gtg gac gcc tgt act gcc cgc ggg gtc tgg ctg acc ttc gtg  288
Phe Asp Val Asp Ala Cys Thr Ala Arg Gly Val Trp Leu Thr Phe Val
                85                  90                  95 cct gat ctg ttg acg gtc ccg act gcc gag ctg gcg atc gga ctg gcg  336
Pro Asp Leu Leu Thr Val Pro Thr Ala Glu Leu Ala Ile Gly Leu Ala
            100                 105                 110 gtg ggg ctg ggg cgg cat ctg cgg gca gca gat gcg ttc gtc cgc tct  384
Val Gly Leu Gly Arg His Leu Arg Ala Ala Asp Ala Phe Val Arg Ser
        115                 120                 125 ggc gag ttc cag ggc tgg caa cca cgg ttc tac ggc acg ggg ctg gat  432
Gly Glu Phe Gln Gly Trp Gln Pro Arg Phe Tyr Gly Thr Gly Leu Asp
    130                 135                 140 aac gct acg gtc ggc ttc ctt ggc atg ggc gcc atc gga ctg gcc atg  480
Asn Ala Thr Val Gly Phe Leu Gly Met Gly Ala Ile Gly Leu Ala Met
145                 150                 155                 160 gct gat cgc ttg cag gga tgg ggc gcg acc ctg cag tac cac gcg gcg  528
Ala Asp Arg Leu Gln Gly Trp Gly Ala Thr Leu Gln Tyr His Ala Ala
                165                 170                 175 aag gct ctg gat aca caa acc gag caa cgg ctc ggc ctg cgc cag gtg  576
Lys Ala Leu Asp Thr Gln Thr Glu Gln Arg Leu Gly Leu Arg Gln Val
            180                 185                 190 gcg tgc agc gaa ctc ttc gcc agc tcg gac ttc atc ctg ctg gcg ctt  624
Ala Cys Ser Glu Leu Phe Ala Ser Ser Asp Phe Ile Leu Leu Ala Leu

```
                 195                 200                 205
ccc ttg aat gcc gat acc ctg cat ctg gtc aac gcc gag ctg ctt gcc    672
Pro Leu Asn Ala Asp Thr Leu His Leu Val Asn Ala Glu Leu Leu Ala
    210                 215                 220 ctc gta cgg ccg ggc gct ctg ctt gta aac ccc tgt cgt ggc tcg gta    720
Leu Val Arg Pro Gly Ala Leu Leu Val Asn Pro Cys Arg Gly Ser Val
225                 230                 235                 240 gtg gat gaa gcc gcc gtg ctc gcg gcg ctt gag cga ggc cag ctc ggc    768
Val Asp Glu Ala Ala Val Leu Ala Ala Leu Glu Arg Gly Gln Leu Gly
                245                 250                 255 ggg tat gcg gcg gat gta ttc gaa atg gaa gac tgg gct cgc gcg gac    816
Gly Tyr Ala Ala Asp Val Phe Glu Met Glu Asp Trp Ala Arg Ala Asp
            260                 265                 270 cgg ccg cag ctg atc gat cct gcg ctg ctc gcg cat ccg aat acg ctg    864
Arg Pro Gln Leu Ile Asp Pro Ala Leu Leu Ala His Pro Asn Thr Leu
        275                 280                 285 ttc act ccg cac ata ggg tcg gca gtg cgc gcg gtg cgc ctg gag att    912
Phe Thr Pro His Ile Gly Ser Ala Val Arg Ala Val Arg Leu Glu Ile
    290                 295                 300 gaa cgt tgt gca gcg cag aac atc atc cag gta ttg gca ggt gcg cgc    960
Glu Arg Cys Ala Ala Gln Asn Ile Ile Gln Val Leu Ala Gly Ala Arg
305                 310                 315                 320 cca atc aac gct gcg aac cgt ctg ccc aag gcc aat cct gcc gca gac   1008
Pro Ile Asn Ala Ala Asn Arg Leu Pro Lys Ala Asn Pro Ala Ala Asp
                325                 330                 335 tga                                                               1011

<210> SEQ ID NO 33
<211> LENGTH: 1011
<212> TYPE: DNA
<213> ORGANISM: Pseudomonas stutzeri
<220> FEATURE:
<221> NAME/KEY: CDS
<222> LOCATION: (1)..(1008)

<400> SEQUENCE: 33 atg ctg ccg aaa ctc gtt ata act cac cga gta cac gaa gag atc ctg     48
Met Leu Pro Lys Leu Val Ile Thr His Arg Val His Glu Glu Ile Leu
1               5                  10                  15 caa ctg ctg gcg cca cat tgc gag ctg ata acc aac cag acc gac agc     96
Gln Leu Leu Ala Pro His Cys Glu Leu Ile Thr Asn Gln Thr Asp Ser
            20                  25                  30 acg ctg acg cgc gag gaa att ctg cgc cgc tgt cgc gat gct cag gcg    144
Thr Leu Thr Arg Glu Glu Ile Leu Arg Arg Cys Arg Asp Ala Gln Ala
        35                  40                  45 atg atg gcg ttc atg ccc gat cgg gtc gat gca gac ttt ctt caa gcc    192
Met Met Ala Phe Met Pro Asp Arg Val Asp Ala Asp Phe Leu Gln Ala
    50                  55                  60 tgc cct gag ctg cgt gta gtc ggc tgc gcg ctc aag ggc ttc gac aat    240
Cys Pro Glu Leu Arg Val Val Gly Cys Ala Leu Lys Gly Phe Asp Asn
65                  70                  75                  80 ttc gat gtg gac gcc tgt act gcc cgc ggg gtc tgg ctg acc ttc gtg    288
Phe Asp Val Asp Ala Cys Thr Ala Arg Gly Val Trp Leu Thr Phe Val
                85                  90                  95 cct gat ctg ttg acg gtc ccg act gcc gag ctg gcg atc gga ctg gcg    336
Pro Asp Leu Leu Thr Val Pro Thr Ala Glu Leu Ala Ile Gly Leu Ala
            100                 105                 110 gtg ggg ctg ggg cgg cat ctg cgg gca gca gat gcg ttc gtc cgc tct    384
Val Gly Leu Gly Arg His Leu Arg Ala Ala Asp Ala Phe Val Arg Ser
        115                 120                 125
```

```
ggc gag ttc cgg ggc tgg caa cca cgg ttc tac ggc acg ggg ctg gat    432
Gly Glu Phe Arg Gly Trp Gln Pro Arg Phe Tyr Gly Thr Gly Leu Asp
    130             135                 140 aac gct acg gtc ggc ttc ctt ggc atg ggc gcc atc gga ctg gcc atg    480
Asn Ala Thr Val Gly Phe Leu Gly Met Gly Ala Ile Gly Leu Ala Met
145                 150                 155                 160 gct gat cgc ttg cag gga tgg ggc gcg acc ctg cag tac cac gcg gcg    528
Ala Asp Arg Leu Gln Gly Trp Gly Ala Thr Leu Gln Tyr His Ala Ala
                165                 170                 175 aag gct ctg gat aca caa acc gag caa cgg ctc ggc ctg cgc cag gtg    576
Lys Ala Leu Asp Thr Gln Thr Glu Gln Arg Leu Gly Leu Arg Gln Val
            180                 185                 190 gcg tgc agc gaa ctc ttc gcc agc tcg gac ttc atc ctg ctg gcg ctt    624
Ala Cys Ser Glu Leu Phe Ala Ser Ser Asp Phe Ile Leu Leu Ala Leu
        195                 200                 205 ccc ttg aat gcc gat acc ctg cat ctg gtc aac gcc gag ctg ctt gcc    672
Pro Leu Asn Ala Asp Thr Leu His Leu Val Asn Ala Glu Leu Leu Ala
    210                 215                 220 ctc gta cgg ccg ggc gct ctg ctt gta aac ccc tgt cgt ggt tcg gta    720
Leu Val Arg Pro Gly Ala Leu Leu Val Asn Pro Cys Arg Gly Ser Val
225                 230                 235                 240 gtg gat gaa gcc gcc gtg ctc gcg gcg ctt gag cga ggc cag ctc ggc    768
Val Asp Glu Ala Ala Val Leu Ala Ala Leu Glu Arg Gly Gln Leu Gly
                245                 250                 255 ggg tat gcg gcg gat gta ttc gaa atg gaa gac tgg gct cgc gcg gac    816
Gly Tyr Ala Ala Asp Val Phe Glu Met Glu Asp Trp Ala Arg Ala Asp
            260                 265                 270 cgg ccg cag ctg atc gat cct gcg ctg ctc gcg cat ccg aat acg ctg    864
Arg Pro Gln Leu Ile Asp Pro Ala Leu Leu Ala His Pro Asn Thr Leu
        275                 280                 285 ttc act ccg cac ata ggg tcg gca gtg cgc gcg gtg cgc ctg gag att    912
Phe Thr Pro His Ile Gly Ser Ala Val Arg Ala Val Arg Leu Glu Ile
    290                 295                 300 gaa cgt tgt gca gcg cag aac atc atc cag gta ttg gca ggt gcg cgc    960
Glu Arg Cys Ala Ala Gln Asn Ile Ile Gln Val Leu Ala Gly Ala Arg
305                 310                 315                 320 cca atc aac gct gcg aac cgt ctg ccc aag gcc aat cct gcc gca gac   1008
Pro Ile Asn Ala Ala Asn Arg Leu Pro Lys Ala Asn Pro Ala Ala Asp
                325                 330                 335 tga                                                               1011
```

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: 6-His tag

<400> SEQUENCE: 34

His His His His His His
 1               5